(12) United States Patent
Rodino-Klapac et al.

(10) Patent No.: US 12,258,573 B2
(45) Date of Patent: Mar. 25, 2025

(54) ADENO-ASSOCIATED VIRUS VECTOR DELIVERY OF ALPHA-SARCOGLYCAN AND THE TREATMENT OF MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, Grove City, OH (US); Danielle Griffin, Canal Winchester, OH (US); Jerry R. Mendell, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 17/635,978

(22) PCT Filed: Aug. 21, 2020

(86) PCT No.: PCT/US2020/047339
§ 371 (c)(1),
(2) Date: Feb. 16, 2022

(87) PCT Pub. No.: WO2021/035120
PCT Pub. Date: Feb. 25, 2021

(65) Prior Publication Data
US 2022/0290180 A1 Sep. 15, 2022

Related U.S. Application Data

(60) Provisional application No. 63/022,843, filed on May 11, 2020, provisional application No. 63/014,934, filed on Apr. 24, 2020, provisional application No. 62/889,749, filed on Aug. 21, 2019.

(51) Int. Cl.
| | |
|---|---|
| *C12N 15/86* | (2006.01) |
| *C07K 14/47* | (2006.01) |
| *A61K 48/00* | (2006.01) |
| *C07H 21/04* | (2006.01) |

(52) U.S. Cl.
CPC .......... *C12N 15/86* (2013.01); *C07K 14/4716* (2013.01); *A61K 48/005* (2013.01); *C07H 21/04* (2013.01); *C12N 2750/14143* (2013.01); *C12N 2830/008* (2013.01)

(58) Field of Classification Search
CPC .......... C12N 15/86; C12N 2750/14143; C12N 2830/008; A61K 48/005; A61K 48/0075; C07H 21/04
See application file for complete search history.

(56) References Cited

U.S. PATENT DOCUMENTS

| | | |
|---|---|---|
| 5,173,414 A | 12/1992 | Lebkowski et al. |
| 5,449,616 A | 9/1995 | Campbell et al. |
| 5,658,776 A | 8/1997 | Flotte et al. |
| 5,672,694 A | 9/1997 | Campbell et al. |
| 5,786,211 A | 7/1998 | Johnson |
| 5,871,982 A | 2/1999 | Wilson et al. |
| 6,204,059 B1 | 3/2001 | Samulski et al. |
| 6,258,595 B1 | 7/2001 | Gao et al. |
| 6,262,035 B1 | 7/2001 | Campbell et al. |
| 6,566,118 B1 | 5/2003 | Atkinson et al. |
| 6,632,800 B1 | 10/2003 | Russell et al. |
| 7,282,199 B2 | 10/2007 | Gao et al. |
| 7,790,449 B2 | 9/2010 | Gao et al. |
| 7,883,858 B2 | 2/2011 | Hood et al. |
| 9,061,059 B2 | 6/2015 | Chakraborty et al. |
| 9,434,928 B2 | 9/2016 | Mendell et al. |
| 10,105,453 B2 | 10/2018 | Mendell et al. |
| 11,358,993 B2 | 6/2022 | Rodino-Klapac et al. |
| 2001/0029040 A1 | 10/2001 | Toyo-Oka |
| 2003/0225260 A1 | 12/2003 | Snyder |
| 2006/0154250 A1 | 7/2006 | Morris et al. |
| 2007/0099251 A1 | 5/2007 | Zhang et al. |
| 2008/0249052 A1 | 10/2008 | Duan et al. |
| 2009/0054823 A1 | 2/2009 | Bridges et al. |
| 2009/0275107 A1 | 11/2009 | Lock et al. |
| 2009/0280103 A1 | 11/2009 | Flueck |
| 2010/0003218 A1 | 1/2010 | Duan et al. |
| 2010/0008979 A1 | 1/2010 | Tomatsu et al. |

(Continued)

FOREIGN PATENT DOCUMENTS

| | | |
|---|---|---|
| CN | 101310015 A | 11/2008 |
| CN | 101896186 A | 11/2010 |

(Continued)

OTHER PUBLICATIONS

Johns Hopkins Medicine, 2023 (Types of Muscular Dystrophy and Neuromuscular diseases, p. 1-4).*

(Continued)

*Primary Examiner* — Shin Lin Chen

(74) *Attorney, Agent, or Firm* — Foley & Lardner LLP

(57) ABSTRACT

Described herein are methods of treating muscular dystrophy in a subject, comprising administration of a recombinant AAV vector AAVrh74.tMCK.hSGCA using a systemic route of administration and at a dose of about $1.0 \times 10^{12}$ vg/kg to about $5.0 \times 10^{15}$ vg/kg. Further disclosed are methods of expressing alpha-sarcoglycan gene in a cell or in a subject in need thereof, decreasing a serum CK level, and increasing alpha-sarcoglycan positive fibers in muscle tissue of a subject.

13 Claims, 13 Drawing Sheets

Specification includes a Sequence Listing.

(56) References Cited

U.S. PATENT DOCUMENTS

| | | |
|---|---|---|
| 2010/0026655 A1 | 2/2010 | Harley |
| 2010/0075866 A1 | 3/2010 | Hood et al. |
| 2010/0112694 A1 | 5/2010 | Marban |
| 2010/0120627 A1 | 5/2010 | Belouchi et al. |
| 2010/0247495 A1 | 9/2010 | Ichim et al. |
| 2010/0266551 A1 | 10/2010 | Richard et al. |
| 2011/0023139 A1 | 1/2011 | Weinstein et al. |
| 2011/0053221 A1 | 3/2011 | Chen et al. |
| 2011/0070210 A1 | 3/2011 | Andrijauskas |
| 2011/0076744 A1 | 3/2011 | Wright et al. |
| 2011/0082192 A1 | 4/2011 | Milne et al. |
| 2011/0104120 A1 | 5/2011 | Xiao et al. |
| 2011/0266551 A1 | 11/2011 | Thompson et al. |
| 2011/0294193 A1 | 12/2011 | Amalfitano et al. |
| 2011/0301226 A1 | 12/2011 | Mendell et al. |
| 2012/0087862 A1 | 4/2012 | Hood et al. |
| 2013/0171172 A1 | 7/2013 | Richard et al. |
| 2014/0010861 A1 | 1/2014 | Bancel et al. |
| 2014/0147432 A1 | 5/2014 | Chakraborty et al. |
| 2014/0179770 A1 | 6/2014 | Zhang et al. |
| 2014/0234255 A1 | 8/2014 | Lai et al. |
| 2014/0249208 A1 | 9/2014 | Chakraborty et al. |
| 2014/0256802 A1 | 9/2014 | Boye et al. |
| 2014/0273231 A1 | 9/2014 | Zhang et al. |
| 2014/0323956 A1 | 10/2014 | Mendell et al. |
| 2015/0111955 A1 | 4/2015 | High et al. |
| 2015/0125429 A1 | 5/2015 | Perlingeiro et al. |
| 2015/0232883 A1 | 8/2015 | Dahlman et al. |
| 2015/0238627 A1 | 8/2015 | Leger et al. |
| 2016/0058890 A1 | 3/2016 | Buj Bello et al. |
| 2018/0256752 A1 | 9/2018 | Buj Bello et al. |
| 2019/0000998 A1 | 1/2019 | Mendell et al. |
| 2019/0202880 A1 | 7/2019 | Rodino-Klapac et al. |
| 2019/0343966 A1 | 11/2019 | Wang et al. |
| 2020/0339960 A1 | 10/2020 | Sahenk |
| 2021/0128749 A1 | 5/2021 | Rodino-Klapac et al. |
| 2021/0393801 A1 | 12/2021 | Rodino-Klapac et al. |
| 2023/0390417 A1 | 12/2023 | Sahenk |

FOREIGN PATENT DOCUMENTS

| | | |
|---|---|---|
| CO | 20210000227 A2 | 1/2021 |
| EP | 0 127 839 A2 | 12/1984 |
| EP | 0 155 476 A | 9/1985 |
| EP | 2 170 325 A | 4/2010 |
| EP | 2 859 896 A1 | 4/2015 |
| EP | 3 030 666 A | 6/2016 |
| JP | 2006-121961 A | 5/2006 |
| JP | 2015-509711 A | 4/2015 |
| JP | 2016-515831 A | 6/2016 |
| JP | 2019-513399 A | 5/2019 |
| TW | 201741458 A | 12/2017 |
| WO | WO-95/03392 A1 | 2/1995 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 98/09657 A2 | 3/1998 |
| WO | WO-99/01176 A1 | 1/1999 |
| WO | 99/11764 A2 | 3/1999 |
| WO | WO-99/43360 A1 | 9/1999 |
| WO | 01/83692 A2 | 11/2001 |
| WO | 02/53703 A2 | 7/2002 |
| WO | WO-03/074714 A1 | 9/2003 |
| WO | WO-2004/058146 A2 | 7/2004 |
| WO | WO-2007/057781 A2 | 5/2007 |
| WO | WO-2009/019505 A2 | 2/2009 |
| WO | WO-2009/054725 A2 | 4/2009 |
| WO | WO-2013/016352 A1 | 1/2013 |
| WO | WO 2013/078316 A1 | 5/2013 |
| WO | WO-2013/123503 A1 | 8/2013 |
| WO | WO-2013/151665 A2 | 10/2013 |
| WO | WO-2013/176772 A1 | 11/2013 |
| WO | WO-2014/037526 A1 | 3/2014 |
| WO | WO-2014/039916 A1 | 3/2014 |
| WO | WO-2014/093622 A2 | 6/2014 |
| WO | WO-2014/093712 A1 | 6/2014 |
| WO | WO-2014/204725 A1 | 12/2014 |
| WO | WO-2015/018503 A1 | 2/2015 |
| WO | WO-2015/021457 A2 | 2/2015 |
| WO | WO-2015/110449 A1 | 7/2015 |
| WO | WO-2015/158749 A2 | 10/2015 |
| WO | WO-2015/197232 A1 | 12/2015 |
| WO | WO-2016/115543 A2 | 7/2016 |
| WO | WO-2017/087395 A1 | 5/2017 |
| WO | WO-2017/165859 A1 | 9/2017 |
| WO | WO-2017/180857 A1 | 10/2017 |
| WO | WO-2017/180976 A1 | 10/2017 |
| WO | WO-2017/181014 A1 | 10/2017 |
| WO | WO-2017/181015 A1 | 10/2017 |
| WO | WO-2017/221145 A1 | 12/2017 |
| WO | WO-2018/170408 A1 | 9/2018 |
| WO | WO-2019/012336 A1 | 1/2019 |
| WO | WO-2019/078916 A1 | 4/2019 |
| WO | WO-2019/118806 A1 | 6/2019 |
| WO | WO-2019/152474 A1 | 8/2019 |
| WO | WO-2019/195362 A1 | 10/2019 |
| WO | WO-2019/209777 A1 | 10/2019 |
| WO | WO-2019/245973 A1 | 12/2019 |
| WO | WO-2020/006458 A1 | 1/2020 |
| WO | WO-2020/123645 A1 | 6/2020 |
| WO | WO-2020/176614 A1 | 9/2020 |
| WO | WO-2021/257655 A1 | 12/2021 |

OTHER PUBLICATIONS

Wikipedia, 2023 (Limb-girdle muscular dystrophy, p. 1-11).*
Allamand et al., Early adenovirus-mediated gene transfer effectively prevents muscular dystrophy in alpha-sarcoglycan-deficient mice, Gene Ther., 7(16):1385-91 (2000).
Asokan et al., The AAV Vector Toolkit: Poised at the Clinical Crossroads; Molecular Therapy, 20(4):699-708 (2012).
Carter, Adeno-associated virus vectors, Current Opinions in Biotechnology, 3(5):533-539 (1992).
Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Cserjesi et al., Myogenin induces the myocyte-specific enhancer binding factor MEF-2 independently of other muscle-specific gene products, Mol. Cell. Biol., 11(10):4854-4862 (1991).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Gao et al., Adeno-associated viruses undergo substantial evolution in primates during natural infections, Proc. Natl. Acad. Sci. U.S.A., 100:6081-6086 (2003).
Gao et al., Clades of Adeno-associated viruses are widely disseminated in human tissues, J. Virol., 78(12):6381-8 (2004).
Gombash et al., Adeno-Associated Viral Vector Delivery to the Enteric Nervous System: A Review, Postdoc J., 3(8):1-12 (2015).
Graham et al., A new technique for the assay of infectivity of human adenovirus 5 DNA, Virology, 52(2):456-67 (1973).
Hakim et al., Monitoring murine skeletal muscle function for muscle gene therapy, Methods Mol. Biol., 709:75-89 (2011).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
International Application No. PCT/US12/66265, International Preliminary Report on Patentability, mailed Jun. 5, 2014.
International Application No. PCT/US12/66265, International Search Report and Written Opinion, mailed Mar. 28, 2013.

(56) References Cited

OTHER PUBLICATIONS

International Application No. PCT/US20/47339, International Preliminary Report on Patentability, mailed Mar. 3, 2022.
Johnson et al., Muscle creatine kinase sequence elements regulating skeletal and cardiac muscle expression in transgenic mice, Mol. Cell Biol., 9(8):3393-9 (1989).
Justison et al., Percutaneous assisted venous return isolated limb perfusion, J. Extra Corpor. Technol., 41(4):231-4 (2009).
Laughlin et al., Cloning of infectious adeno-associated virus genomes in bacterial plasmids, Gene, 23(1):65-73 (1983).
Lebkowski et al., Adeno-associated virus: a vector system for efficient introduction and integration of DNA into a variety of mammalian cell types, Mol. Cell. Biol., 8(10):3988-3996, (1988).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector Design Tour de Force: Integrating Combinatorial and Rational Approaches to Derive Novel Adeno-associated Virus Variants, Molecular Therapy, 22(11):1900-1909 (2014).
Martin et al., Overexpression of Galgt2 in skeletal muscle prevents injury resulting from eccentric contractions in both mdx and wild-type mice, Am. J. Physiol. Cell Physiol., 296:C476-88 (2009).
McCarty et al., Adeno-associated virus terminal repeat (TR) mutant generates self0complementary vectors to overcome the rate-limiting step to transduction in vivo, Gene Ther., 10:2112-8 (2003).
McCarty et al., Self-complementary AAV Vectors; Advances and Applications, Molecular Therapy, 16(10):1648-1656 (2008).
McLaughlin et al., Adeno-associated virus general transduction vectors: analysis of proviral structures, J. Virol., 62(6):1963-73 (1988).
Mendell et al., Limb-girdle muscular dystrophy type 2D gene therapy restores alpha-sarcoglycan and associated proteins, Ann. Neurol., 66(3):290-7 (2009).
Muscat et al., Multiple 5'-flanking regions of the human alpha-skeletal actin gene synergistically modulate muscle-specific expression, Mol. Cell. Biol., 7(11):4089-4099 (1987).
Muzyczka, Use of Adeno-Associated Virus as a General Transduction Vector for Mammalian Cells, Curr. Topics in Microbiol and Immunol., 158:97-129 (1992).
Pacak et al., Long-term Skeletal Muscle Protection After Gene Transfer in a Mouse Model of LGMD-2D, Molecular Therapy, 15(10): 1775-1781 (2007).
Paul et al., Increased Viral Titer Through Concentration of Viral Harvests from Retroviral Packaging Lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Rabinowitz et al., Cross-packaging of a single adeno-associated virus (AAV) type 2 vector genome into multiple AAV serotypes enables transduction with broad specificity, J. Virol., 76(2):791-801 (2002).
Rodino-Klapac et al., A translational approach for limb vascular delivery of the micro-dystrophin gene without high volume or high pressure for treatment of Duchenne muscular dystrophy, J. Transl. Med., 5:45 (2007).
Rodino-Klapac et al., Lack of toxicity of alpha-sarcoglycan overexpression supports clinical gene transfer trial in LGMD2D, Neurology, 71(4):240-7 (2008).
Rodino-Klapac et al., Persistent expression of FLAG-tagged micro dystrophin in nonhuman primates following intramuscular and vascular delivery, Mol. Ther., 18(1)109-17 (2010).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schenpp et al., Highly purified recombinant adeno-associated virus vectors. Preparation and quantitation, Methods Mol. Med., 69:427-443 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Senapathy et al., Molecular cloning of adeno-associated virus variant genomes and generation of infectious virus by recombination in mammalian cells, J. Biol. Chem., 259:4661-4666 (1984).
Sonntag et al., A viral assembly factor promotes AAV2 capsid formation in the nucleolus, PNAS, 107(22):10220-10225 (2010).
Srivastava et al., Nucleotide sequence and organization of the adeno-associated virus 2 genome, J. Virol., 45(2):555-64 (1983).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
van Akkooi et al., Isolated limb perfusion for an irresectable melanoma recurrence in a Jehovah's witness, Eur. J. Cardiothorac. Surg., 30(2):408-10 (2006).
Wang et al., Recombinant AAV serotype 1 transduction efficiency and tropism in the murine brain, Gene Ther., 10(17):1528-34 (2003).
Weintraub et al., The myoD gene family: nodal point during specification of the muscle cell lineage, Science, 251:761-766 (1991).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 17(3):209-20 (2007).
Mendell et al., "Gene Delivery for Limb-Girdle Muscular Dystrophy Type 2D" by Isolated Limb Infusion, Human Gene Therapy, vol. 30 No. 7, (Mar. 5, 2019), pp. 794-801.
Mendell et al., "Gene Therapy for Muscular Dystrophy: Lessons Learned and Path Forward", Neuroscience Letters 527 (2012), pp. 90-99.
Mendell et al., "Sustained Alpha-Sarcoglycan Gene Expression after Gene Transfer in Limb-Girdle Muscular Dystrophy, Type 2D", Ann Neurol., 68(5), (2010) pp. 629-638.
International Search Report for PCT/US2020/047339 dated Dec. 10, 2020.
Written Opinion for PCT/US2020/047339 dated Dec. 10, 2020.
Mendell et al., Gene Delivery for Limb-Girdle Muscular Dystrophy Type 2D by Isolated Limb Infusion, Human Gene Therapy, 30(7): 794-801 (2019).
Griffin et al., Systemic Dose Escalation Study of Alpha-Sarcoglycan Provides Functional Improvement in SGCA (/-) Moguse Model of LGMD2D, Mol. Ther., 26(5S1): 166, (May 2018).
Griffin et al., Dose-Escalation of Systemically Delivered Adeno-Associated Virus-Mediated alpha-Sarcoglycan in a Mouse Model With Limb-Girdle Muscular Dystrophy Type 2D. Poster Presented at the 2019 Muscular Dystrophy Association Clinical Scientific Conference, Apr. 13-17, 2019.
Abadi et al., Supplementation with alpha-lipoic acid, CoQ10, and vitamin E augments running performance and mitochondrial function in female mice, PLoS One, 8(4):e60722 (2013).
ABSS (Sequence Alignment; WO2020006458, Seq ID #1; accessed Mar. 12, 2024) (Year: 2024).
ABSS2 (Sequence Alignment; U.S. Appl. No. 17/255,488, Seq ID #1; accessed Mar. 12, 2024) (Year: 2024).
Anderson et al., "Nucleic acid hybridisation: A practical approach," Ch. 4, IRL Press Limited, Oxford, England (1 page).
Anderson et al., "Quantitative Filter Hybridisation—Chapter 4", Nucleic acid hyridisation a practical approach, 1985, pp. 73-111.
Angelini et al., "The clinical spectrum of sarcoglycanopathies," Neurology, 52:176-179 (1999).
Araishi et al., "Loss of the sarcoglycan complex and sarcospan leads to muscular dystrophy in beta-sarcoglycan-deficient mice," Hum. Mal. Genet. 8: 1589-1598 (1999).

(56) References Cited

OTHER PUBLICATIONS

Arnold et al., Electrophysiological Biomarkers in Spinal Muscular Atrophy: Preclinical Proof of Concept, Ann. Clin. Transl. Neural., 1 (1 ):34-44 (Jan. 2014).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700-kDa titin isoform, and its interaction with obscurin identify a novel Z-line to I-band linking system, Gire. Res. 89:1065-72 (2001).
Barresi et al., Disruption of heart sarcoglycan complex and severe cardiomyopathy caused by beta sarcoglycan mutations, J. Med. Genet. 37: 102-107 (2000).
Bartoli et al., "Safety and efficacy of AAV-mediated calpain 3 gene transfer in a mouse model of limb-girdle muscular dystrophy type 2A", Mol. Ther., 13(2):250-259 (2006).
Bearzi et al., Human cardiac stem cells, Proc. Natl. Acad. Sci. USA. 104:14068-73 (2007).
Beastrom et al., mdx(5cv) mice manifest more severe muscle dysfunction and diaphragm force deficits than do mdx Mice, Am. J. Pathol., 179(5):2464-74 (2011).
Behlke, Chemical modification of siRNAs for in vivo use, Oligonucleotides. 18:305-319 (2008).
Belfort et al., Homing endonucleases: from genetic anomalies to programmable genomic clippers Methods Mal. Biol. 1123:1-26 (2014).
Boch et al., Breaking the code of DNA binding specificity of TAL-type III effectors, Science. 326:1509-12 (2009).
Boissel et al., "megaTALs" a rare-cleaving nuclease architecture for therapeutic genome engineering, Nucleic Acids Research, 2014, vol. 42, No. 4 (pp. 2591-2601).
Boissel et al., Assembly and characterization of megaTALs for hyperspecific genome engineering applications, Methods Mal. Biol. 1239: 171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bonnemann et al., Betasarcoglycan (A3b) mutations cause autosomal recessive muscular dystrophy with loss of the sarcoglycan complex, Nat. Genet., 11(3):266-273 (1995).
Bonnemann et al., Genomic screening for beta-sarcoglycan gene mutations: missense mutations may cause severe limb-girdle muscular dystrophy type 2E (LGMD 2E), Hum. Mol. Genet. 5:1953-1961 (1996).
Bouquet et al., Miyoshi-like distal myopathy with mutations in anoctamin 5 gene, Rev. Neural. (Paris), 168(2):135-41 (Feb. 2012).
Bramsen et al., Development of therapeutic-grade small interfering RNAs by chemical engineering, Front. Genet. 20:154 (2012).
Ceccadi et al., Homologous recombination-deficient tumors are hyper-dependent on POLQ mediated repair, Nature. 518:258-262 (2015).
Cekaite et al., Gene expression analysis in blood cells in response to unmodified and 2'-modified siRNAs reveals TLR-dependent and independent effects, J. Mal. Biol. 365:90-108 (2007).
Centner et al., Identification of muscle specific ring finger proteins as potential regulators of the titin kinase domain, J. Mal. Biol. 306:717-26 (2001).
Cermak et al., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239:133-59 (2015).
Ceyhan-Birsoy et al., Recessive truncating titin gene, TTN, mutations presenting as centronucleal myopathy, Neuroloov. 81:1205-14 (2013).
Chandrasekharan et al., Genetic defects in muscular dystrophy, Methods Enzymol. 479:291-322 (2010).

Chao et al., "Several log increase in therapeutic transgene delivery by distinct adeno-associated viral serotype vectors," Molecular therapy: the journal of the American Society of Gene Therapy, 2000, vol. 2, Issue 6, pp. 619-623.
Chao et al., "Sustained and complete phenotype correction of hemophilia B mice following intramuscular injection of AAV1 serotype vectors," Molecular therapy: the journal of the American Society of Gene Therapy, 2001, vol. 4, Issue 3, pp. 217-222.
Chauveau et al., A rising titan: TTN review and mutation update, Human Mutation. 35:1046-59 (2014).
Chernolovskaya et al., Chemical modification of siRNA, Curr. Opin. Mal. Ther. 12:158-67 (2010).
Chicoine et al., "Plasmapheresis eliminates the negative impact of AAV antibodies on microdystrophin gene expression following vascular delivery," Molecular therapy: the journal of the American Society of Gene Therapy, 2014, vol. 22, Issue 2, pp. 338-347.
Chicoine et al., "Vascular delivery of rAAVrh74.MCK.GALGT2 to the gastrocnemius muscle of the rhesus macaque stimulates the expression of dystrophin and laminin a2 surrogates", Mol. Ther., 22:713-24 (2014).
Chiorini et al., Cloning and characterization of adeno-associated virus type 5, J. Viral., 73(2):1309-19 (Feb. 1999).
Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).
Chu et al., "SV40 DNA transfection of cells in suspension: analysis of the efficiency of transcription and translation of T-antigen", GENE, 13, (1981) 197-202.
Clark et al., "Recombinant adeno-associated viral vectors mediate long-term transgene expression in muscle," Human gene therapy, 1997, vol. 8, Issue 6, pp. 659-669.
Cox et al., "Therapeutic genome editing: prospects and challenges," Nature Medicine, Feb. 21, 2015, vol. 2 (pp. 121-131).
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, Nov. 14, 2006 issue.
Daya et al., "Gene Therapy Using Adeno-Associated Virus Vectors," Clinical Microbiology Reviews, Oct. 2008, vol. 21, No. 4 (pp. 583-593).
Deleavey et al., Chemical modification of siRNA, Curr. Protoc. Nucleic Acid Chem. Chapter 16:Unit 16.3 (2009).
Doench et al., "Optimized sgRNA design to maximize activity and minimize off-target effects of CRISPR-Cas9", Nature Biotechnology, Feb. 2016, vol. 34, No. 2 (pp. 184-191).
Draviam et al., The beta-li-core of sarcoglycan is essential for deposition at the plasma membrane, Muscle and Nerve. 34:691-701 (2006).
Dreier et al., "Development of Zinc Finger Domains for Recognition of the 5'-ANN-3' Family of DNA Sequences and Their Use in the Construction of Artificial Transcription Factors," The Journal of Biological Chemistry, August 3, vol. 276, No. 31 (pp. 29466-29478).
Dreier et al., Insights into the molecular recognition of the 5'-GNN-3' family of DNA sequences by zinc finger domains, J. Mal. Biol. 303:489-502 (2000).
Dreier, B. et al., "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Dressman et al., Delivery of alpha- and beta-sarcoglycan by recombinant adeno-associated virus: efficient rescue of muscle, but differential toxicity, Hum. Gene. Ther., 13(13):1631-1646 (2002).
Dressman, AAV-Mediated gene transfer to models of muscular dystrophy: Insights into assembly of multi-subunit membrane proteins, University of Pittsburgh (1997).
Durbeej et al., Disruption of the beta-sarcoglycan gene reveals pathogenetic complexity of limb- girdle muscular dystrophy type 2E, Mol. Cell. 5:141-151 (2000).

(56) References Cited

OTHER PUBLICATIONS

Fanin et al., Gender difference in limb-girdle muscular dystrophy: a muscle fiber morphometric study in 101 patients, Clin. Neuropathology, 33:179-801 (2014).
Fanin et al., LGMD2E patients risk developing dilated cardiomyopathy, Neuromuscl. Disord., 13(4):303-309 (2003).
Flotte et al., "Gene expression from adeno-associated virus vectors in airway epithelial cells," American journal of respiratory cell and molecular biology, 1992, vol. 7, Issue 3, pp. 349-356.
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269:198-207 (2013).
Fowler, et al., Improved knockdown from artificial microRNAs in an enhanced miR-155 Backbone: a designer's guide to potent multi-target RNAi, Nucleic Acids Research, 44(5): e48, (Nov. 2015).
Foye, Whole Genome Sequencing Solved Our Family's Genetic Mystery: Titin, Narrat. Inq. Bioeth 5:206-8 (2015).
Francois, et al., Accurate Titration of Infectious AAV Particles Requires Measurement of Biologically Active Vector Genomes and Suitable Controls. Molecular Therapy—Methods & Clinical Development, Sep. 21, 2018, vol. 10, pp. 223-236.
Fucini et al., Adenosine modification may be preferred for reducing siRNA immune stimulation, Nucleic Acid Ther. 22:205-210 (2012).
Gaglione et al., Recent progress in chemically modified siRNAs, Mini. Rev. Med. Chem. 10:578-9t (2010).
Gao et al., A novel and efficient model of coronary artery ligation and myocardial infarction in the mouse, Gire. Res. 107:1445-53 (2010).
Gao et al., A novel and efficient model of coronary artery ligation in the mouse, Methods Mal. Bic 1037:299-311 (2013).
Gautel et al., The central Z-disk region of titin is assembled from a novel repeat in variable copy Nos., Journal of Cell Science. 109:2747-2754 (1996).
Gebeyehu, et al., "Novel biotinylated nucleotide -- analogs for labeling and colorimetric detection of DNA," Nucleic Acids Research, vol. 15, No. 11, (Jun. 11, 1987), p. 4513-4534.
GenBank Accession No. AF028704.1, Adena-associated virus 6, complete genome, Jan. 12, 1998.
GenBank Accession No. AF028705.1, Adeno-associated virus 3B, complete genome, Jan. 12, 1998.
GenBank Accession No. AF085716.1, Adeno-associated virus 5 DNA binding trs helicase (Rep22) and capsid protein (VP1) aenes, complete eds, Feb. 9, 1999.
Genbank Accession No. AX753246, Sequence 1 from Patent EP1310571, Jun. 23, 2003.
GenBank Accession No. AX753249, Sequence 4 from Patent EP1310571, Jun. 23, 2003.
GenBank Accession No. AX753250.1, Sequence 5 from Patent EP1310571, Jun. 23, 2003.
GenBank Accession No. AY631965.1, Adena-associated virus 10 nonstructural protein and caps protein genes, complete eds, Nov. 30, 2004.
GenBank Accession No. AY631966.1, Adena-associated virus 11 nonstructural protein and caps protein genes, complete eds, Nov. 30, 2004.
GenBank Accession No. DO813647.1, Adena-associated virus 12 Rep78 and VP1 genes, complete eds, Feb. 20, 2008.
GenBank Accession No. EU285562.1, Adena-associated virus 13 nonstructural protein and capsid protein genes, complete eds, Sep. 23, 2008.
Genbank Accession No. NC_001401.0, Adeno-associated virus-2, complete genome, Aug. 13, 2018.
GenBank Accession No. NC_001401.2, Adeno-associated virus-2, complete genome, Aug. 13, 2018.
Genbank Accession No. NC_001729.1, Adeno-associated virus-3, complete genome, Aug. 13, 2018.
GenBank Accession No. NC_001829.1, Adeno-associated virus-4, complete genome, Aug. 13, 2018.
GenBank Accession No. NC_001862, Adeno-associated virus 6, complete genome, Jan. 12, 2004, located at <https:www.ncbi.nlm.nih.gov/nuccore/NC_001862.1?report=genbank>.
GenBank Accession No. NC_002077.1, Adeno-associated virus-1, complete genome, Aug. 13, 2018, located at <https://www.ncbi.nlm.nih.gov/nuccore/NC_002077>.
GenBank Accession No. NC_006152.1, Adeno-associated virus 5, complete genome, Aug. 13, 2018.
GenBank Accession No. NC_006260.1, Adeno-associated virus-7, complete genome, Aug. 13, 2018.
GenBank Accession No. NC_006261.1, Adeno-associated virus-8, complete genome, Aug. 13, 2018.
Genbank Accession No. NM_00232.4, Homo sapiens sarcoglycan beta {SGCB}, Mma, Feb. 20, 2019.
Genbank Accession No. NP 000233.1, Beta Sarcoglyan {43kD dystrophin-associated glycoprotein) Homo Sapiens, Mar. 19, 1999.
Genbank Accession No. J01901, Adeno-associated virus 2, complete genome, Apr. 27, 1993.
GenBank Accession No. U89790.1, Adeno-associated virus 4, complete genome, Aug. 21, 2017.
GenBank Registered No. NG_011618, Homo sapiens titin (TTN), RefSeqGene (LRG_391) on chromosome 2 dated, Apr. 5, 2020.
Genbank Synthetic construct Homo sapiens clone IMAGE: 100069183, MGC: 199194 anoctamin 5 (ANO5) mRNA, encodes complete protein GenBank: BC172489.1 dated Mar. 16, 2009.
GenBank: Accession No. NP 000223.1: beta-sarcoglycan sequence, dated Mar. 03, 1999.
Georganopoulou et al., "A Journey with LGMD: From Protein Abnormalities to Patient Impact", The Protein Journal, Kluwer Academic/Plenum Publishers, Dordrecht, NL, vol. 40, No. 4, Jun. 10, 2021, pp. 466-488.
Gerull et al., Identification of a novel frameshift mutation in the giant muscle filament titin in a large Australian family with dilated cardiomyopathy, J. Mal. Med. (Berl). 84:478-83 (2006).
Gerull et al., Mutations of TTN, encoding the giant muscle filament titin, cause familial dilated cardiomyopathy, Nat. Genet. 30:201-4 (2002).
Gibertini et al., Fibrosis and inflammation are greater in muscles of beta-sarcoglycan-null mouse than mdx mouse, Cell Tissue Res. 356:427-443 (2014).
Goeddel, "Gene Expression Technology: Methods in Enzymology," Academic Press, vol. 185, Jun. 11, 1990, pp. 3-7.
Govoni et al., "Ongoing therapeutics trials and outcome measures for Duchenne muscular dystrophy", Cell Mol. Life Sci., 70:4585-602 (2013).
Gramlich et al., "Antisense-mediated exon skipping: a therapeutic strategy for titin-based dilated cardiomyopathy," EMBO Molecular Medicine, 7(5): 562-76 (2015).
Gramlich et al., "Stress-induced dilated cardiomyopathy in a knock-in mouse model mimicking human titin-based disease", J. Mal. Cell Cadiol. 47:352-8 (2009).
Granzier et al., "Deleting titin's I-band/A-band junction reveals critical roles for titin in biomechanica sensing and cardiac function", Proc. Natl. Acad. Sci. USA. 111:14589-94 (2014).
Greig et al., "Impact of intravenous infusion time on AAV8 vector pharmacokinetics, safety, and liver transduction in cynomolgus macaques," Molecular Therapy - Methods & Clinical Develop, 3:16079, 7 pages (2016).
Grieger et al., "Production and characterization of adeno-associated viral vectors", Nat. Protoc. 1:1412-1428 (2006).
Griffin et al. Preclinical systemic delivery of adeno-associated [alpha]-sarcoglycan gene transfer for limb-girdle muscular dystrophy, Human Gene Therapy, 32(7-8): 390-404, (Apr. 2021).
Griffin et al., "Defective Membrane Fusion and Repair in Anoctamin5-Deficient Muscular Dystrophy", Human Molecular Genetics, vol. 25, No. 10, pp. 1900-1911 (Feb. 23, 2016).
Grose et al., "Homologous Recombination Mediates Functional Recovery of Dysferlin Deficiency following AAV5 Gene Transfer", PLoS One, Jun. 2012, vol. 7, Issue 6, e39233.

(56) References Cited

OTHER PUBLICATIONS

Guilinger et al., "Fusion of catalytically inactive Cas9 to FokI nuclease improves the specificity of genome modification," Nature Biotechnology, vol. 32, No. 6, Jun. 2014 (pp. 577-582).
Gutschner et al., "Genome engineering - Matching supply with demand," Cell Cycle, 15(11): 1395-96 2016.
Hafez et al., "Homing endonucleases: DNA scissors on a mission", Genome. 55:553-69 (2012).
Hagan, "When are mice considered old?" The Jackson Laboratory, https://www.jax.org/news-and-insights/jax-blog/2017/november/when-are-mice-considered-old# Nov. 7, 2017 (8 pages).
Hakim et al., The passive mechanical properties of the extensor digitorum longus muscle are compromised in 2- to 20-mo-old mdx mice, J. Appl. Physiol. 110: 1656-1663 (2011).
Handschin et al., Peroxisome proliferator-activated receptor gamma coactivator 1 coactivators, energy homeostasis, and metabolism, Endocrine reviews, 27:728-735 (2002).
Herman et al., "Truncations of titin causing dilated cardiomyopathy", N. Engl. J. Med. 366:619-28, 2012.
Herzog et al., Stable gene transfer and expression of human blood coagulation factor IX after intramuscular injection of recombinant adeno-associated virus, Proc. Natl. Acad. Sci. USA, 1997, vol. 94 (pp. 5804-5809).
Hicks et al., A founder mutation in Anoctamin 5 is a major cause of limb-girdle muscular dystrophy, Brain, 134 (Pt. 1):171-82 (Jan. 2011).
Horii et al., Validation of microinjection methods for generating knockout mice by CRISPR/Cas-mediated genome engineering, Sci Rep. 4:4513 (2014).
Inouye et al., "Codon optimization of genes for efficient protein expression in mammalian cells by selection of only preferred human codons," Protein Expression and Purification, 2015, vol. 109, pp. 47-54.
International Application No. PCT/US2017/027636, International Preliminary Report on Patentability, mailed Oct. 16, 2018 (5 pages).
International Application No. PCT/US2017/027636, International Search Report and Written Opinion, mailed Jul. 5, 2017 (8 Pages).
International Application No. PCT/US19/39893, International Preliminary Report on Patentability, mailed Jan. 7, 2021.
International Application No. PCT/US19/39893, International Search Report and Written Opinion, mailed Sep. 25, 2019.
International Application No. PCT/US2016/061703, International Preliminary Report on Patentability, mailed May 15, 2018.
International Application No. PCT/US2020/019892, International Preliminary Report on Patentability, mailed Sep. 10, 2021 (8 pages).
International Preliminary Report on Patentability for Appl. Ser. No. PCT/US20119/03983 dated Dec. 29, 2020 (7 pages).
International Preliminary Report on Patentability for Appl. Ser. No. PCT/US2016/062052 dated May 22, 2018.
International Preliminary Report on Patentability for Appl. Ser. No. PCT/US2017/027583 dated Oct. 25, 2018.
International Search Report and Written Opinion for Appl. Ser. No. PCT/US2016/062052 dated Feb. 7, 2017 (5 pages).
International Search Report and Written Opinion for Appl. Ser. No. PCT/US2017/027583 dated Jul. 14, 2017 (8 pages).
International Search Report and Written Opinion for Appl. Ser. No. PCTUS2016/061703 dated Feb. 2, 2017 (13 pages).
International Search Report issued in connection with PCT/US2020/019892 dated May 14, 2020 (4 pages).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., "A Programmable Dual-RNA-Guided DNA Endonuclease in Adaptive Bacterial Immunity," Science, Aug. 17, 2012, 337(6096):816-821.

Judge et al., "Design of noninflammatory synthetic siRNA mediating potent gene silencing in vivo", Mol. Ther. 13:494-505 (2006).
Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).
Kariko et al., "Suppression of RNA recognition by Toll-like receptors: the impact of nucleoside modification and the evolutionary origin of RNA," Immunity, Aug. 2005, vol. 23 (pp. 165-175).
Kennell, "Principles and Practices of Nucleic Acid Hybridization," Progress in Nucleic Acid Research and Molecular Biology, Academic Press, vol. 11, 1971, (pp. 259-301).
Kent et al., "Mechanism of microhomology-mediated end-joining promoted by human DNA polymerase theta", Nat. Struct. Mol. Biol. 22:230-237 (2015).
Kessler et al., "Gene delivery to skeletal muscle results in sustained expression and systemic delivery of a therapeutic protein," PNAS, 1996, vol. 93, pp. 14082-14087.
Kirnbauer et al., Virus-like particles of bovine papillomavirus type 4 in prophylactic and therapeutic immunization, Virology, 219(1):37-44 (May 1996).
Kleinstiver et al., The I-TevI nuclease and linker domains contribute to the specificity of monomerh TALENs, G3 (Bethesda). 4:1155-65 (2014).
Kobayashi et al., Sarcolemma-localized nNOS is required to maintain activity after mild exercise, Nature. 456:511-5 (2008).
Kole et al., "RNA therapeutics: beyond RNA interference and antisense oligonucleotides", Nat Rev Drug Discov. Jan. 20, 2012;11(2):125-40. doi: 10.1038/nrd3625.
Kolmerer et al., "Genomic organization of M line titin and its tissue-specific expression in two distinct isoforms", J. Mol. Biol. 256:556-63 (1996).
Kormann et al., "Expression of therapeutic proteins after delivery of chemically modified mRNA in mice," Nature Biotechnology, Feb. 2011, vol. 29, No. 2 (pp. 154-157).
Kornberg et al., "The early history of DNA polymerase: a commentary by Arthur Kornberg", Biochimica et Biophysica Acta. 1000:53-56 (1989).
Kotin et al., "Manufacturing Clinical Grade Recombinant Adeno-Associated Virus Using Invertebrate Cell Lines," Human Gene Therapy, 28(4):Abstract Only, (Apr. 1, 2017).
Kotin et al., Manufacturing Clinical Grade Recombinant Adeno-Associated Virus Using Invertebrate Cell Lines, Hum. Gene Ther., 28(4 ):350-360 (2017).
Kramerova et al., "Null mutation of calpain 3 {p94} in mice causes abnormal sarcomere formation in vivo and in vitro", Hum. Mol. Genet., 13(13):1373-1388 (2004).
Kramerova et al., Failure to up-regulate transcription of genes necessary for muscle adaptation underlies limb girdle muscular dystrophy 2A calpainopathy, Hum. Mol. Genet., 25(11):2194-2207 (2016).
Labeit et al., "Titins: giant proteins in charge of muscle ultrastructure and elasticity", Science. 270:293-6 (1995).
Laws et al., Progression of kyphosis in mdx mice, J. Appl. Physiol. 97:1970-7 (2004).
Lewinter et al., Cardiac titin and heart disease, J. Cardiovasc. Pharmacol. 63:207-12 (2014).
Lewinter, "Titin isoforms in heart failure: are there benefits to supersizing", Circulation. 110:109-11 2004.
Lewis et al., "Generation of neutralizing activity against human immunodeficiency virus type 1 in serum by antibody gene transfer," Journal of virology, 2002, vol. 76, Issue 17, pp. 8769-8775.
Li et al., "Modularly assembled designer TAL effector nucleases for targeted gene knockout and gene replacement in eukaryotes," Nucleic Acids Research, 2011, vol. 39, No. 14 (pp. 6315-6325).
Li et al., Electrical impedance myography for the in vivo and ex vivo assessment of muscular dystrophy (mdx) mouse muscle, Muscle Nerve, 49(6):829-35 (Jun. 2014).
Li et al., Electrophysiologic biomarkers for assessing disease progression and the effect of riluzole in SOD1 G93A ALS mice, PLoS One, 8(6):e65976 (Jun. 2013).

(56) References Cited

OTHER PUBLICATIONS

Li et al., Intracoronary administration of cardiac stem cells in mice: a new, improved technique for cell therapy in murine models, Basic Res. Cardiol. 106:849-64 (2011).
Lin et al., Transcriptional co-activator PGC-1 alpha drives the formation of slow-twitch muscle fibres, Nature, 418:797-801 (2002).
Liu et al., "Adeno-associated virus-mediated microdystrophin expression protects young mdx muscle from contraction-induced injury," Molecular therapy: the journal of the American Society of Gene Therapy, 2005, vol. 11, Issue 2, pp. 245-256.
Liu et al., "Validated Zinc Finger Protein Designs for All 16 GNN DNA Triplet Targets," The Journal of Biological Chemistry, Feb. 8, 2002, vol. 277, No. 6 (pp. 3850-3856).
Louis et al., "EM_EST:BE676391", Jan. 27, 2011 (Jan. 27, 2011), XP055708767, Retrieved from the Internet: URL:http://ibis.internal.epo.org/exam/dbfetch.jsp?id=EM_EST:BE676391 [retrieved on Jun. 25, 2020].
Ma et al., Pol III Promoters to express small RNAs: Delineation of transcription initiation, Mol. Ther. Nucleic Acids. 3:e161 (2014).
Mahmood et al., "Limb-girdle muscular dystrophies: Where next after six decades from the first proposal (review)," Molecular Medicine reports, 2014, vol. 9 (pp. 1515-1532).
Mak et al., "The crystal structure of TAL effector PthXo1 bound to its DNA target," Science, Feb. 10, 2012, vol. 335, No. 6069 (pp. 716-719).
Makarenko et al., Passive stiffness changes caused by upregulation of compliant titin isoforms in human dilated cardiomyopathy hearts, Gire. Res. 95:708-16 (2004).
Mashiko et al., Generation of mutant mice by pronuclear injection of circular plasmid expressing Cas9 and single guided RNA, Sci. Rep. 3:3355 (2013).
Mateos-Gomez et al., Mammalian Polymerase theta promotes alternative-NHEJ amd suppresses recombination, Nature. 518:254-257 (2015).
Matsuda et al., Visualization of dystrophic muscle fibers in mdx mouse by vital staining with Evans blue: evidence of apoptosis in dystrophin-deficient muscle, J. Biochem., 118(5):959-964 (1995).
McCarty et al., "Self-complementary recombinant adeno-associated virus (scAAV) vectors promote efficient transduction independently of DNA synthesis", Gene Therapy, May 22, 2001, vol. 8, pp. 1248-1254.
McNally et al., The genetic landscape of cardiomyopathy and its role in heart failure, Cell. Metab. 21:174-182 (2015).
Meadows et al., Micro-RNA-29 Overexpression by adeno-associated virus suppresses fibrosis in mdx:utrn+/—Mice (S61.003), Neurology, 82:S61.003 (Abstract) (2014).
Meadows et al., Reducing Skeletal Muscle Fibrosis with AAV-Delivered miR-29, 2012, Neurology, vol. 78, Issue 1, Supplement PO4.089.
Melacini et al., Heart involvement in muscular dystrophies due to sarcoglycan gene mutations, Muscle Nerve. 22:473-479 (1999).
Mendell et al., "A phase 1/2a follistatin gene therapy trial for becker muscular dystrophy," Molecular therapy: the journal of the American Society of Gene Therapy, 2015, vol. 23, Issue 1, pp. 192-201.
Mendell et al., "Sustained alpha-sarcoglycan gene expression after gene transfer in limb-girdle muscular dystrophy, type 2D," Annals of neurology, 2010, vol. 68, Issue 5, p. 629?
Mendell et al., Gene Therapy for Spinal Muscular Atrophy Type 1 Shows Potential to Improve Survival and Motor Functional Outcomes, Mol. Ther. 24:S190 (2016).
Mendell et al., Single-Dose Gene-Replacement Therapy for Spinal Muscular Atrophy, N. Engl. J. Med., 377:1713-1722 (2017).
Merten, O.W., Aav vector production: state of the art developments and remaining challenges. Cell and Gene Therapy Insights, Dec. 1, 2016, vol. 2, No. 5, pp. 521-551.
Mingozzi et al. "Therapeutic in vivo gene transfer for genetic disease using AAV: progress and challenges", Nature Reviews Genetics, May 2011, vol. 12 (pp. 341-355).

Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).
Moore et al., Limb-girdle muscular dystrophy in the United States, J. Neuropathol. Exp. Neural., 65(10):995-1003 (2006).
Moorwood et al., Isometric and eccentric force generation assessment of skeletal muscles isolated from murine models of muscular dystrophies, Journal of Visualized Experiments. 71 :e50036 (2013).
Mori et al., "Two novel adeno-associated viruses from cynomolgus monkey: pseudotyping characterization of capsid protein," Virology, 2004, vol. 330, Issue 2, pp. 375-383.
Moscou et al., "A Simple Cipher Governs DNA Recognition by TAL Effectors", Science, Dec. 11, 2009, vol. 326 (p. 1501).
Murphy et al., "Long-term correction of obesity and diabetes in genetically obese mice by a single intramuscular injection of recombinant adeno-associated virus encoding mouse leptin," Proceedings of the National Academy of Sciences of the United States of America, 1997, vol. 94, Issue 25, pp. 13921-13926.
Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, Neurology, 83:1453-1463 (2014).
NCBI Accession No. NG_051363.1, Homo sapiens TTN antisense RNA 1 (TTN-AS1), RefSeqGene on chromosome 2, dated Feb. 17, 2020.
NCBI Accession No. XM_012650762.1, Predicted: Propithecus coquereli titin (TTN), mRNA, dated Jun. 1, 2015.
NCBI Accession No. XM_024453100.1, Predicted: Homo sapiens titin (TTN), transcript variant X12, mRNA, dated Mar. 1, 2020.
Ncbi Blast Tool: Pairwise Similarity 1, Instant App ('488) Seq ID No. 1 [1-3977]: U.S. Pat. No. 9981049B2 Seq Id No. 8 (CAPN3) (2024).
Ncbi Blast Tool: Pairwise Similarity 2, Instant App ('488) Seq ID No. 1 [1107-3572]:: U.S. Pat. No. 9981049B2 Seq Id No. 8 (CAPN3) (2024).
NCBI Reference Sequence: "anoctamin-5 isoform a [homo sapiens]", GenPept, Mar. 15, 2015, NP_998764.1.
Obermann et al., Molecular structure of the sarcomeric M band: mapping of titin and myosin binding domains in myomesin and the identification of a potential regulatory phosphorylation site in myomesin, EMBO J. 16:211-20 (1997).
Pavlovicova et al., Structure and composition of tubular aggregates of skeletal muscle fibres, Gen. Physiol. Biophys., 22(4):425-40 (Dec. 2003).
Payne et al., Nutritional therapy improves function and complements corticosteroid intervention in mdx mice. Muscle Nerve. Jan. 2006; 33(1):66-77.
Peer et al., Special delivery: targeted therapy with small RNAs, Gene. Ther. 18:1127-33 (2011).
Peled et al., Titin mutation in familial restrictive cardiomyopathy, Int. J. Cardiol. 171:24-30 (2014).
Penttila et al., Eight new mutations and the expanding phenotype variability in muscular dystrophy caused by ANOS, Neurology, 78(12): 897-903 (Mar. 2012).
Powers et al., Exercise-induced oxidative stress in humans: cause and consequences, Free Radic. Biol. Med., 51 (5):942-50 (Sep. 2011).
Pozsgai et al., "Beta-Sarcoglycan gene transfer decreases fibrosis and restores force in LGMD2E mice," Gene Therapy, 2016, vol. 23 (pp. 57-66).
Pozsgai et al., "Beta-Sarcoglycan Gene Transfer Leads to Functional Improvement in a Model of LGMD2E," Molecular Therapy vol. 22, Supplement 1, May 2014 (p. S199).
Pozsgai et al., "Pre-Clinical Efficacy Study of Beta-Sarcoglycan Gene Transfer," Molecular Therapy, May 1, 2013, vol. 21, No. 1 (p. S68).
Pozsgai et al., "Systemic AAV-Mediated [beta]-Sarcoglycan Delivery Targeting Cardiac and Skeletal Muscle Ameliorates Histological

(56) References Cited

OTHER PUBLICATIONS and Functional Deficits in LGMD2E Mice," Molecular Therapy, The Journal of the American Society of Gene Therapy, Apr. 2017, vol. 25, No. 4 (pp. 855-869).
Rafael-Fortney et al., Early treatment with lisinopril and spironolactone preserves cardiac and skeletal muscle in duchenne muscular dystrophy mice, Circulation. 124:582-8 (2011).
Raj et al., "Self-complementary adeno-associated viral vectors for gene therapy of hemophilia B: progress and challenges" Expert Review of Hematology, Oct. 2011, vol. 4, No. 5 (pp. 539-549).
Ran et al., "In vivo genome editing using Staphylococcus aureus Cas9," Nature, Apr., 9, 2015, vol. 520, (18 pages).
Richard et al., "Mutations In The Proteolytic Enzyme Calpain 3 Cause Limb-Girdle Muscular Dystrophy Type 2A", Cell, 81(1):27-40 (1995).
Roberts et al., Integrated allelic, transcriptional, and phenomic dissection of the cardiac effects of titin truncations in health and disease, Sci. Transl. Med. 7:270ra6 (2015).
Rodino-Klapac et al., "Micro-dystrophin and follistatin co-delivery restores muscle function in aged DMD model," Human Molecular Genetics, Dec. 2013, vol. 22, No. 24 (pp. 4929-4937).
Rodino-Klapac et al., Demonstration of SGCA Expression and Related Outcomes in Phase 1/1Ia Safety Isolated Limb Perfusion Trial in LGMD2D Subjects, Molecular Theerapy, 2018, vol. 26, Issue 5, Supplemental 1, p. 1, Abstract No. 250.
Roudaut et al., "Restriction of Calpain3 Expression to the Skeletal Muscle Prevents Cardiac Toxicity and Corrects Pathology in a Murine Model of Limb-Girdle Muscular Dystrophy", Circulation, 128(10): 1094-1104, (Sep. 2013).
Ruffing et al., "Mutations in the carboxy terminus of adeno-associated virus 2 capsid proteins affect viral infectivity: lack of an RGD integrin-binding motif," Journal of General Virology, 1994, vol. 75, pp. 3385-3392.
Rutledge et al., Infectious clones and vectors derived from adeno-associated virus (AAV) serotypes other than AAV type 2, J. Viral., 7291):309-19 (Jan. 1998).
Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).
Salva et al., "Design of Tissue-specific Regulatory Cassettes for High-level rAAV-mediated Expression in Skeletal and Cardiac Muscle," Mol. Ther., 2007, vol. 15, Issue 2, pp. 320-329.
Sambrook et al., "Molecular Cloning, A Laboratory Manual", Cold Spring Harbor Laboratory Press, Cold Spring Harbor, N.Y., 1989, 30 pages.
Sambrook et al., Cold spring harbor laboratory press, cold Spring Harbor, N.Y., (2001).
Sambrook et al., Molecular Cloning: A Laboratory Manual, 2" edition (1989).
Sander et al., CRISPR-Cas systems for editing, regulating and targeting genomes, Nat. Biotechnol. 32:347-55 (2014).
Sandona et al., Sarcoglycanopalhies: molecular pathogenesis and therapeutic prospects, Exp Rev. Mol. Med. 11:e28 (2009).
Sanganalmath et al., Cell therapy for heart failure: a comprehensive overview of experimental and clincal studes, current challenges, and future directions, Gire. Res. 113:810-34 (2013).
Sarepta Therapeutics: "Sarepta Therapeutics' Investigational Gene Therapy SRP-9003 for the Treatment of Limb-Girdle Muscular Dystrophy Type 2E Shows Sustained Expression and Functional Improvements 2 Years After Administration", Mar. 18, 2021, pp. 1-3, Retrieved from the Internet: URL: https://investorrelations. sarepta.com/ news-releases/news-release-details/sarepta-therapeutics-investigational-gene-therapy-srp-9003-0 [retrieved on Jun. 23, 2023].
Schreiber et al., The transcriptional coactivator PGC-1 regulates the expression and activity of the orphan nuclear receptor estrogen-related receptor alpha (ERRalpha), J. Biol. Chem., 278: 9013-9018 (2003).
Segal et al., "Toward controlling gene expression at will: Selection and design of zinc finger domains recognizing each of the 5'-GNN-3' DNA target sequences," Proceedings of the National Academy of Sciences, USA, Mar. 1999, vol. 96 (pp. 2758-2763).
Semplicini et al., Clinical and genetic spectrum in limb-girdle muscular dystrophy type 2E, Neurology, 84:1772-81 (2015).
Shield et al., E-box sites and a proximal regulatory region of the muscle creatine kinase gene differentially regulate expression in diverse skeletal muscles and cardiac muscle of transgenic mice, Mal. Cell. Biol., 16(9):5058-5068 (1996).
Shih et al., "Finding the Achilles" heel of Muscle Giant-TALEN-mediated Gene-editing in Zebrafish Titin', Circulation Research, Oct. 21, 2015, vol. 117, No.(suppl_1), pp. A344. DOI: https://doi.org/10.1161/res.117.suppl_1.344.
Siu et al., Familial dilated cardiomyopathy locus maps to chromosome 2q31, Circulation. 99:1022-6 (1999).
Smith et al., Modification and secretion of human interleukin 2 produced in insect cells by a baculovirus expression vector, Proc. Natl. Acad. Sci. USA, 82(24):8404-8 (1985).
Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.
Sorimachi et al., Tissue-specific expression and alpha-actinin binding properties of the Z-disc titin: implications for the nature of vertebrate Z-discs, J. Mal. Biol. 270:688-95 (1997).
Soutschek et al., "Therapeutic silencing of an endogenous gene by systemic administration of modified siRNAs," Nature, Nov. 2004, pp. 173-178, vol. 432.
Steentoft et al., Precision genome editing: a small revolution for glycobiology, Glycobiology. 24:663-80 (2014).
Straub et al., Animal models for muscular dystrophy show different patterns of sarcolemmal disruption, J. Cell Biol. 139:375-385 (1997).
Strobel, et al. "Antioxidant Supplementation Reduces Skeletal Muscle Mitochondrial Biogenesis", Official Journal of the American College of Sports Medicine, 2011, pp. 1017-1024.
Sun et al., Correction of Multiple Striated Muscles in Murine Pompe Disease Through Adena-Associated Virus-mediated Gene Therapy, Mal. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided FokI nucleases for highly specific genome editing, Nat. Biotechnol. 32:569-76 (2014).
Voikar et al., Long-term individual housing in C57BU6J and DBA/2 mice: assessment of behavioral consequences, Genes Brain Behav., 4(4):240-52 (2005).
Volkov et al., Selective protection of nuclease-sensitive sites in siRNA prolongs silencing effect, Oligonucleotides. 19:191-202 (2009).
Wang et al., "Construction and analysis of compact muscle-specific promoters for AAV vectors," Gene Therapy, 2008, vol. 15, Issue 22, pp. 1489-1499.
Wang et al., "The potential of adeno-associated viral vectors for gene delivery to muscle tissue", Exp. Opin. on Drug. Del., 11(3):345-364 (2014).
Wang et al., Loss of miR-29 in myoblasts contributes to dystrophic muscle pathogenesis, Mol. Ther., 20(6):1222-33 (2012).
Wang et al., Rapid and efficient assembly of transcription activator-like effector genes by USER cloning, J. Genet. Genomics. 41:339-47 (2014).
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).

(56) References Cited

OTHER PUBLICATIONS

Wein et al., Translation from a DMD exon 5 IRES results in a functional dystrophin isoform that attenuates dystrophinopathy in humans and mice, Nature Medicine, 20(9):992-1000 (2014).
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Winkler, Oligonucleotide conjugates for therapeutic applications, Ther. De/iv. 4:791-809 (2013).
Witting et al: "Anoctamin 5 muscular dystrophy in Denmark: prevalence, genotypes, phenotypes, cardiac findings, and muscleprotein expression", Case Reports, May 14, 2013, PMID: 23670307 DOI: 10.1007/s00415-013-6934-y.
Wolfs et al., MegaTevs: single-chain dual nucleases for efficient gene disruption, Nucliec Acids Res. 42:8816-29 (2014).
Wong-Kisiel et al., Two siblings with limb-girdle muscular dystrophy type 2E responsive to deflazacort, Neuromusc. Disord. 20:122-124 (2010).
Wu et al., Mutational analysis of the adeno-associated virus type 2 (AAV2) capsid gene and construction of AAV2 vectors with altered tropism, J. Viral., 74(18):8635-47 (Sep. 2000).
Xiao et al. "Production of High-Titer Recombinant Adeno-Associated Virus Vectors in the Absence of Helper Adenovirus," Journal of Virology, Mar. 1998, vol. 72 No. 3 (pp. 2224-2232).
Xiao et al., "Efficient long-term gene transfer into muscle tissue of immunocompetent mice by adeno-associated virus vector," Journal of virology, 1996, vol. 70, Issue 11, pp. 8098-8108.
Xu et al., "An Isolated Limb Infusion Method Allows for Broad Distribution of rAAVrh74.MCK.GALGT2 to Leg Skeletal Muscles in the Rhesus Macaque," Molecular Therapy—Methods & Clinical Develop, 10:89-104 (Sep. 2018).
Xu et al., "Genetic disruption of Ano5 in mice does not recapitulate human ANO5-deficient muscular dystrophy," Skeletal Muscle, 2015, vol. 5, No. 43 (pp. 1-14).
Yalvac et al., Impaired regeneration in calpain-3 null muscle is associated with perturbations in mTORC1 signaling and defective mitochondrial biogenesis, Skelet. Muscle, 7:27, 18 pages (2017).
Yan et al., Inverted terminal repeat sequences are important for intermolecular recombination and circularization of adeno-associated virus genomes, J. Viral., 79(1):364-79 (Jan. 2005).
Yuasa et al., "Gene therapy of muscular dystrophy: Systemic gene delivery to skeletal muscles" Jan. 2007, Drug Delivery System 22(2): 140-147, doi.org/10.2745/dds.22.140 (English Abstract).
Zanotti et al., Opposing roles of miR-21 and miR-29 in the progression of fibrosis in Duchenne muscular dystrophy., Biochem. Biophys. Acta., 1852:1451-4 (2015).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhang et al., Dual AAV therapy ameliorates exercise-induced muscle injury and functional ischemia in murine models of Duchenne muscular dystrophy, Hum. Mal. Genet. 22:3720-9 (2013).
Zhao et al., BPV1 E2 protein enhances packaging of full-length plasmid DNA in BPV1 pseudovirions, Virology, 272(2):382-93 (Jul. 2000).
Zhou et al., Pressure Overload by Transverse Aortic Constriction Induces Maladaptive Hypertrophy in a Titin-Truncated Mouse Model, Biomed. Res. Int. 2015:163564 (2015).
Zou et al., "An internal promoter underlies the difference in disease severity between N- and C- terminal truncation mutations of Titin in zebrafish", eLife, Oct. 16, 2015, vol. 4, pages e09406. DOI: https://doi.org/10.7554/eLife.09406.
Cordier et al., "Muscle-Specific Promoters May Be Necessary for Adeno-Associated Virus-Mediated Gene Transfer in the Treatment of Muscular Dystrophies," Human Gene Therapy, Jan. 20, 2001, vol. 12, pp. 205-215.
Cordier et al., "Rescue of Skeletal Muscles of gamma-Sarcoglycan-Deficient Mice with Adeno-Associated Virus-Mediated Gene Transfer," Molecular Therapy, Feb. 2000, vol. 1, No. 2 pp. 119-129.
Herson et al., A phase I trial of adeno-associated virus serotype 1-gamma-sarcoglycan gene therapy for limb girdle muscular type 2C, Brain, 2012, vol. 135, Pt 2, pp. 483-492.
McNally et al., "Mild and Severe Muscular Dystrophy Caused by a Single gamma-Sarcoglycan Mutation", American Journal of Human Genetics, Nov. 1996, vol. 59, No. 5, pp. 1040-1047.
NCBI, GenBank accession No. U34976.1 (Nov. 8, 1995), 2 pages.
Noguchi S, "Human gamma-sarcoglycan mRNA, complete cds.", NCBI, (Nov. 8, 1995), Database accession No. U34976, 2 pages.
Pozsgai et al., "506. [beta] —Sarcoglycan Gene Transfer Prevents Muscle Fibrosis and Inflammation in an Aged LGMD2E Mouse Model," Molecular Therapy, vol. 23 Supplement 1, May 2015, 2 pages.
Dorange et al., "Analytical approaches to characterize AAV vector production & purification: Advances and challenges," Cell & Gene Therapy Insights, 4(2):119-129 (2018).
Hou et al., "Serious Overestimation in Quantitative PCR by Circular (Supercoiled) Plasmid Standard: Microalgal pcna as the Model Gene," PLoS One 5(3):e9545, 8 pages (Mar. 5, 2010) doi: 10.1371/journal.pone.0009545.
Martinez-Fernandez de la Camara et al., "The accurate quantification of AAV genomic titre depends on the conformation of the plasmid reference," ARVO Annual Meeting Abstract, 3 pages, Jul. 2018.
Wu et al., "Adeno-associated virus serotypes: vector toolkit for human gene therapy." Molecular therapy 14.3 (2006): 316-327 (Year: 2006).
Werling et al., "Systematic comparison and validation of quantitative real-time PCR methods for the quantitation of adeno-associated viral products," Human Gene Therapy Methods, 26.3:82-92 (Jun. 2015).
Thomas et al., "B4GALNT2 (GALGT2) Gene Therapy Reduces Skeletal Muscle Pathology in the FKRP P448L Mouse Model of Limb Girdle Muscular Dystrophy 21", Am. J_ Pathol., 186(9):2429-2448 (2016).
Chu et al., "The limb-girdle muscular dystrophies: is treatment on the horizon?" Neurotherapeutics, 15(4):849-862 (Oct. 2018).
Monies et al., "A first-line diagnostic assay for limb-girdle muscular dystropy and other nyopathies", Human Genomics, 10(1):32, pp. 1-7 (Sep. 27, 2016).
Theadom et al., "Prealence of muscular dystrophies: a systematic literature review," Neuroepidemiology 43(3-4):259-68 (2014).
Wagner et al., "A novel method for the quantification of adeno-associated virus vectors for RNA interference applications using quantitative polymerase chain reaction and purified genomic adeno-associated virus DNA as a standard," Human Gene Therapy Methods, 24(6):355-63 (Dec. 2013).
Walter et al., "Recent developments in Duchenne muscular dystrophy: facts and numbers," Journal of Cachexia, Sarcopenia and Muscle, 8(5):681-685 (Oct. 2017).

\* cited by examiner

ADENO-ASSOCIATED VIRUS VECTOR DELIVERY OF ALPHA-SARCOGLYCAN AND THE TREATMENT OF MUSCULAR DYSTROPHY

RELATED APPLICATIONS

This application claims priority to U.S. Provisional Application No. 62/889,749 filed Aug. 21, 2019, U.S. Provisional Application No. 63/014,934, filed Apr. 24, 2020 and U.S. Provisional Application No. 63/022,843 filed May 11, 2020, all of which are incorporated by reference herein in their entirety.

FIELD OF THE INVENTION

Described herein are therapy vectors such as AAV vectors expressing alpha-sarcoglycan and method of using these vectors to treat limb girdle muscular dystrophies such as LGMD2D.

INCORPORATION BY REFERENCE OF THE SEQUENCE LISTING

This application contains, as a separate part of disclosure, a Sequence Listing in computer-readable form (filename: 54652_SeqListing.txt; 18,768 byte-ASCII text file; created Aug. 17, 2020) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One group of MDs is the limb girdle muscular dystrophies (LGMD). LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

Specialized tests for LGMD are now available through a national scheme for diagnosis, the National Commissioning Group (NCG).

LGMD subtype 2D (LGMD2D), often referred to as α-sarcoglycanopathy, is an autosomal recessive disorder caused by mutations in the alpha-sarcoglycan gene (SGCA; α-sarcoglycan), leading to complete or reduced loss of functional protein with loss of other structural components of the dystrophin-associated protein complex. Notably, loss of the alpha-sarcoglycan protein leads to a progressive muscular dystrophy with deteriorating muscle function, with an onset from 3 to 8 years of age. Symptoms include: delayed ambulation, weakness in proximal muscles caused by fat replacement and fibrosis, elevated creatine kinase, scoliosis, and joint contractures. The debilitating disease often leads to wheelchair dependency and death due to respiratory failure. Thus, there remains a need for treatments for LGMD2D.

SUMMARY

Described herein are methods for treating muscular dystrophy in a subject in need thereof comprising the step of administering a recombinant adeno-associated virus (rAAV) AAVrh74.tMCK.SGCA, wherein the rAAV is administered using a systemic route of administration and at a dose of about $1.0 \times 10^{12}$ vg/kg to about $5.0 \times 10^{15}$ vg/kg based on a supercoiled DNA or plasmid as the quantitation standard. In one aspect, the disclosure relates to an rAAV expressing the alpha-sarcoglycan gene and methods of delivering alpha-sarcoglycan to the muscle to reduce and/or prevent fibrosis; and/or to increase muscular force, and/or to treat a a-sarcoglycanopathy in a subject suffering from muscular dystrophy.

In one aspect, described herein is a recombinant AAV (rAAV) comprising a polynucleotide sequence encoding alpha-sarcoglycan protein. In some embodiments, the polynucleotide sequence comprises a sequence at least 65%, 70%, 75%, 80%, 81%, 82%, 83%, 84%, 85%, 86%, 87%, 88%, or 89%, 90%, 91%, 92%, 93%, 94%, 95%, 96%, 97%, 98%, 99% or 99.5% identical to the nucleotide sequence set forth in SEQ ID NO: 1 and encodes a protein that retains alpha-sarcoglycan activity. In some embodiments, the polynucleotide sequence comprises the nucleotide sequence set forth in SEQ ID NO: 1. In another embodiment, the polynucleotide encodes a protein that is at least 65%, 70%, 75%, 80%, 81%, 82%, 83%, 84%, 85%, 86%, 87%, 88%, or 89%, 90%, 91%, 92%, 93%, 94%, 95%, 96%, 97%, 98%, 99% or 99.5% identical to the nucleotide sequence set forth in SEQ ID NO: 2. In another embodiment, the polynucleotide encodes a protein that comprises an amino acid sequence set forth in SEQ ID NO: 2.

In some embodiments, the rAAV comprises a nucleotide sequence comprising a tMCK promoter. For example, the tMCK promoter comprises a nucleotide sequence set forth in SEQ ID NO: 3. In addition, the rAAV comprises a 5' inverted terminal repeat sequence of SEQ ID NO: 5 and/or a 3' inverted terminal repeat sequence of SEQ ID NO: 6. In some embodiments, the rAAV comprises a poly A sequence of SEQ ID NO: 7. In one embodiment, the disclosed rAAV is of the serotype AAVrh.74.

In one embodiment, the polynucleotide comprises a nucleotide sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 99.5% identical to SEQ ID NO: 4. In one embodiment, the polynucleotide comprises a nucleotide sequence set forth in SEQ ID NO: 4.

The disclosure provides for methods of treating muscular dystrophy in a subject in need thereof comprising the step of administering any of the rAAV disclosed herein, wherein the rAAV is administered by a systemic route. In particular, in any of the disclosed methods, the rAAV is AAVrh74.tMCK.SGCA, wherein the rAAV is administered using a systemic route of administration.

In any of the disclosed methods, the rAAV is administered at a dose of about $1.0 \times 10^{12}$ vg/kg to about $5.0 \times 10^{15}$ vg/kg based on a supercoiled DNA or plasmid as the quantitation standard. For example, the rAAV is administered at a dose of about $1.0 \times 10^{12}$ vg/kg to about $2.0 \times 10^{15}$ vg/kg, about $5 \times 10^{12}$ vg/kg to about $1.0 \times 10^{15}$ vg/kg, about $1.0 \times 10^{13}$ vg/kg to about $5.0 \times 10^{14}$ vg/kg, about $2.0 \times 10^{13}$ vg/kg to about $3.0 \times 10^{14}$ vg/kg, or about $5 \times 10^{13}$ vg/kg to about $2 \times 10^{14}$ vg/kg, or the rAAV is administered at a dose of about $5 \times 10^{13}$ vg/kg, about $6 \times 10^{13}$ vg/kg, about $7 \times 10^{13}$ vg/kg, about $8 \times 10^{13}$ vg/kg, about $9 \times 10^{13}$ vg/kg, about $1 \times 10^{14}$ vg/kg, about $2 \times 10^{14}$ vg/kg, about $3 \times 10^{14}$ vg/kg, about $4 \times 10^{14}$ vg/kg or about $5 \times 10^{14}$ vg/kg based on a supercoiled DNA or plasmid as the quantitation standard.

In another embodiment, in any of the disclosed methods, the rAAV is administered at a dose about $1.85 \times 10^{13}$ vg/kg or $7.41 \times 10^{13}$ vg/kg based on a linearized DNA or plasmid as the quantitation standard. For example, the rAAV is administered at a dose of about $1.0 \times 10^{13}$ vg/kg to about $8.0 \times 10^{13}$ vg/kg, about $1.5 \times 10^{13}$ vg/kg to about $8.0 \times 10^{13}$ vg/kg, about $1.6 \times 10^{13}$ vg/kg to about $8.0 \times 10^{13}$ vg/kg, about $1.8 \times 10^{13}$ vg/kg to about $8.0 \times 10^{13}$ vg/kg, about $1.2 \times 10^{13}$ vg/kg to about $7.5 \times 10^{13}$ vg/kg, about $1.9 \times 10^{13}$ vg/kg to about $7.5 \times 10^{13}$ vg/kg, about $1.4 \times 10^{13}$ vg/kg to about $7.4 \times 10^{13}$ vg/kg, about $1.9 \times 10^{13}$ vg/kg to about $7.5 \times 10^{13}$ vg/kg, or about $1.8 \times 10^{13}$ vg/kg to about $8.0 \times 10^{13}$ vg/kg based on a linearized DNA or plasmid as the quantitation standard.

In addition, in any of the disclosed methods, the systemic route of administration is an intravenous route. For example, in any of the disclosed methods, the rAAV is administered by injection, infusion or implantation. In some embodiments, the rAAV is administered by an intravenous route through a peripheral limb vein.

In any of the disclosed methods, the muscular dystrophy is limb-girdle muscular dystrophy. For example, the muscular dystrophy is limb-girdle muscular dystrophy type 2D (LGMD2D).

In an exemplary embodiment, the methods of treating muscular dystrophy, comprise administering the rAAV to a subject is suffering from limb-girdle muscular dystrophy, and the rAAV is administered by intravenous infusion at a dose of about $5 \times 10^{13}$ vg/kg to about $2 \times 10^{14}$ vg/kg based on a supercoiled DNA or plasmid as the quantitation standard, and wherein the rAAV comprises the scAAVrh74.tMCK.hSGCA construct nucleotide sequence of SEQ ID NO: 4.

In exemplary embodiments, the disclosure provides for methods of treating muscular dystrophy in a subject in need thereof, the method comprising the step of administering a rAAV to the subject wherein the subject is suffering from limb-girdle muscular dystrophy, and the rAAV is administered by intravenous infusion at a dose of about $5 \times 10^{13}$ vg/kg to about $2 \times 10^{14}$ vg/kg based on a supercoiled DNA or plasmid as the quantitation standard, and wherein the rAAV comprises the scAAVrh74.tMCK.hSGCA construct nucleotide sequence of SEQ ID NO: 4. For example, in these methods, the level of alpha-sarcoglycan gene expression in a cell of the subject is increased after administration of the rAAV as compared to the level of alpha-sarcoglycan gene expression before administration of the rAAV.

In any of the disclosed methods, the level of alpha-sarcoglycan gene expression in a cell of the subject is increased after administration of the rAAV as compared to the level of alpha-sarcoglycan gene expression before administration of the rAAV; and/or wherein the serum CK level in the subject is decreased after administration of the rAAV as compared to serum CK level before administration of the rAAV; and/or wherein the locomotor activity and specific-force generation are increased; wherein fibrosis is reduced; wherein the resistance to contraction-induced injury in tibialis anterior muscle is increased; and/or wherein the number of alpha-sarcoglycan positive fibers in the muscle tissue of the subject is increased after administration of the rAAV as compared to the number of alpha-sarcoglycan positive fibers before administration of the rAAV; or wherein fibrosis is reduced in the subject after administration of the rAAV as compared to before administration of the rAAV; and/or wherein fibrosis is reduced in the subject after administration of the rAAV as compared to before administration of the rAAV; and/or wherein the specific force, the fiber diameter size, and/or the eccentric contraction in the muscle of the subject are increased after administration of the rAAV as compared to before administration of the rAAV.

In some embodiments, the alpha-sarcoglycan gene expression is detected by measuring the alpha-sarcoglycan protein level by Western blot, and/or immunohistochemistry.

In another aspect, the disclosure provides for methods of expressing alpha-sarcoglycan gene in a cell comprising administering to a subject any of the disclosed rAAV. For example, the disclosure provides for method of expressing alpha-sarcoglycan gene in a cell comprising administering to a subject the scAAVrh74.tMCK.hSGCA construct nucleotide sequence of SEQ ID NO: 4. In addition, in any of the methods, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for methods of decreasing serum CK level in a subject in need thereof, the method comprising administering to the subject any of the disclosed rAAV. For example, the disclosure provides for methods of decreasing a serum CK level in a subject in need thereof, the method comprising administering to the subject the scAAVrh74.tMCK.hSGCA construct nucleotide sequence of SEQ ID NO: 4.

In another aspect, the disclosure provide for methods of increasing alpha-sarcoglycan positive fibers in a muscle tissue of a subject comprising administering to the subject any of the disclosed rAAV. For example, the disclosure provides for method of increasing alpha-sarcoglycan positive fibers in a muscle tissue of a subject in a need thereof, the method comprising administering to the subject the scAAVrh74.tMCK.hSGCA construct nucleotide sequence of SEQ ID NO: 4.

The disclosure also provides for methods of increasing the expression of alpha-sarcoglycan in a subject in need thereof comprising administering to the subject any of the disclosed rAAV. For example, the disclosure provides for methods of increasing the expression of alpha-sarcoglycan in a subject in need thereof, the method comprising administering to the subject the scAAVrh74.tMCK.hSGCA construct nucleotide sequence of SEQ ID NO: 4. In addition, in any of the disclosed methods, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for compositions for treating muscular dystrophy in a subject in need thereof, wherein the composition comprises any of the rAAV disclosed herein, wherein the composition is formulated for administration by a systemic route. In particular, in any of the compositions, the rAAV is AAVrh74.tMCK.SGCA.

Any of the disclosed compositions comprise rAAV at a dose of about $1.0 \times 10^{12}$ vg/kg to about $5.0 \times 10^{15}$ vg/kg based on a supercoiled DNA or plasmid as the quantitation standard. For example, the rAAV is at a dose of about $1.0 \times 10^{12}$ vg/kg to about $2.0 \times 10^{15}$ vg/kg, about $5 \times 10^{12}$ vg/kg to about $1.0 \times 10^{15}$ vg/kg, about $1.0 \times 10^{13}$ vg/kg to about $5.0 \times 10^{14}$ vg/kg, about $2.0 \times 10^{13}$ vg/kg to about $3.0 \times 10^{14}$ vg/kg, or about $5 \times 10^{13}$ vg/kg to about $2 \times 10^{14}$ vg/kg, or the rAAV is at a dose of about $5 \times 10^{13}$ vg/kg, about $6 \times 10^{13}$ vg/kg, about $7 \times 10^{13}$ vg/kg, about $8 \times 10^{13}$ vg/kg, about $9 \times 10^{13}$ vg/kg, about $1 \times 10^{14}$ vg/kg, about $2 \times 10^{14}$ vg/kg, about $3 \times 10^{14}$ vg/kg, about $4 \times 10^{14}$ vg/kg or about $5 \times 10^{14}$ vg/kg based on a supercoiled DNA or plasmid as the quantitation standard.

In another embodiment, in any of the disclosed compositions, the rAAV is administered at a dose about $1.85 \times 10^{13}$ vg/kg or about $7.41 \times 10^{13}$ vg/kg based on a linearized DNA or plasmid as the quantitation standard. For example, the rAAV is administered at a dose of about $1.0 \times 10^{13}$ vg/kg to about $8.0 \times 10^{13}$ vg/kg, about $1.5 \times 10^{13}$ vg/kg to about $8.0 \times 10^{13}$ vg/kg, about $1.6 \times 10^{13}$ vg/kg to about $8.0 \times 10^{13}$ vg/kg, about $1.8 \times 10^{13}$ vg/kg to about $8.0 \times 10^{13}$ vg/kg, about $1.2 \times 10^{13}$ vg/kg to about $7.5 \times 10^{13}$ vg/kg, about $1.9 \times 10^{13}$ vg/kg to about $7.5 \times 10^{13}$ vg/kg, about $1.4 \times 10^{13}$ vg/kg to about $7.4 \times 10^{13}$ vg/kg, about $1.9 \times 10^{13}$ vg/kg to about $7.5 \times 10^{13}$ vg/kg, or about $1.8 \times 10^{13}$ vg/kg to about $8.0 \times 10^{13}$ vg/kg based on a linearized DNA or plasmid as the quantitation standard.

In addition, any of the disclosed compositions are formulated for administration by an intravenous route, such as compositions formulated for administration by injection, infusion or implantation. In some embodiments, the disclosed compositions are formulated for administration by an intravenous route through a peripheral limb vein.

Any of the disclosed compositions are for the treatment for limb-girdle muscular dystrophy, such as limb-girdle muscular dystrophy type 2D (LGMD2D).

In an exemplary embodiment, the disclosure provides for compositions for treating a subject suffering from limb-girdle muscular dystrophy, wherein the composition comprises a dose of rAAV at about $5 \times 10^{13}$ vg/kg to about $2 \times 10^{14}$ vg/kg based on a supercoiled DNA or plasmid as the quantitation standard, and wherein the composition is formulated for administration by intravenous infusion, and wherein the rAAV comprises the scAAVrh74.tMCK.hSGCA construct nucleotide sequence of SEQ ID NO: 4.

In addition, the disclosure provides for compositions for treating limb-girdle muscular dystrophy in a subject in need thereof, wherein the composition comprises a dose of rAAV of about $5 \times 10^{13}$ vg/kg to about $2 \times 10^{14}$ vg/kg based on a supercoiled DNA or plasmid as the quantitation standard, and the composition is formulated for administration by intravenous infusion and wherein the rAAV comprises the scAAVrh74.tMCK.hSGCA construct nucleotide sequence of SEQ ID NO: 4. For example, administration of the composition increases the level of alpha-sarcoglycan gene expression in a cell of the subject as compared to the level of alpha-sarcoglycan gene expression before administration of the composition.

In addition, administration of any of the disclosed compositions increases the level of alpha-sarcoglycan gene expression in a cell of the subject as compared to the level of alpha-sarcoglycan gene expression before administration of the composition; and/or wherein administration of the disclosed composition decreased the serum CK level in the subject as compared to serum CK level before administration of the composition; and/or wherein the locomotor activity and specific-force generation are increased; wherein fibrosis is reduced; wherein the resistance to contraction-induced injury in tibialis anterior muscle is increased; and/or wherein administration of the composition increases the number of alpha-sarcoglycan positive fibers in the muscle tissue of the subject as compared to the number of alpha-sarcoglycan positive fibers before administration of the composition; and/or wherein administration of composition reduced fibrosis in the subject as compared to before administration of the rAAV; and/or wherein the composition reduced fibrosis as compared to before administration of the composition; or wherein administration of the composition increased the specific force, the fiber diameter size, and/or the eccentric contraction in the muscle of the subject as compared to before administration of the composition. In some embodiments, the alpha-sarcoglycan gene expression is detected by measuring the alpha-sarcoglycan protein level by Western blot, and/or immunohistochemistry.

In another aspect, the disclosure provides for compositions for expressing alpha-sarcoglycan gene in a cell, wherein composition comprises any of the disclosed rAAV. For example, the disclosure provides compositions for expressing alpha-sarcoglycan gene in a cell comprising the scAAVrh74.tMCK.hSGCA construct nucleotide sequence of SEQ ID NO: 4. In addition, in any of the compositions, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for compositions for decreasing a serum CK level in a subject in need thereof, the composition comprising any of the disclosed rAAV. For example, the disclosure provides for compositions for decreasing a serum CK level in a subject in need thereof, the composition comprises the scAAVrh74.tMCK.hSGCA construct nucleotide sequence of SEQ ID NO: 4.

In another aspect, the disclosure provides for composition for increasing alpha-sarcoglycan positive fibers in a muscle tissue of a subject, wherein the composition comprises any of the disclosed rAAV. For example, the disclosure provides for compositions for increasing alpha-sarcoglycan positive fibers in a muscle tissue of a subject, wherein the composition comprises the scAAVrh74.tMCK.hSGCA construct nucleotide sequence of SEQ ID NO: 4.

The disclosure also provides for composition for increasing the expression of alpha-sarcoglycan in a subject in need thereof, wherein the composition comprises any of the disclosed rAAV. For example, the disclosure provides compositions for increasing the expression of alpha-sarcoglycan in a subject in need thereof, wherein the composition comprises the scAAVrh74.tMCK.hSGCA construct nucleotide sequence of SEQ ID NO: 4. In addition, after administration of the any of the disclosed compositions, the expression of the alpha-sarcoglycan gene in the cell of the subject is detected by measuring the alpha-sarcoglycan protein level on a Western blot in muscle biopsies. Alternatively, after administration of the any of the disclosed compositions, the expression of the alpha-sarcoglycan gene in the cell is detected by measuring the alpha-sarcoglycan protein level by immunohistochemistry in muscle biopsies. In other embodiments, after administration of the any of the disclosed compositions, the expression of the alpha-sarcoglycan gene is measured in the subject by detecting the number of vector genome per microgram of genomic DNA.

The disclosure provides for use of any of the disclosed rAAV for the preparation of a medicament for the treating muscular dystrophy in a subject in need thereof, wherein the medicament is formulated for administration by a systemic route. In particular, the disclosure provides for use of AAVrh74.tMCK.SGCA for the preparation of a medicament for treating muscular dystrophy, wherein the medicament is formulated for administration by a systemic route of administration.

In any of the disclosed uses, the medicament comprises rAAV at a dose of about $1.0 \times 10^{12}$ vg/kg to about $5.0 \times 10^{15}$ vg/kg based on a supercoiled DNA or plasmid as the quantitation standard. For example, the rAAV is at a dose of about $1.0 \times 10^{12}$ vg/kg to about $2.0 \times 10^{15}$ vg/kg, about $5 \times 10^{12}$ vg/kg to about $1.0 \times 10^{15}$ vg/kg, about $1.0 \times 10^{13}$ vg/kg to about $5.0 \times 10^{14}$ vg/kg, about $2.0 \times 10^{13}$ vg/kg to about $3.0 \times 10^{14}$ vg/kg, or about $5 \times 10^{13}$ vg/kg to about $2 \times 10^{14}$ vg/kg, or the rAAV is at a dose of about $5 \times 10^{13}$ vg/kg, about $6 \times 10^{13}$ vg/kg, about $7 \times 10^{13}$ vg/kg, about $8 \times 10^{13}$ vg/kg, about $9 \times 10^{13}$ vg/kg, about $1 \times 10^{14}$ vg/kg, about $2 \times 10^{14}$ vg/kg, about $3 \times 10^{14}$ vg/kg, about $4 \times 10^{14}$ vg/kg or about $5 \times 10^{14}$ vg/kg based on a supercoiled DNA or plasmid as the quantitation standard.

In another embodiment, in any of the disclosed uses, the medicament comprises rAAV at a dose about $1.85 \times 10^{13}$ vg/kg or $7.41 \times 10^{13}$ vg/kg based on a linearized DNA or plasmid as the quantitation standard. For example, the medicament comprises rAAV at a dose of about $1.0 \times 10^{13}$ vg/kg to about $8.0 \times 10^{13}$ vg/kg, about $1.5 \times 10^{13}$ vg/kg to about $8.0 \times 10^{13}$ vg/kg, about $1.6 \times 10^{13}$ vg/kg to about $8.0 \times 10^{13}$ vg/kg, about $1.8 \times 10^{13}$ vg/kg to about $8.0 \times 10^{13}$ vg/kg, about $1.2 \times 10^{13}$ vg/kg to about $7.5 \times 10^{13}$ vg/kg, about $1.9 \times 10^{13}$ vg/kg to about $7.5 \times 10^{13}$ vg/kg, about $1.4 \times 10^{13}$ vg/kg to about $7.4 \times 10^{13}$ vg/kg, about $1.9 \times 10^{13}$ vg/kg to about $7.5 \times 10^{13}$ vg/kg, or about $1.8 \times 10^{13}$ vg/kg to about $8.0 \times 10^{13}$ vg/kg based on a linearized DNA or plasmid as the quantitation standard.

In addition, in any of the disclosed uses, the medicament is formulated for administration by an intravenous route. For example, in any of the disclosed uses, the medicament is formulated for administration by injection, infusion or implantation. In some embodiments, the medicament is formulated for administration by an intravenous route through a peripheral limb vein.

In any of the disclosed uses, the medicament is for the treatment of limb-girdle muscular dystrophy, such as limb-girdle muscular dystrophy type 2D (LGMD2D).

In an exemplary embodiment, the disclosure provides for use of a rAAV for the preparation of a medicament for treating limb-girdle muscular dystrophy, wherein the medicament is formulated for administration by intravenous infusion and the rAAV is at a dose of about $5 \times 10^{13}$ vg/kg to about $2 \times 10^{14}$ vg/kg based on a supercoiled DNA or plasmid as the quantitation standard, and wherein the rAAV comprises the scAAVrh74.tMCK.hSGCA construct nucleotide sequence of SEQ ID NO: 4. For example, administration of the medicament to a subject in need results in an increase in alpha-sarcoglycan gene expression in a cell of the subject as compared to the level of alpha-sarcoglycan gene expression before administration of the rAAV.

In any of the disclose uses, administration of the medicament to a subject in need results in an increase in the level of alpha-sarcoglycan gene expression in a cell of the subject as compared to the level of alpha-sarcoglycan gene expression before administration of the medicament; and/or administration of the medicament to a subject results in decrease in the serum CK level in the subject as compared to serum CK level before administration of the medicament; and/or wherein the locomotor activity and specific-force generation are increased; wherein fibrosis is reduced; wherein the resistance to contraction-induced injury in tibialis anterior muscle is increased; and/or administration of the medicament to the subject results in an increase in the number of alpha-sarcoglycan positive fibers in the muscle tissue of the subject is increased as compared to the number of alpha-sarcoglycan positive fibers before administration of the medicament, and/or administration of the medicament to the subject in need results in reduced fibrosis in the subject as compared to before administration of the medicament; and/or administration of the medicament results in an increase in the specific force, the fiber diameter size, and/or the eccentric contraction in the muscle of the subject as compared to before administration of the medicament. In some embodiments, the alpha-sarcoglycan gene expression is detected by measuring the alpha-sarcoglycan protein level by Western blot, and/or immunohistochemistry.

In another aspect, the disclosure provides for use of any of the disclosed rAAV for the preparation of a medicament for expressing alpha-sarcoglycan gene in a cell in a subject in need. For example, the disclosure provides for use of scAAVrh74.tMCK.hSGCA construct for the preparation of a medicament for expressing alpha-sarcoglycan gene in a cell in a subject in need, wherein the scAAVrh74.tMCK.hSGCA construct comprises a nucleotide sequence of SEQ ID NO: 4. In addition, in any of the uses, the expression of the alpha-sarcoglycan gene in the cell of the subject is detected by measuring the alpha-sarcoglycan protein level on a Western blot in muscle biopsies. Alternatively, in any of the uses, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for use of any of the disclosed rAAV for the preparation of medicament for decreasing a serum CK level in a subject in need thereof. For example, the disclosure provides for use of scAAVrh74.tMCK.hSGCA construct for the preparation of a medicament for decreasing a serum CK level in a subject in need thereof, wherein scAAVrh74.tMCK.hSGCA construct comprises the nucleotide sequence of SEQ ID NO: 4.

In another aspect, the disclosure provides for use of any of the disclosed rAAV for the preparation of a medicament for increasing alpha-sarcoglycan positive fibers in a muscle tissue of a subject. For example, the disclosure provides for use of scAAVrh74.tMCK.hSGCA construct for the preparation of a medicament for increasing alpha-sarcoglycan positive fibers in a muscle tissue of a subject, wherein scAAVrh74.tMCK.hSGCA construct comprises the nucleotide sequence of SEQ ID NO: 4.

The disclosure also provides for use any of the disclosed rAAV for the preparation of a medicament for increasing the expression of alpha-sarcoglycan in a subject in need thereof. For example, the disclosure provides for use of scAAVrh74.tMCK.hSGCA construct for the preparation of a medicament for increasing the expression of alpha-sarcoglycan in a subject in need thereof, wherein the scAAVrh74.tMCK.hSGCA construct comprises the nucleotide sequence of SEQ ID NO: 4. In addition, in any of the disclosed uses, the expression of the alpha-sarcoglycan gene in the cell of the subject is detected by measuring the alpha-sarcoglycan protein level on a Western blot in muscle biopsies. Alternatively, in any of the disclosed uses, expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

In any of the disclosed methods, compositions or uses, the subject is a human subject that is 4 to 15 years of age, or a human subject that is 25 to 55 years of age or a human subject that is over 50 years of age.

In any of the disclosed methods, compositions or uses, the subject is a pediatric subject, an adolescent subject or a young adult subject. Alternatively, the subject is a middle aged adult or elderly subject.

For example, in any of the disclosed methods, compositions or uses, the subject is a human subject that is 4-15 years of age, has a confirmed alpha-sarcoglycan (SGCA) mutation in both alleles, was negative for AAVrh74 antibodies and/or had >40% or normal 100 meter walk test.

In another aspect, the disclosure provides for methods of generating a rAAV administered in a method of any of the disclosed methods, compositions or uses, the method comprising transferring an AAV vector plasmid to a host cell, wherein the AAV vector plasmid comprises a nucleotide sequence that is at least 90%, 91%, 92%, 93%, 94%, 95%, 96%, 97%, 98%, or 99% identical to SEQ ID NO: 8. For example, the AAV vector plasmid comprises a nucleotide sequence of SEQ ID NO: 8. In some embodiments, the vector plasmid comprises a nucleotide sequence that is at least 90%, 91%, 92%, 93%, 94%, 95%, 96%, 97%, 98%, or 99% identical to SEQ ID NO: 1, 4, or 8, or the vector plasmid comprises a nucleotide sequence of SEQ ID NO: 1, 4, or 8.

In any of the disclosed methods of generating a rAAV, the method further comprises transferring a packaging plasmid and/or a helper virus to the host cell. In addition, in any of the disclosed methods of generating a rAAV, a packaging cell comprises a stably integrated AAV cap gene and/or comprises a packaging cell comprises a stably integrated AAV rep gene.

In another aspect, the disclosure provides for host cells comprising an AAV vector plasmid that comprises a nucleotide sequence that is at least 90%, 91%, 92%, 93%, 94%, 95%, 96%, 97%, 98%, or 99% identical to SEQ ID NO: 1, 4, or 8. For example, the host cell comprises an AAV vector plasmid that comprises a nucleotide sequence of SEQ ID NO: 1, 4, or 8.

BRIEF DESCRIPTION OF THE DRAWING

FIG. 9a shows improved muscle pathology. FIG. 9b shows reduction in central nucleation and increase in average fiber size in gastrocnemius (GAS) and triceps (TRI) muscles. FIG. 9c shows a reduction in levels of fibrosis compared to untreated controls. Abbreviations: TA, tibialis anterior; GAS, gastrocnemius; QD, quadricep; GLUT, gluteus; PSO, psoas major, TRI, tricep; diaphragm; WT, wild-type.

DETAILED DESCRIPTION

Figure 1:
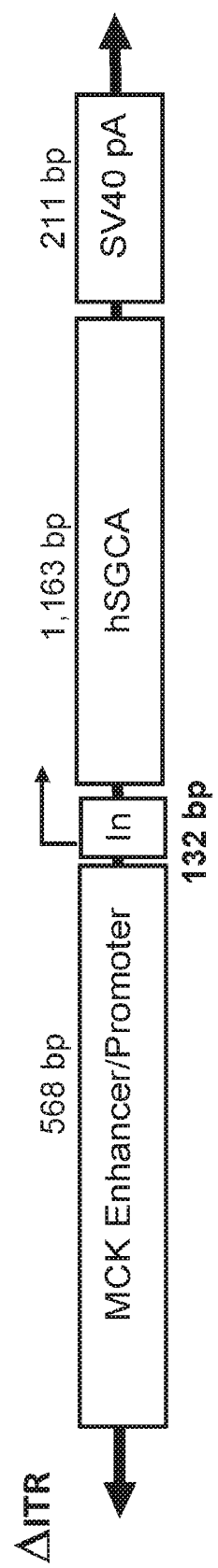
FIG. 1 shows the scAAVrh74.tMCK.hSGCA gene cassette.

The present disclosure is based on the discovery that administration of an rAAV comprising a polynucleotide expressing alpha-sarcoglycan results in a reduction or complete reversal of muscle fibrosis in a limb-girdle muscular dystrophy animal model. As demonstrated herein in the Examples, administration of the rAAV described herein resulted in the reversal of dystrophic features including reduced CK levels, increased muscle force, improved ambulation and vertical activity, and other motor functions.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); *Freshney Culture of Animal Cells, A Manual of Basic Technique* (Wiley-Liss, Third Edition); and Ausubel et al. (1991) *Current Protocols in Molecular Biology* (Wiley Interscience, N.Y.).

All publications, patents and patent applications cited herein, whether supra or infra, are hereby incorporated by reference in their entirety.

Definitions

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. Reference to "a recombinant AAV" includes a mixture of two or more rAAV virions, and the like. All technical and scientific terms used herein have the same meaning as commonly understood to one of ordinary skill in the art to which this invention belongs unless clearly indicated otherwise.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the statistical experimental error (standard deviation of error) for the device or method being employed to determine the value.

The term "vector" or "expression vector" is meant to be any genetic element, such as a plasmid, phage, transposon, cosmid, chromosome, virus, virion, etc., which is capable of replication when associated with the proper control elements and which can transfer gene sequences between cells. In one embodiment, the vector is a viral vector. Expression vectors can contain a variety of control sequences, structural genes (e.g., genes of interest), and nucleic acid sequences that serve other functions as well.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

The term "AAV vector" refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products. In one embodiment, the AAV vector is a vector derived from an adeno-associated virus serotype, including without limitation, AAV-1, AAV-2, AAV-3, AAV-4, AAV-5, AAV-6, AAV-7, AAV-8, AAV-9, AAV-10, AAV-11, AAV-12, AAV-13, AAV rh10, and AAV rh74. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

The term "AAV helper functions" refer to AAV-derived coding sequences that can be expressed to provide AAV gene products that, in turn, function in trans for productive AAV replication. Thus, AAV helper functions comprise the major AAV open reading frames (ORFs), reps and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

By "recombinant virus" is meant a virus that has been genetically altered, e.g., by the addition or insertion of a heterologous nucleic acid sequence into the viral particle.

By "AAV virion" "AAV viral particle" or "AAV vector particle" refers to a viral particle composed of at least one AAV capsid protein and an encapsidated polynucleotide AAV vector. The AAV virion, in one embodiment, comprises a heterologous polynucleotide (i.e. a polynucleotide other than a wild-type AAV genome such as a transgene to be delivered to a mammalian cell). Production of AAV viral particles, in some embodiment, includes production of AAV vector, as such a vector is contained within an AAV vector particle. If the particle comprises a heterologous polynucleotide (i.e. a polynucleotide other than a wild-type AAV genome such as a transgene to be delivered to a mammalian cell), it is typically referred to as an "rAAV vector" or simply "rAAV particle." Thus, production of AAV vector particle necessarily includes production of rAAV, as such a rAAV genome is contained within an rAAV vector particle.

For example, a wild-type (wt) AAV virus particle comprising a linear, single-stranded AAV nucleic acid genome associated with an AAV capsid protein coat. The AAV virion can be either a single-stranded (ss) AAV or self-complementary (SC) AAV. In one embodiment, a single-stranded AAV nucleic acid molecules of either complementary sense, e.g., "sense" or "antisense" strands, can be packaged into a AAV virion and both strands are equally infectious.

The term "recombinant AAV," or "rAAV" is defined herein as an infectious, replication-defective virus composed of an AAV protein shell, encapsidating a heterologous nucleotide sequence of interest which is flanked on both sides by AAV ITRs. A rAAV, in one embodiment, is produced in a suitable host cell which has an AAV vector, AAV helper functions and accessory functions introduced therein. In this manner, the host cell is capable of encoding AAV polypeptides that are required for packaging the AAV vector (containing a recombinant nucleotide sequence of interest) into infectious recombinant virion particles for subsequent gene delivery.

The term "transfection" refers to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a nucleotide integration vector and other nucleic acid molecules, into suitable host cells.

The term "transduction" denotes the delivery of a DNA molecule to a recipient cell either in vivo or in vitro, via a replication-defective viral vector, such as via a recombinant AAV virion.

The term "host cell" denotes, for example, microorganisms, yeast cells, insect, cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The nucleic acids include base analogues of DNA and RNA including, but not limited to 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters." In one embodiment, the promoter is a muscle-specific promoter, which includes but is not limited to, a human skeletal actin gene element, a cardiac actin gene element, a desmin promoter, a skeletal alpha-actin (ASKA) promoter, a troponin I (TNNI2) promoter, a myocyte-specific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, and a glucocorticoid response element (gre). In another embodiment, the promoter is an MCK promoter, a tMCK promoter, or an MHCK7 promoter.

The term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A promoter "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA, at least one multiple cloning site, and a "mammalian" origin of replication (e.g., a SV40 or adenovirus origin of replication).

By "isolated" when referring to a nucleotide sequence, is meant that the indicated molecule is present in the substantial absence of other biological macromolecules such as other nucleotide sequences, chromatin material, etc. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3," or "5" relative to another sequence, it is to be understood that it is the position of the sequences in the "sense" or "coding" strand of a DNA molecule that is being referred to as is conventional in the art.

The terms "sequence identity", "percent sequence identity", or "percent identical" in the context of nucleic acid or amino acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. The percentage identity of the sequences can be determined by techniques known in the art. For example, homology can be determined by a direct comparison of the sequence information between two polypeptide molecules by aligning the sequence information and using readily available computer programs such as ALIGN, ClustalW2 and BLAST. In one embodiment, when BLAST is used as the alignment tool, the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

The term "subject" refers to any member of the animal kingdom, which includes, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. In some embodiments, the subject is a human ranging in age from birth to 2 years, from 1 to 10 years, or ranging from 4 to 15 years, or ranging from 10 to 19 years, or from 20 to 40 years of age, or from 15 to 29 years of age or from 25-55 years, or ranging from 40 to 60 years, or over 50 years or over 60 years or over 65 years or over 70 years. For example, the subject is a human child (2 to 12 years), a human adolescent (10 to 19 years). In some embodiments, the subject is an adult human (18 years or older). In particular, the subject is a young adult human (15 to 29 years of age), middle aged adult human (25 to 55 year of age) or an older adult human (over 50 years of age) or elderly human subject (over 65 years of age) or a geriatric human subject (over 70 years of age).

By "therapeutic effect" is meant any therapeutic benefit conferred by the treatment described herein. For example, such an effect can be sustained expression, in an appropriate target tissue, of a protein or an enzyme which is deficient or missing in the muscular dystrophy of interest. Additionally, a therapeutic effect may be any reduction or elimination of one or more clinical or subclinical manifestations of the disease or disorder of interest. For example, a reduction in the CK level, reduction in fibrosis is reduced; an increase in the resistance to contraction-induced injury in tibialis anterior muscle; and/increased specific force in the muscle, and improved motor function provides a therapeutic benefit to the treated subject with LGMD-2D.

In another aspect, a recombinant AAV vector described herein comprises a polynucleotide sequence encoding alpha-sarcoglycan that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 2, or a protein retains α-sarcoglycan activity. In another embodiment, the alpha-sarcoglycan comprises a polypeptide sequence set forth in SEQ ID NO: 2.

In another aspect, described herein is a recombinant AAV vector comprising a polynucleotide sequence encoding functional alpha-sarcoglycan that comprises a nucleotide sequence that hybridizes under stringent conditions to the nucleic acid sequence at least 90%, 91%, 92%, 93%, 94%, 95%, 96%, 97%, 98%, or 99% identical to SEQ ID NO: 1, or a complement thereof. In another embodiment, the rAAV comprises a nucleotide sequence with at least 90%, 91%, 92%, 93%, 94%, 95%, 96%, 97%, 98%, or 99% identity to SEQ ID NO: 4. In another embodiment, the rAAV comprises a nucleotide sequence of SEQ ID NO: 1 or SEQ ID NO: 4.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

When ranges are used herein for physical properties, such as molecular weight, concentration, or dosage, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

Limb-girdle muscular dystrophy type 2D (LGMD2D) is a progressive muscular dystrophy that manifests with muscle weakness, respiratory abnormalities, and in rare cases cardiomyopathy. LGMD2D is caused by mutations in the alpha-sarcoglycan gene resulting in loss of protein and concomitant loss of the sarcoglycan and dystrophin-associated glycoprotein complex. The Sgca-null (sgca$^{-/-}$) mouse recapitulates the clinical phenotype of patients with LGMD2D, including dystrophic features such as muscle necrosis and fibrosis, elevated serum creatine kinase (CK), and reduction in generation of absolute muscle force and locomotor activity. Thus, sgca$^{-/-}$ mice provide a relevant model to test the safety and efficacy of gene replacement. Hereby, this disclosure provides a self-complementary AAVrh74 vector containing a codon-optimized full-length human SGCA (hSGCA) transgene driven by a muscle-specific promoter, truncated muscle creatine kinase (tMCK). The efficacy and safety of scAAVrh74.tMCK.hSGCA in sgca$^{-/-}$ mice were tested using a dose-escalation design to evaluate a single systemic injection of $1\times10^{12}$, $3\times10^{12}$, and $6\times10^{12}$ vg compared to vehicle-treatment and wild-type mice. In sgca$^{-/-}$ mice treatment with scAAVrh74.tMCK.hSGCA resulted in robust protein expression of α-SG at the sarcolemma membrane in skeletal muscle at all doses tested. Additionally, scAAVrh74.tMCK.hSGCA was effective in improving the histopathology of limb and diaphragm muscle of sgca$^{-/-}$ mice, as indicated by reductions in fibrosis and central nucleation and normalization of myofiber size. These molecular changes were concomitant with significant increases in specific force generation in the diaphragm and tibialis anterior muscle, protection against eccentric force loss, and reduction in serum CK. Locomotor activity was improved at all doses of vector-treated compared to vehicle-treated sgca$^{-/-}$ mice. Lastly, a lack of vector-associated toxicity was detected in a serum chemistry panel and by gross necropsy. Collectively, the study provides support for a systemic delivery of scAAVrh74.tMCK.hSGCA in a clinical setting for the treatment of LGMD2D.

In another aspect, the recombinant AAV vectors described herein may be operably linked to a muscle-specific control element. For example, the muscle-specific promoter comprises one or more of a human skeletal actin gene element, a cardiac actin gene element, a desmin promoter, a skeletal alpha-actin (ASKA) promoter, a troponin I (TNNI2) promoter, a myocyte-specific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, and a glucocorticoid response element (gre).

In one embodiment, the muscle-specific promoter is a tMCK promoter, which comprises a sequence of SEQ ID NO: 3. An exemplary rAAV described herein is AAVrh74.tMCK.SGCA which comprises a nucleotide sequence of SEQ ID NO: 4. In some embodiments, the polynucleotide sequence encoding a AAVrh74.tMCK.SGCA comprises a sequence at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or at least 99% identical to the nucleotide sequence set forth in SEQ ID NO: 4, or to a nucleotide sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or at least 99% identical to SEQ ID NO: 1.

In another embodiment, the polynucleotide sequence encoding a AAVrh74.tMCK.SGCA comprises a nucleotide sequence that encodes a polypeptide sequence at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or at least 99% identical to the nucleotide sequence set forth in SEQ ID NO: 1. In some embodiments, the polynucleotide sequence encodes a protein that retains the alpha-sarcoglycan activity.

In one embodiment, the rAAV comprises a 5' inverted terminal repeat sequence of SEQ ID NO: 5. In another embodiment, the rAAV comprises a 3' inverted terminal repeat sequence of SEQ ID NO: 6. In some embodiments, the rAAV comprises a poly A sequence of SEQ ID NO: 7.

The AAV can be any serotype, for example AAV1, AAV2, AAV3, AAV4, AAV5, AAV6, AAV7, AAV8, AAV9, AAV-10, AAV-11, AAV-12, AAV-13, AAV rh.10, AAV rh.74, or variants and derivatives thereof. In one embodiment, the rAAV is of the serotype AAVrh.74. Production of pseudotyped rAAV is disclosed in, for example, WO 2001/083692, which is incorporated by reference in its entirety. Other types of rAAV variants, for example rAAV with capsid mutations, are also contemplated. See, for example, Marsic et al., Molecular Therapy, 22(11): 1900-1909 (2014).

Compositions comprising any of the rAAV vectors described herein are also contemplated.

Provided are methods of treating muscular dystrophy in a human subject in need thereof comprising the step of administering a recombinant adeno-associated virus (rAAV) scAAVrh74.tMCK.hSGCA, wherein the rAAV is administered using at a dose of about $1.0\times10^{12}$ vg/kg to about $5.0\times10^{15}$ vg/kg. For example, in any of the provided methods, the dose of the rAAV administered is between about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $5\times10^{13}$ vg/kg to about $2\times10^{14}$ vg/kg, or about $2.0\times10^{13}$ vg/kg to about $3.0\times10^{14}$ vg/kg. In another embodiment, the dose is about $5.0\times10^{13}$ vg/kg, $1.0\times10^{14}$ vg/kg, or $2.0\times10^{14}$ vg/kg. In one embodiment, the rAAV is administered by a systemic route, which comprises an intravenous route. In another embodiment, the rAAV is administered intravenously at a dose of about $5.0\times10^{13}$ vg/kg, $1.0\times10^{14}$ vg/kg, or $2.0\times10^{14}$ vg/kg. In one embodiment, the muscular dystrophy is limb-girdle muscular dystrophy.

In addition, the dose of the rAAV administered is about $1.5\times10^{13}$ vg to about $3.5\times10^{16}$ vg, or $3\times10^{13}$ vg to $1\times10^{16}$ vg, or about $1.5\times10^{13}$ vg to about $2\times10^{15}$ vg, or about $1.5\times10^{13}$ vg to about $1\times10^{15}$ vg. In addition, in any of the methods, the dose of rAAV is administered at a concentration of about 10 mL/kg. In one embodiment, the muscular dystrophy is limb-girdle muscular dystrophy. In one embodiment, the muscular dystrophy is limb-girdle muscular dystrophy, type 2D. The doses in this disclosure, expressed in either vg or vg/kg, are based on a titration qualification method by quantitative PCR (qPCR). The qPCR-based titration method is known in the art.

In addition, provided are methods of treating muscular dystrophy in a subject in need thereof comprising the step of administering a recombinant adeno-associated virus (rAAV) scAAVrh74.tMCK.hSGCA, wherein the rAAV is administered using a systemic route of administration and at a dose of about $1.0\times10^{12}$ vg/kg to about $2.0\times10^{15}$ vg/kg; wherein the level of alpha-sarcoglycan gene expression in a cell of the subject is increased after administration of the rAAV as compared to the level of alpha-sarcoglycan gene expression before administration of the rAAV; wherein the serum CK level in the subject is decreased after administration of the rAAV as compared to serum CK level before administration of the rAAV; and/or wherein the locomotor activity and specific-force generation are increased; wherein fibrosis is reduced; wherein the resistance to contraction-induced injury in tibialis anterior muscle is increased; and/wherein the number of alpha-sarcoglycan positive fibers in the muscle tissue of the subject is increased after administration of the rAAV as compared to the number of alpha-sarcoglycan positive fibers before administration of the rAAV; wherein the fiber diameter size in the muscle tissue of the subject is increased after administration of the rAAV as compared to the number of the fiber diameter before administration of the rAAV; or wherein the central nucleation in the muscle tissue of the subject is reduced after administration of the rAAV as compared to the central nucleation before administration of the rAAV. The muscle tissues include but are not limited to triceps, tibialis anterior, soleus, gastrocnemius, biceps, trapezius, gluteus, psoas major, deltoids, quadriceps, and diaphragm. In one embodiment, the muscle tissues comprise tibialis anterior, gastrocnemius, gluteus, psoas major, and triceps. The expression of alpha-sarcoglycan is determined by methods known to a person with ordinary skill in the art. In one embodiment, the expression is determined by Western blot, immunochemistry in muscle biopsies, and/or by detecting the number of vector genome per microgram of genomic DNA.

In some embodiments, the disclosure includes a method of treating muscular dystrophy in a subject in need thereof comprising the step of administering a recombinant adeno-associated virus (rAAV) scAAVrh74.tMCK.hSGCA, wherein motor function is demonstrably improved in said human subject as compared to motor function of said human subject before administration of the rAAV.

Provided are methods of increasing alpha-sarcoglycan in a patient in need thereof comprising administering to the patient the scAAVrh74.tMCK.hSGCA construct nucleotide sequence of SEQ ID NO: 4.

In any of the methods, uses and compositions of treating muscular dystrophy provided, the subject is 4-15 years of age, has confirmed alpha-sarcoglycan (SGCA) mutation in both alleles, is negative for AAVrh74 antibodies and/or had >40% or normal 100 meter walk test. In any of the methods, uses and compositions of treating muscular dystrophy provided, the subject is a pediatric subject. In some embodiments, the subject is a pediatric subject, such as a subject ranging in age from 1 to 21 years. In some embodiments, the subject is 1 to 10 years of age, or 2 to 12 years of age, 4 to 15 years of age, or 10 to 19 years of age. The subject, in one embodiment, is an adolescent subject, such as a subject ranging in age from 12 to 21 years. In addition, the subject, in one embodiment, is a young adult subject such as a subject ranging in age from 15 to 29 years of age or 18-39 years of age. In some embodiment, the subject is a middle-aged adult or an elderly subject, such that the middle-aged adult may range in age from 25-55 years of age, the older adult subject may range in age over 50 years of age, and the elderly subject may range in age over 65 years of age. In some embodiments, the rAAV is administered by injection, infusion or implantation. For example, the rAAV is administered by infusion over approximately 1 to 2 hours. In addition, the rAAV is administered by an intravenous route through a peripheral limb vein.

In the methods of treating muscular dystrophy in a human subject in need thereof comprising the step of administering a recombinant adeno-associated virus (rAAV) scAAVrh74.tMCK.hSGCA, wherein the rAAV is administered using a systemic route of administration and at a dose of about $1.0 \times 10^{12}$ vg/kg to about $5.0 \times 10^{14}$ vg/kg and the rAAV comprises a nucleotide sequence at least 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 1. In another embodiment, the rAAV comprises a nucleotide sequence set forth in SEQ ID NO: 1. In one embodiment, the rAAV encodes a protein comprising a polypeptide sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 2. In another embodiment, the rAAV comprises a nucleotide sequence encoding a protein comprising a polypeptide sequence set forth in SEQ ID NO: 2. In addition, the any of the disclosed rAAV comprise a promoter such as the tMCK promoter sequence of SEQ ID NO: 3. In some embodiments, the rAAV is of the serotype AAVrh.74. In addition, the rAAV comprises the scAAVrh74.tMCK.hSGCA construct nucleotide sequence of SEQ ID NO: 3. In on embodiment, the rAAV comprises a 5' inverted terminal repeat sequence of SEQ ID NO: 5. In another embodiment, the rAAV comprises a 3' inverted terminal repeat sequence of SEQ ID NO: 6. In another embodiment, the rAAV comprises a poly A sequence of SEQ ID NO: 7.

AAV dosage can be determined by multiple methods, which include but are not limited to LISA, assessment of the reverse transcriptase activity, FACS, transduction assays northern blotting (e.g., semi-quantitative northern), dot blot analysis or PCR (e.g., qPCR). It is well known that the AAV doses can be determined by measuring AAV vector genomes with quantitative real-time PCR (qPCR). Such qPCR methods overcome the inconsistency or arbitrary results from conventional transduction assays. In one embodiment of PCR dosage determination, plasmid DNA is used as a calibration standard. The forms of the plasmids can impact the dosage results from the qPCR methods. In one embodiment, the circular or supercoiled DNA or plasmids are used as a quantification standard. In another embodiment, the linearized DNA or plasmids are used as the quantification standard.

The term "supercoiled DNA" or "supercoiled plasmid" refers to a DNA or plasmid that comprises no free end. The term "linearized DNA" or linearized plasmid" refer to a DNA or plasmid that comprises a free 5' end and a free 3' end, which are not linked to each other. In one embodiment, a linearized DNA or plasmid is obtained by a restriction digest of a circular DNA (e.g. plasmid DNA) or by a restriction digest of a dbDNA. In another embodiment, the restriction digest is performed using enzymes that generate at least one blunt end.

In an exemplary embodiment, methods of treating muscular dystrophy in a human subject in need thereof comprise the step of administering a recombinant adeno-associated virus (rAAV) scAAVrh74. tMCK7.hSGCA, wherein the rAAV is administered using a systemic route of administration and at a dose of about $1.0 \times 10^{12}$ vg/kg to about $5.0 \times 10^{14}$ vg/kg, wherein the human subject is suffering from limb-girdle muscular dystrophy. In one embodiment, the rAAV is administered by intravenous infusion over approximately 1 to 2 hours at a dose of about $5.0 \times 10^{13}$ vg/kg, $1.0 \times 10^{14}$ vg/kg, or $2.0 \times 10^{14}$ vg/kg based on a supercoiled DNA or plasmid as the quantitation standard, and wherein the rAAV comprises the scAAVrh74. tMCK7.hSGCA construct nucleotide sequence of SEQ ID NO: 3. In another embodiment, the dose is about $1.85 \times 10^{13}$ vg/kg or $7.41 \times 10^{13}$ vg/kg based on a linearized DNA or plasmid as the quantitation standard.

The disclosure also provides a method of increasing sarcoglycan expression in muscle tissue of a subject comprising administering to the subject a scAAVrh74.tMCK.hSGCA construct comprising a nucleotide sequence at least 90% identical, at least 95% identical, or 99% identical to SEQ ID NOs: 1, and/or 4.

The disclosure further provides a method of improving muscle function of a subject comprising administering to the subject a construct comprising a nucleotide sequence at least 90% identical, at least 95% identical, or 99% identical to SEQ ID NO: 1, and/or 4.

In some aspects, the subject suffers from a genetic mutation in a gene encoding a sarcoglycan protein or a muscular dystrophy. In some aspects, the subject suffers from a genetic mutation in a gene encoding alpha-sarcoglycan protein.

In any of the provided methods, the level of alpha-sarcoglycan gene expression in a cell of the subject is increased after administration of scAAVrh74.tMCK 7.hSGCA construct as compared to the level of alpha-sarcoglycan gene expression before administration of scAAVrh74.tMCK.hSGCA construct.

In addition, in any of the provided methods, the expression of the alpha-sarcoglycan gene in the cell is detected by measuring the alpha-sarcoglycan protein level on a Western blot or immunohistochemistry in muscle biopsied before and after administration of scAAVrh74.tMCK.hSGCA construct.

In any of the provided methods, the level of alpha-sarcoglycan protein is increased after administration of scAAVrh74.tMCK.hSGCA construct. For example, the level of the level of alpha-sarcoglycan protein is increased by at least 33% as detected by measuring the alpha-sarcoglycan protein level on a Western blot in muscle biopsied before and after administration of scAAVrh74.tMCK.hSGCA construct, or the level of alpha-sarcoglycan protein is measured by immunohistochemistry in muscle biopsies and/or by detecting the number of vector genome per microgram of genomic DNA before and after administration of scAAVrh74.tMCK.hSGCA construct.

In any of the methods provided herein, the serum CK level in the subject is decreased after administration of scAAVrh74.tMCK.hSGCA construct as compared to serum CK level before administration of scAAVrh74.tMCK.hSGCA construct.

In any of the methods provided herein, the number of alpha-sarcoglycan positive fibers in the muscle tissue of the subject is increased after administration of scAAVrh74.tMCK.hSGCA construct as compared to the number of alpha-sarcoglycan positive fibers before administration of scAAVrh74.tMCK.hSGCA construct. For example, the number of alpha-sarcoglycan positive fibers is detected by measuring the alpha-sarcoglycan protein level by Western blot or immunohistochemistry on muscle biopsies before and after administration of scAAVrh74.tMCK.hSGCA construct. For example, the number of alpha-sarcoglycan positive fibers in the muscle tissue of the subject is increased after administration of scAAVrh74.tMCK.hSGCA construct.

In any of the methods provided herein, the level of alpha-sarcoglycan in the subject is increased after administration of the rAAV as compared to the level of alpha-sarcoglycan before administration of scAAVrh74.tMCK.hSGCA construct. The level of alpha-sarcoglycan is detected by measuring the alpha-sarcoglycan protein level by immunohistochemistry or Western blot on muscle biopsies before and after administration of scAAVrh74.tMCK.hSGCA construct.

Another embodiment provides for methods expressing alpha-sarcoglycan gene in a patient cell comprising administering to the patient the scAAVrh74.tMCK.hSGCA construct nucleotide sequence of SEQ ID NO: 4. In any of the provided methods of expressing alpha-sarcoglycan gene in a patient cell, expression of the alpha-sarcoglycan gene in the patient cell is detected by measuring the alpha-sarcoglycan protein level on a Western blot or immunohistochemistry in muscle biopsies before and after administration of the scAAVrh74.tMCK.hSGCA construct. In one embodiment, the alpha-sarcoglycan gene is measured in the patient by detecting greater than one rAAV vector genome copy per nucleus. In another embodiment, the expression of the alpha-sarcoglycan gene is measured in the subject by detecting the number of vector genome per microgram of genomic DNA.

Methods of decreasing serum CK levels in a patient in need thereof, the method comprising administering to the subject the scAAVrh74.tMCK.hSGCA construct nucleotide sequence of SEQ ID NO: 4 are also provided.

Methods of increasing alpha-sarcoglycan positive fibers in a patient muscle tissue comprising administering to the subject the scAAVrh74.tMCK.hSGCA construct nucleotide sequence of SEQ ID NO: 4 are provided. In any of these methods, the number of alpha-sarcoglycan positive fibers is detected by measuring the alpha-sarcoglycan protein level by Western blot or immunohistochemistry on muscle biopsies before and after administration of the rAAV.

Another embodiment provides for methods of increasing the expression of alpha-sarcoglycan in a subject in need thereof comprising administering to the subject the scAAVrh74.tMCK.hSGCA construct nucleotide sequence of SEQ ID NO: 4. In any of these methods, the level of alpha-sarcoglycan is detected by measuring the alpha-sarcoglycan protein level by Western blot or immunohistochemistry on muscle biopsies before and after administration of the rAAV.

Methods of producing a recombinant AAV vector particle comprising culturing a host cell that is transferred with any recombinant AAV vector described herein and recovering recombinant AAV particles from the supernatant of the transfected cells are also provided. Viral particles comprising any of the recombinant AAV vectors described herein are also contemplated. In one embodiment, the method of generating the rAAV comprising transferring an AAV vector plasmid to a host cell. In another embodiment, the recombinant AAV vector particle and/or the AAV vector plasmid comprises a nucleotide sequence that is at least about 65%, about 70%, about 75%, about 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% or more identical to SEQ ID NO: 8. In another aspect, the disclosure provides a host cell that comprising an AAV vector plasmid that comprises a nucleotide sequence of SEQ ID NO: 8. In some embodiment, the AAV vector plasmid is stably expressed in the host cell. The host cell stably harboring the AAV vector plasmid can be used to generate rAAV. In one embodiment, the AAV vector plasmid is a pAAV.tMCK.hSGCA. KAN plasmid (SEQ ID NO: 8).

Methods of reducing fibrosis in a mammalian subject in need thereof is also provided. In this regard, the method comprises administering a therapeutically effective amount of an AAV vector described herein (or composition comprising an AAV vector described herein) to the mammalian subject. In some embodiments, the mammalian subject suffers from muscular dystrophy. In one embodiment, the muscular dystrophy is LGMD2D. In some embodiments, administration of an AAV vector described herein (or composition comprising an AAV vector described herein) reduces fibrosis in the muscle tissue of the subject. In one embodiment, the muscle tissue comprises psoas major, diaphragm, triceps, and/or gluteus.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 2I muscular dystrophy, limb-girdle type 2I muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject us suffering from limb-girdle muscular dystrophy type 2D (LGMD2D).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing alpha-sarcoglycan positive fibers in a muscle tissue, fiber diameter size, eccentric contraction in the muscle, muscular force and/or expression of alpha-sarcoglycan in a mammalian subject comprising administering a therapeutically effective amount of an AAV vector described herein (or composition comprising an AAV vector described herein) to the mammalian subject. Also described herein is a method of reducing fibrosis, central nucleation, CK level, and/or collage deposition in a subject comprising administering a therapeutically effective amount of an AAV vector described herein (or composition comprising an AAV vector described herein) to a subject.

In any of the methods of the invention, the subject may be suffering from muscular dystrophy such as limb-girdle muscular dystrophy or any other dystrophin-associated muscular dystrophy. In one embodiment, the muscular dystrophy is LGMD-2D.

Also provided is a method of treating muscular dystrophy in a mammalian subject comprising administering a therapeutically effective amount of an AAV vector described herein (or composition comprising an AAV vector described herein) to the mammalian subject. In some embodiments, the muscular dystrophy is limb-girdle muscular dystrophy.

In any of the methods of the invention, the rAAV is administered by intramuscular injection or intravenous injection. In addition, in any of the method of the invention, the rAAV is administered systemically, such as parental administration by injection, infusion or implantation.

The compositions of the invention are formulated for intramuscular injection or intravenous injection. In addition, the compositions of the invention are formulated for systemic administration, such as parental administration by injection, infusion or implantation.

In addition, any of the compositions formulated for administration to a subject suffering from muscular dystrophy (such as limb-girdle muscular dystrophy or any other dystrophin-associated muscular dystrophy). In some embodiments, the composition may further comprise a second recombinant AAV vector that expressed alpha-sarcoglycan or a second recombinant AAV vector comprising a polynucleotide sequence set forth in SEQ ID NO: 1 or SEQ ID NO: 4.

In any of the uses of the invention, the medicament is formulated for intramuscular injection or intravenous injection. In addition, in any of the uses of the invention, the medicament is formulated for systemic administration, such as parental administration by injection, infusion or implantation. In addition, any of the medicaments may be prepared for administration to a subject suffering from muscular dystrophy (such as limb-girdle muscular dystrophy or any other dystrophin associated muscular dystrophy). In some embodiments, the medicament may further comprise a second recombinant AAV vector that expressed alpha-sarcoglycan or a second recombinant AAV vector comprising a polynucleotide sequence in SEQ ID NO: 1 or SEQ ID NO: 4.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692. Other types of rAAV variants, for example rAAV with capsid mutations, are also contemplated.

DNA plasmids of the invention comprise rAAV genomes. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV rh10, and AAV rh.74. Production of pseudotyped rAAV is disclosed in, for example, WO 2001/083692, which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV named pAAV.tMCK.hSGCA which comprises the polynucleotide sequence set forth in SEQ ID NO: 3.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions described herein comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-formig counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg) as measured by qPCR.

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy. Thus, provided is a method of transducing a target cell with an rAAV scAAVrh74.tMCK.hSGCA, which comprises a nucleotide sequence of SEQ ID NO: 4.

In another embodiment, the disclosure provides a method of generating the rAAV scAAVrh74.tMCK.hSGCA which comprises transferring an AAV vector plasmid to a host cell. The methods of transferring a DNA to a host cell are well known in the art, which include but are not limited to transfection, infection, transformation, electroporation, and transduction. In one embodiment, the vector plasmid comprises a nucleotide sequence that is at least about 65%, about 70%, about 75%, about 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% or more identical to SEQ ID NO: 8. In another embodiment, the vector plasmid comprises a nucleotide sequence that is at least 90%, 95%, or 99% identical to SEQ ID NO: 8. In another embodiment, the vector plasmid comprises a nucleotide sequence of SEQ ID NO: 8. In another aspect, the disclosure provides a host cell that comprising an AAV vector plasmid that comprises a nucleotide sequence of SEQ ID NO: 8. In some embodiment, the AAV vector plasmid is stably expressed in the host cell. The host cell stably harboring the AAV vector plasmid can be used to generate rAAV. In one embodiment, the AAV vector plasmid is a pAAV.tMCK.hSGCA. KAN plasmid.

In one embodiment, the vector plasmid comprises a nucleotide sequence that is at least about 65%, about 70%, about 75%, about 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% or more identical to SEQ ID NO: 1, 4, or 8.

In one embodiment, the vector plasmid comprises a nucleotide sequence that is at least about 90%, 95%, or 99% identical to SEQ ID NO: 1, 4, or 8. In one embodiment, the vector plasmid comprises a nucleotide sequence of SEQ ID NO: 1, 4, or 8. The method of generating rAAV, in one embodiment, further comprises transferring a packaging plasmid and/or a helper virus to the host cell. In the packaging plasmid, in some embodiments, comprises an AAV rep and/or cap gene that is operably linked to a promoter. The promoter, in one embodiment, is an AAV transcription promoter. In one embodiment, the host cell is a packaging cell. In one embodiment, the packaging cell comprises a stably integrated AAV cap gene. In another embodiment, the packaging cell comprises a stably integrated AAV rep gene.

As used herein, the term "host cell" refers to a cell that can be used to express an exogenous DNA sequence. Non-limiting examples of a host cell comprise a microorganism, a yeast cell, an insect cell, and/or a mammalian cell. The host cell can be used as a recipient for an AAV helper construct, a packaging plasmid, an AAV vector plasmid, an accessary function vector, or other DNA. The term as used here encompasses the progeny of the original cell after expressing the exogenous DNA sequence in the original host cell. Non-limiting examples of host cells for AAV production include Sf9 insect cells and HEK 293T cells. The AAV vector plasmid can be introduced to the host cells, e.g., Sf9 or 293T, by infection (virus or baculovirus), transient transfection using reagents (e.g., liposomal, calcium phosphate) or physical means (e.g., electroporation), or other means know in the art. In another embodiment, the host cell lines are stably integrated with the rAAV plasmids into their genomes. Such stable cell lines can be established by incorporating a selection marker into the vector plasmid. In one embodiment, the host cell is a packaging cell for production of AAV viral particles. Thus, in another aspect, the disclosure provides a host cell that comprises an AAV vector plasmid that comprises a nucleotide sequence that is at least 90%, 95%, or 99% identical to SEQ ID NO: 8. In one embodiment, the AAV vector plasmid that comprises a nucleotide sequence of SEQ ID NO: 8. In another embodiment, the host cell comprises a nucleotide sequence of SEQ ID NO: 1, 4, or 8.

Combination therapies are also contemplated by the invention. Combination as used herein includes both simultaneous treatment or sequential treatments. Combinations of methods of the invention with standard medical treatments (e.g., steroids, corticosteroids, and/or glucocorticoids including but not limited to one or more of prednisone, prednisolone; and deflazacort) are specifically contemplated, as are combinations with novel therapies. In this regard, the combinations include administering to a subject one or more steroids, corticosteroids, and/or glucocorticoids including but not limited to one or more of prednisone, prednisolone; and deflazacort before administering an rAAV of the inventive methods to the subject, simultaneously with administering the rAAV to the subject, or after administering the rAAV to the subject.

In related embodiments of a combination therapy contemplated by the invention, the glucocorticoid includes, but is not limited to beclomethasone, betamethasone, budesonide, cortisone, dexamethasone, hydrocortisone, methylprednisolone, or triamcinolone.

It is recognized that an antigen specific T-cell response may occur in a subject administered with the rAAV vector. This is an expected response between 2-4 weeks following gene transfer. One possible consequence to such antigen specific T-cell responses is clearance of the transduced cells and loss of transgene expression. To dampen the host immune response to the rAAV based therapy, before the therapy, for example, twenty-four hours prior to the therapy procedure, subjects can be started on approximately 1 mg/kg/day prophylactic prednisone or comparable glucocorticoid by mouth with a maximum dose of 60 mg/day. IV administration of a comparable glucocorticoid at the approximate dose of 1 mg/kg/day would also be allowable if needed. Treatment will continue for approximately one month. A tapering protocol for prednisone or comparable glucocorticoid can be implemented based on individual subjects' immune response to the gene transfer, assessed by ELISpot assay and also by liver function monitoring with GGT.

A therapeutically effective amount of the rAAV vector is a dose of rAAV ranging from between about $1.0 \times 10^{12}$ vg/kg to about $2.0 \times 10^{15}$ vg/kg, about $5 \times 10^{12}$ vg/kg to about $1.0 \times 10^{15}$ vg/kg, about $1.0 \times 10^{13}$ vg/kg to about $5.0 \times 10^{14}$ vg/kg, about $5 \times 10^{13}$ vg/kg to about $2 \times 10^{14}$ vg/kg, or about $2.0 \times 10^{13}$ vg/kg to about $3.0 \times 10^{14}$ vg/kg. In another embodiment, the dose is about $5.0 \times 10^{13}$ vg/kg, about $1.0 \times 10^{14}$ vg/kg, or about $2.0 \times 10^{14}$ vg/kg. In another embodiment, the dose is $5.0 \times 10^{13}$ vg/kg, $1.0 \times 10^{14}$ vg/kg, or $2.0 \times 10^{14}$ vg/kg. The invention is also contemplated to include compositions comprising these ranges of rAAV vector.

Dosages may also be expressed in units of viral genomes (vg). The titers of rAAV may be determined by the supercoiled DNA or plasmid quantitation standard or the linearized DNA or plasmid quantitation standard. The titer or dosage of AAV vectors can vary based on the physical forms of plasmid or DNA as a quantitation standard. For example, the value of titer or dosage may vary based off of a supercoiled standard qPCR titering method or a linear standard qPCR titering method. In one embodiment, the dosage in this disclosure is based on a supercoiled DNA or plasmid as the quantitation standard. In another embodiment, the dosage in this disclosure is based on a linearized DNA or plasmid as the quantitation standard. Therefore, in one embodiment, the therapeutically effective amount of the rAAV vector is a dose of rAAV ranging from between about $1.0 \times 10^{12}$ vg/kg to about $2.0 \times 10^{15}$ vg/kg, about $5 \times 10^{12}$ vg/kg to about $1.0 \times 10^{15}$ vg/kg, about $1.0 \times 10^{13}$ vg/kg to about $5.0 \times 10^{14}$ vg/kg, about $5 \times 10^{13}$ vg/kg to about $2 \times 10^{14}$ vg/kg, or about $2.0 \times 10^{13}$ vg/kg to about $3.0 \times 10^{14}$ vg/kg based on a supercoiled DNA or plasmid as the quantitation standard. In another embodiment, the dose is about $5.0 \times 10^{13}$ vg/kg, about $1.0 \times 10^{14}$ vg/kg, or about $2.0 \times 10^{14}$ vg/kg based on a supercoiled DNA or plasmid as the quantitation standard. In another embodiment, the dose is $5.0 \times 10^{13}$ vg/kg, $1.0 \times 10^{14}$ vg/kg, or $2.0 \times 10^{14}$ vg/kg based on a supercoiled DNA or plasmid as the quantitation standard.

In another embodiment, the therapeutically effective amount of the rAAV vector is a dose of rAAV ranging from between about $1.0 \times 10^{13}$ vg/kg to about $8.0 \times 10^{13}$ vg/kg, about $1.5 \times 10^{13}$ vg/kg to about $8.0 \times 10^{13}$ vg/kg, about $1.6 \times 10^{13}$ vg/kg to about $8.0 \times 10^{13}$ vg/kg. about $1.8 \times 10^{13}$ vg/kg to about $8.0 \times 10^{13}$ vg/kg, about $1.2 \times 10^{13}$ vg/kg to about $7.5 \times 10^{13}$ vg/kg, about $1.9 \times 10^{13}$ vg/kg to about $7.5 \times 10^{13}$ vg/kg, about $1.4 \times 10^{13}$ vg/kg to about $7.4 \times 10^{13}$ vg/kg, about $1.9 \times 10^{13}$ vg/kg to about $7.5 \times 10^{13}$ vg/kg, or about $1.8 \times 10^{13}$ vg/kg to about $8.0 \times 10^{13}$ vg/kg based on a linearized DNA or plasmid as the quantitation standard. For example, the therapeutically effective amount of the rAAV vector is a dose of about $1.85 \times 10^{13}$ vg/kg or $7.41 \times 10^{13}$ vg/kg based on a linearized DNA or plasmid as the quantitation standard.

In one embodiment, the dose of $5.0 \times 10^{13}$ vg/kg based on a supercoiled DNA or plasmid as the quantitation standard is equivalent to the dose of $1.85 \times 10^{13}$ vg/kg based on a linearized DNA or plasmid as the quantitation standard. In another embodiment, the dose of $2.0\times10^{14}$ vg/kg based on a supercoiled DNA or plasmid is equivalent to $7.41\times10^{13}$ vg/kg based on a linearized DNA or plasmid as the quantitation standard. Therefore, in another embodiment, about $1.85\times10^{13}$ vg/kg or $7.41\times10^{13}$ vg/kg based on a linearized DNA or plasmid as the quantitation standard.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the α-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling. Thus, in another aspect, the application is directed to a formulation that comprises an rAAV that comprises an AAVrh74 derived capsid, a buffer agent, an ionic strength agent, and a surfactant. In one embodiment, the rAAV is at a concentration of about $1.0\times10^{12}$ vg/kg to about $5.0\times10^{14}$ vg/kg. In another embodiment, the rAAV is at a concentration of about $5.0\times10^{12}$ vg/kg to about $1.0\times10^{14}$ vg/kg. In another embodiment, the rAAV is at a concentration of about $5\times10^{13}$ vg/kg, about $1\times10^{14}$ vg/kg, and/or about $2\times10^{14}$ vg/kg. In one embodiment, the dosage is based on a supercoiled DNA or plasmid as the quantitation standard. In one embodiment, the rAAV is an scAAVrh74.tMCK.hSGCA vector. In one embodiment, the buffer agent comprises one or more of tris, tricine, Bis-tricine, HEPES, MOPS, TES, TAPS, PIPES, and CAPS. In another embodiment, the buffer agent comprises tris with pH 8.0 at concentration of about 5 mM to about 40 mM. In one embodiment, the buffer agent comprises tris with pH 8.0 at about 20 mM. In one embodiment, the ionic strength agent comprises one or more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. In one embodiment, the ionic strength agent comprises $MgCl_2$ at a concentration of about 0.2 mM to about 4 mM. In another embodiment, the ionic strength agent comprises NaCl at a concentration of about 50 mM to about 500 mM. In another embodiment, the ionic strength agent comprises $MgCl_2$ at a concentration of about 0.2 mM to about 4 mM and NaCl at a concentration of about 50 mM to about 500 mM. In another embodiment, the ionic strength agent comprises $MgCl_2$ at a concentration of about 1 mM and NaCl at a concentration of about 200 mM. In one embodiment, the surfactant comprises one or more of a sulfonate, a sulfate, a phosphonate, a phosphate, a Poloxamer, and a cationic surfactant. In one embodiment, the Poloxamer comprises one or more of Poloxamer 124, Poloxamer 181, Poloxamer 184, Poloxamer 188, Poloxamer 237, Poloxamer 331, Poloxamer 338, and Poloxamer 407. In one embodiment, the surfactant comprises the Poloxamer at a concentration of about 0.00001% to about 1%. In another embodiment, the surfactant comprises Poloxamer 188 at a concentration of about 0.001%. For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of α-sarcoglycan. The present invention thus provides methods of administering/delivering rAAV which express alpha-sarcoglycan to a mammalian subject, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol Cell Biol* 11: 4854-4862 (1991)], control elements derived from the human skeletal actin gene [Muscat et al., *Mol Cell Biol*, 7: 4089-4099 (1987)], the cardiac actin gene, muscle creatine kinase sequence elements [See Johnson et al., *Mol Cell Biol*, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA*, 88: 5680-5684 (1991)), steroid-inducible elements and promoters including the glucocorticoid response element (GRE) (See Mader and White, *Proc. Natl. Acad. Sci. USA* 90: 5603-5607 (1993)), and other control elements.

Muscle tissue is an attractive target for in vivo DNA delivery, because it is not a vital organ and is easy to access. The invention contemplates sustained expression of miRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of a polynucleotide of interest (e.g., a polynucleotide sequence encoding α-sarcoglycan) to a recipient cell either in vivo or in vitro, via a replication-deficient rAAV described resulting in expression of alpha-sarcoglycan by the recipient cell.

Thus, also described herein are methods of administering an effective dose (or doses, administered essentially simultaneously or doses given at intervals) of rAAV that encode alpha-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control. Described numerical ranges are inclusive of each integer value within each range and inclusive of the lowest and highest stated integers.

The invention is further described in the following Examples, which do not limit the scope of the invention described in the claims.

EXAMPLES

Preclinical studies using AAVrh74.tMCK.SGCA are described in International Patent Publication No. WO 2013/078316 and U.S. Pat. Nos. 9,434,928 and 10,105,453, which are incorporated by reference herein in its entirety.

Example 1

Materials and Methods

Animal Models

All procedures were approved by The Research Institute at the Nationwide Children's Hospital Institutional Animal Care and Use Committee. Knockout (sgca$^{-/-}$) mice were bred and maintained as homozygous animals under standardized conditions in the Animal Resources Core at the Research Institute at Nationwide Children's Hospital. Mice were maintained on Teklad Global Rodent Diet (3.8% fiber, 18.8% protein, 5% fat chow) with a 12:12-hour dark:light cycle. All animals were housed in standard mouse cages with food and water ad libitum.

Genotyping

DNA genotyping was used to identify sgca$^{-/-}$ mice. DNA from tail clippings was isolated and analyzed by polymerase chain reaction (PCR) using OneTaq DNA Polymerase (New England Biolabs, Ipswich, MA). A series of primers was used in the PCR analysis to determine the α-SG knockout status. The following primers and conditions were used: Intron1 (CAGGGCTGGGAGCTGGGTTCTG; SEQ ID NO: 9); mutant primer-intron 3 (CCCAGGGCCTT-GATGCCT; SEQ ID NO: 10); and NEOTR (GC-TATCAGGACATAGCGTTGGCTA; SEQ ID NO: 11). Reactions were carried out on genomic DNA for 30 cycles under the following conditions: 94° C., 5 min; 94° C., 1 min; 64° C., 1 min; 72° C., 2.5 min; and 72° C., 7 min.

α-SG Gene Construction

The scAAVrh74.tMCK.hSGCA transgene cassette was made using an adeno-associated virus (AAV) vector DNA plasmid pAAV.tMCK.aSG-neo, by inserting the tMCK expression cassette driving a codon-optimized human α-SG cDNA sequence (human cDNA, Genbank Accession

U08895) into the self-complementary vector backbone pHpa7. The only viral sequences included in this vector are the inverted terminal repeats of AAV2, which are required for both viral DNA replication and packaging of the rAAV vector genome. One of the inverted terminal repeats (ITRs) has a targeted deletion of the terminal resolution site (TRS) to restrict replication from this ITR facilitating generation of the dimeric replicative form for self-complementary vector packaging. The AAVrh74 virus has been proven in mice, non-human primates (NHPs), and humans to be safe and highly efficient in transducing muscle across the vascular barrier.

Vector Production

The recombinant AAV, (sc)rAAVrh74.tMCK.hSGCA, was made in by triple transfection. A qPCR-based titration method was used to determine an encapsulated vg titer utilizing a Prism 7500 Fast Taqman detector system (PE Applied Biosystems). The construct comprises a chimeric intron to promote high-level expression. The chimeric intron is composed of the 5' donor site from the first intron of the human β-globin gene and the branchpoint and 3' splice acceptor site from the intron that is between the leader and the body of an immunoglobulin gene heavy chain variable region. The rAAV also comprises a synthetic SV40 polyadenylation signal is used for efficient transcription termination. A schematic of the expression cassette is shown below in FIG. 1. The vector was produced using the human alpha-sacroglycan (α-SG) gene flanked by AAV2 ITR sequences and encapsidated into AAVrh74 virions. The construct contains the tMCK immediate early promoter/enhancer (GenBank Accession No. M21390) and uses the β-globin intron for high-level expression.

Gene Delivery

Systemic delivery in mice was achieved through injection of vector into the tail vein of sgca−/− mice. Mice were injected with a $1\times10^{12}$ vg, $3\times10^{12}$ vg, or $6\times10^{12}$ vg total dose (mice ranging from 13-20 g; $5\times10^{13}$ vg/kg, $1\times10^{14}$ vg/kg, and $2\times10^{14}$ vg/kg—the dosages based on a supercoiled DNA or plasmid as the quantitation standard—respectively, based on a 20-g mouse) of scAAVrh74.tMCK.hSGCA diluted in lactated Ringer's solution in a 200-250 µL volume using a 30-gauge ultra-fine insulin syringe. All treated mice were injected at 4-5 weeks of age and euthanized 12 weeks post-injection. In another embodiment, the dose is about $1.85\times10^{13}$ vg/kg or $7.41\times10^{13}$ vg/kg based on a linearized DNA or plasmid as the quantitation standard.

Serum Creatine Kinase Measurement

Levels of creatine kinase were measured in the sera of wild-type C57BL/6 mice (n=6), vehicle (lactated Ringers solution)-treated sgca$^{-/-}$ mice (n=6), and scAAVrh74.tMCK.hSGCA-treated sgca$^{-/-}$ mice (n=6 per dose) using the Creatine Kinase SL Assay and the corresponding manufacturer's protocol (Sekisui Diagnostics; Charlottetown, PE, Canada) (catalog no. 326-10). Briefly, 25 µL of serum was mixed with 1 mL of the working reagents and added to a cuvette. A kinetic assay was set on the spectrophotometer to measure the absorbance at 340 nm every 30 sec for 180 sec. Creatine kinase levels were calculated using the absorbance readings and the equation listed below:

$$U/L=[\Delta Abs./min)*1.025*1000]/[1*6.22*0.025]=(\Delta Abs./min)*6592.$$

Diaphragm Tetanic Contraction for Functional Assessment

Mice were euthanized and the diaphragm (DIA) was dissected with rib attachments and central tendon intact, and placed in K-H buffer. A 2-4 mm wide section of DIA was isolated. DIA strips were tied firmly with braided surgical silk (6/0; Surgical Specialties, Reading, PA) at the central tendon, and sutured through a portion of rib bone affixed to the distal end of the strip. Each muscle was transferred to a water bath filled with oxygenated K-H solution that was maintained at 37° C. The muscles were aligned horizontally and tied directly between a fixed pin and a dual-mode force transducer-servomotor (305C; Aurora Scientific, Aurora, Ontario, Canada). Two platinum plate electrodes were positioned in the organ bath so as to flank the length of the muscle. The muscle was stretched to optimal length for measurement of twitch contractions, and then allowed to rest for 10 minutes before initiation of the tetanic protocol. Once the muscle was stabilized, it was set to an optimal length of 1 g and subjected to a warm-up, which consisted of three 1-Hz twitches every 30 sec followed by three 150-Hz twitches every minute. After a 3-min rest period, the DIA was stimulated at 20, 50, 80, 120, 150, 180 Hz, allowing a 2-min rest period between each stimulus, each with a duration of 250 ms to determine maximum tetanic force. Muscle length and weight were measured. The force was normalized for muscle weight and length.

Tibialis Anterior (TA) Tetanic Contraction for Functional Assessment

The TA assessment procedure followed the protocol listed in Hakim et al., *Methods Mol Biol*; 709:75-89 (2011). Mice were anesthetized via intraperitoneal cavity using ketamine/xylazine mixture (100 mg/kg and 10 mg/kg, respectively). Under a dissecting scope, the hind limb skin was removed to expose the TA muscle and patella. A double square was tied around the patella tendon with a 4-0 suture. The TA distal tendon was then dissected out and a double square knot was tied around the tendon with 4-0 suture as close to the muscle as possible and then the tendon was cut. The exposed muscle was constantly dampened with saline. Mice were then transferred to a thermal controlled platform and maintained at 37° C. The knee was secured to the metal pin with the patella tendon suture and the distal TA tendon suture to the level arm of the force transducer (Aurora Scientific, Aurora, Canada). An electrode was placed near the sciatic nerve to stimulate it. Once the muscle was stabilized, the resting tension was set to a length (optimal length) where twitch contractions were maximal. After a 3-min rest period, the TA was stimulated at 50, 100, 150 and 200 Hz, allowing a 1-min rest between each stimulus. Following a 5-min rest, the muscles were then subjected to a series of 10 isometric contractions, occurring at 1-min intervals with a 10% stretch-re-lengthening procedure. After the eccentric contractions, the mice were then euthanized and the TA muscle was dissected and frozen for histology.

Immunofluorescence

Cryosections (12-µm thick) from the TA, gastrocnemius (GAS), quadricep (QD), psoas major (PSOAS), gluteus (GLUT), tricep (TRI), DIA, and heart (HRT) muscles were subjected to immunofluorescence staining for the hSGCA transgene. Sections were incubated with a rabbit monoclonal α-SG primary antibody (Abcam; Cambridge, UK; catalog no.ab189254) at a dilution of 1:100. Four random 20× images covering the four different quadrants of the muscle section were taken using a Zeiss (Germany) AxioCam MRCS camera. The percentage of fibers positive for α-SG staining compared to controls was determined for each image and averaged for each muscle. Positive α-SG fiber expression was defined as having at least 30% of the fiber staining brighter than the vehicle-treated sgca−/− controls.

Western Blot Analysis

Samples from wild-type C57BL/6 mice, vehicle-treated sgca−/− mice, and vector-dosed sgca−/− mice were used for each Western blot. A 1:10,000 dilution of a rabbit monoclonal α-SG antibody (Abcam, catalog no.ab189254) and a 1:5,000 dilution of a mouse monoclonal α-actinin antibody (Sigma-Aldrich, catalog no. A7811) were used for hSGCA blots. A 1:1,000 dilution of a rabbit monoclonal mouse vinculin antibody (Invitrogen, catalog no. 70062) was also used. Anti-mouse (Millipore, catalog no. AP308P) and anti-rabbit (Life Technologies, catalog no. 656120) secondary horseradish peroxidase antibodies were used for enhanced chemiluminescence immunodetection. Western blot quantification was performed by densitometry using ImageQuantTL 1D 8.1.0 (GE Healthcare Life Sciences).

Morphometric Analysis

Hematoxylin & eosin (H&E) staining was performed on 12-μm thick cryosections of muscle from 16-17-week-old wild-type C57BL/6 mice (n=6), vehicle-treated sgca−/− mice (n=6), and scAAVrh74.tMCK.hSGCA 16-17-week-old treated sgca−/− mice (n=6 per dose) for analysis. The percentage of myofibers with central nuclei was determined in the TA, GAS, QD, GLUT, PSOAS, and TRI muscles. Additionally, muscle fiber diameters were measured in the TA, GAS, QD, TRI, and PSOAS muscles. Four random 20× images per muscle per animal were taken with a Zeiss AxioCam MRC5 camera. Centrally nucleated fibers were quantified using the National Institutes of Health's ImageJ software, and fiber diameters were measured using Zeiss Axiovision LE4 software.

Biodistribution Quantitative Polymerase Chain Reaction (PCR) Analysis

Taqman quantitative PCR was performed to quantify the number of vector genome copies present in targeted and untargeted contralateral muscle as well as non-targeted organs as previously described. A vector-specific primer probe set was used to amplify a sequence of the intronic region directly downstream from the tMCK promoter that is unique and located within the scAAVrh.74.tMCK.hSGCA transgene cassette. The following primers and probe were used in this study: tMCK intron Forward Primer 5'-ACC CGA GAT GCC TGG TTA TAA TT-3' (SEQ ID NO: 12); tMCK intron Reverse Primer 5'-TCC ATG GTG TAC AGA GCC TAA GAC-3' (SEQ ID NO: 13); and tMCK intron probe 5'-FAM-CTG CTG CCT GAG CCT GAG CGG TTA C-IABkFQ-3' (SEQ ID NO: 14) (Integrated DNA Technologies). Copy number was reported as vector genomes per microgram of genomic DNA.

Picrosirius Red Stain and Collagen Quantification

Picrosirius red staining was performed to determine the levels of collagen deposition in muscle tissue. Staining was performed on 12-μm cryosections from 16-17-week-old wild-type C57BL/6 (n=6), vehicle-treated sgca−/− (n=6), and scAAVrh74.tMCK.hSGCA 16-17-week-old treated sgca−/− (n=6 per dose) GLUT, PSOAS, TRI, and DIA muscles. Four 20× images were taken per muscle per mouse, and the amount of collagen deposition was determined with the ImageJ software program. The mean percent collagen for each muscle was calculated for all groups.

Laser Monitoring of Open-Field Cage Activity

An open-field activity chamber was used to determine the overall activity of the experimental mice. Mice at 16-17 weeks of age from the wild-type C57BL/6 (n=6) and untreated sgca$^{-/-}$ (n=6) control groups, along with scAAVrh74.tMCK.hSGCA 16-17-week-old treated sgca$^{-/-}$ mice (n=6 per dose) were subjected to analysis. All mice were tested at the same time of day, in the early morning near the end of the night cycle, when mice are most active. All mice were tested in an isolated room under dim light and with the same handler each time. Also, to reduce anxiety and keep behavioral variables at a minimum that could potentially affect normal activity of the mice and consequently the results of the assay, we tested mice that were not individually housed. Mouse activity was monitored using the Photobeam activity system (San Diego Instruments, San Diego, CA). This system uses a grid of invisible infrared light beams that traverse the animal chamber front to back and left to right to monitor the position and movement of the mouse within an x-y-z plane. Activity was recorded for 1-hour cycles at 5-min intervals. Mice were acclimatized to the activity test room for an initial 1-hour session several days prior to beginning data acquisition. Mice were tested in individual chambers in sets of four. The testing equipment was cleaned between each use to reduce mouse reactionary behavioral variables that could alter results. The data were converted to a Microsoft Excel worksheet, and all calculations were done within the Excel program. Individual beam breaks for movement in the x and y planes were added up for each mouse to represent total ambulation, and beam breaks in the z plane were added up to obtain vertical activity within the 1-hour time interval.

Safety Studies

Hematology

Whole blood was retrieved from cardiac puncture for blood chemistries. Blood was collected in a serum separating tube and centrifuged for 10 min at 15,000 rpm. Serum was collected, frozen, and sent to Charles River Laboratories for chemistry testing. Liver enzymes and glucose chemistries were prioritized in the hematology analysis.

Histopathology

At necropsy, muscles were fresh frozen in liquid nitrogen-cooled methyl-butane; all other organs were harvested and fixed in formalin and embedded in paraffin. After processing, tissues were stained with H&E, and slides and all tissues were sent to GEMPath, Inc, for formal review by a veterinary pathologist.

Statistical Analysis

Data were expressed as the mean±SEM (error bars) and analyzed using a one-way ANOVA with multiple comparisons between groups assessed by Tukey's post-hoc analysis test using GraphPad Prism 5 (GraphPad Software, La Jolla, CA) unless otherwise specified.

Example 2

Efficiency of Systemic Delivery of scAAVrh74.tMCK.hSGCA

A small pilot study was initiated to observe efficacy of gene delivery by intravenous injection into the lateral tail vein of sgca$^{-/-}$ mice at a dose of $1×10^{12}$ vg total dose ($5×10^{13}$ vg/kg based on 20-g mouse, n=4). Immunofluorescence analysis was performed on harvested muscles 4 weeks post-gene transfer. The amount of hSGCA transgene expression in seven different limb skeletal muscles: TA, GAS, GLUT, QD, PSOAS, and TRI and DIA. Mice deficient for α-SG showed a complete absence of the protein when analyzed by immunofluorescence (FIG. 2A; representative images of TA, GAS, TRI and DIA). The therapeutic dose of $1×10^{12}$ vg total dose resulted in a mean 54±23.81% vector transduction across all skeletal muscles including the DIA 4 weeks post-gene delivery.

Figure 2:
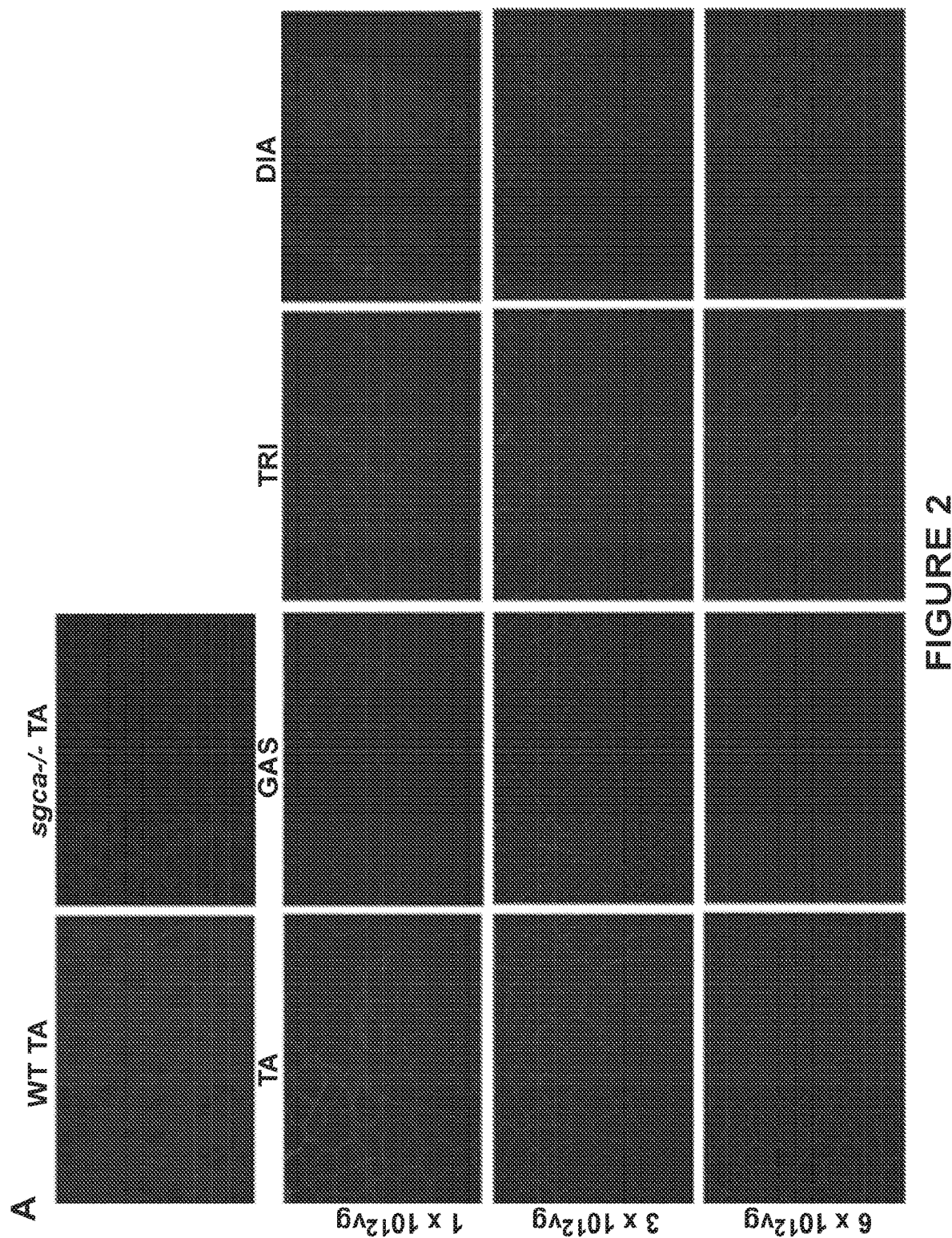
FIG. 2 shows transgene expression in a dose-escalation study after systemic treatment with scAAVrh74.tMCK.hSGCA. (A) alpha-sarcoglycan immunofluorescence stain of multiple muscles from mice systemically (intravenous) treated with $1\times10^{12}$ vg, $3\times10^{12}$ vg, and $6\times10^{12}$ vg (or $5\times10^{13}$ vg/kg, $1\times10^{14}$ vg/kg, and $2\times10^{14}$ vg/kg, respectively, based on a 20-g mouse) (n=6 per group). Muscle fibers expressing the alpha-sarcoglycan 12 weeks post-treatment ranged from 70%-93% compared to untreated controls. (B) Western blots of muscles from treated sgca$^{-/-}$ mice confirm hSGCA protein expression. Abbreviations: TA, tibialis anterior; GAS, gastrocnemius; QD, quadricep; TRI, tricep; GLUT, gluteus; PSO, psoas major; DIA, diaphragm; HRT, heart; WT, wild-type.
Figure 2:
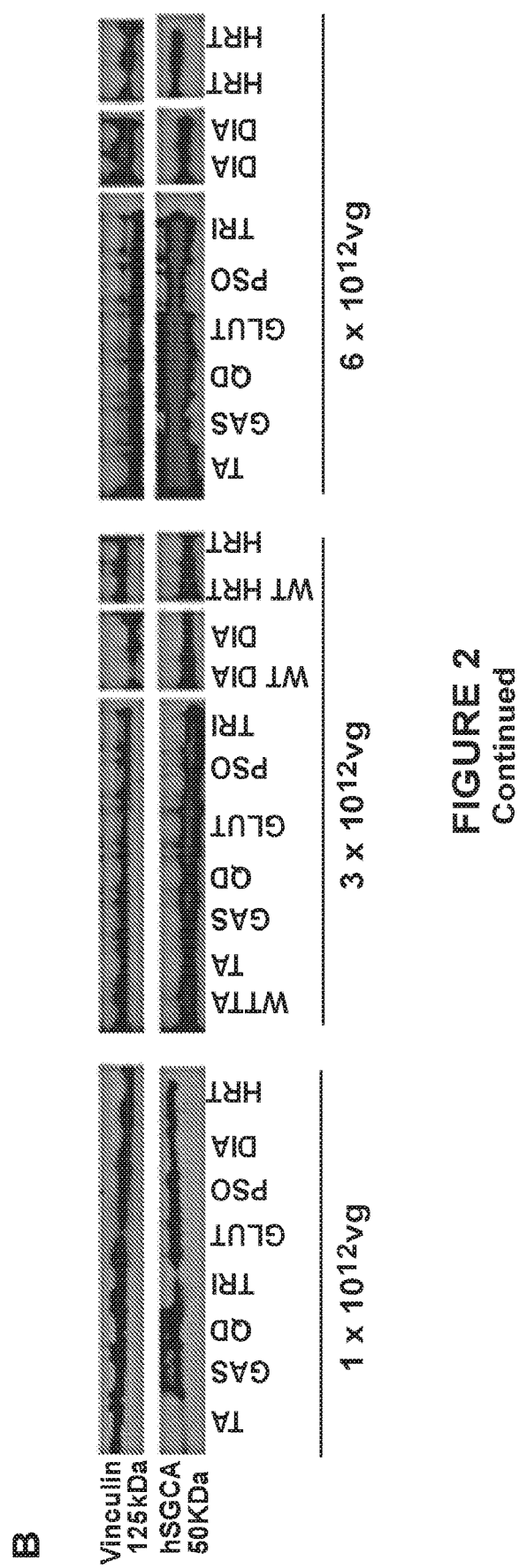

Dose-Escalation Study of scAAVrh74.tMCK.hSGCA Delivered Systemically to Sgca$^{-/-}$ Mice To determine the safest and most efficacious dose, the delivery of three separate doses of vector was studied in a dose-escalation study, where the lateral tail vein of 4-week-old sgca$^{-/-}$ mice were treated with $1\times10^{12}$ vg total dose ($5\times10^{13}$ vg/kg), $3\times10^{12}$ vg total dose ($1\times10^{14}$ vg/kg), or $6\times10^{12}$ vg total dose ($2\times10^{14}$ vg/kg) of scAAVrh74.tMCK.hSGCA. Mice were euthanized 12 weeks post-gene delivery to assess hSGCA transgene expression in the TA, GAS, QD, GLUT, PSOAS, TRI, DIA, and HRT muscles using immunofluorescence. Mean hSGCA expression in mice treated with the lowest dose of $1\times10^{12}$ vg total dose ($5\times10^{13}$ vg/kg) was 70.07±3.71% overall expression in the skeletal muscles, including the DIA. Mean hSGCA expression in mice treated with the intermediate dose of $3\times10^{12}$ vg total dose ($1\times10^{14}$ vg/kg) was 85.35±2.36% in all skeletal muscles. Mean hSGCA expression in mice treated with the highest dose of $6\times10^{12}$ vg total dose ($2\times10^{14}$ vg/kg) was 93.86±2.02% in all skeletal muscles. For clarity, the doses were calculated based on a supercoiled DNA or plasmid as the quantitation standard. The hSGCA expression in the HRT muscle remained at 75% independent of dose. Representative images of tissues are shown in FIG. 2A. The robust hSGCA expression shows efficacy of gene delivery at all three doses. The gene delivery targeted multiple muscles in both forelimbs and hind limbs, showing exceptional α-SG expression in the mice at all three doses. Most importantly, the vital diaphragm muscle also showed α-SG gene expression after delivery. Western blots shown in FIG. 2B confirm protein expression in all muscles of all three dosing cohorts of the treated mice. The cardiac muscle in mice also showed α-SG expression after treatment.

Figure 3:
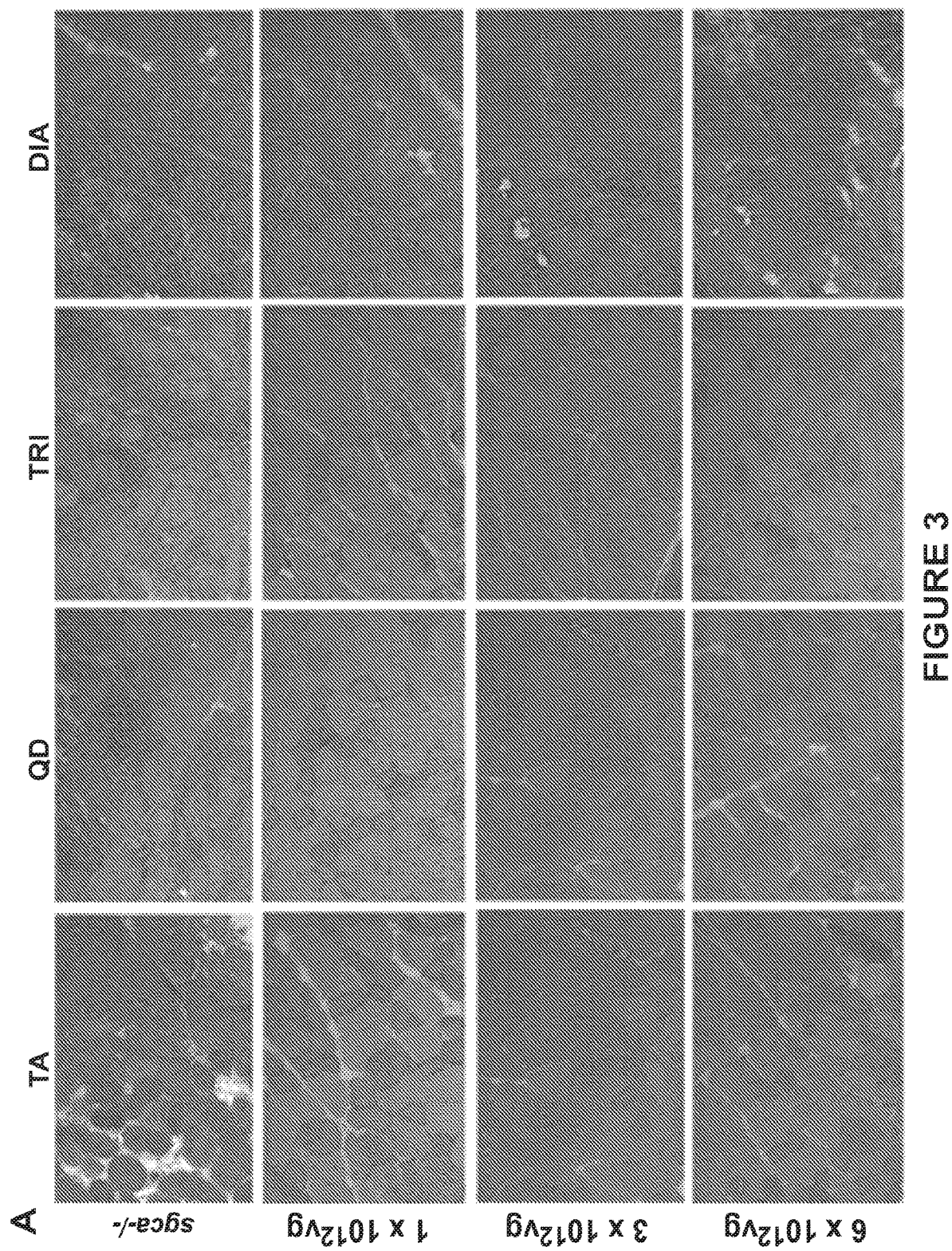
FIG. 3 shows improvement in muscle morphology by scAAVrh74.tMCK.hSGCA independent of dose in sgca-/- mice. (A) Hematoxylin & eosin images of various muscles from sgca-/- mice treated with $1\times10^{12}$ vg, $3\times10^{12}$ vg, and $6\times10^{12}$ vg (or $5\times10^{13}$ vg/kg, $1\times10^{14}$ vg/kg, and $2\times10^{14}$ vg/kg, respectively, based on a 20-g mouse) of scAAVrh74.tMCK.hSGCA. Representative 20× images show a dramatic reduction in centralized nuclei and an overall normalization of fiber size independent of treatment dose. (B) Quantification confirming myofiber diameter normalization of various muscles in treated groups compared to vehicle-treated mice and wild-type controls (n=6 per group). (C) Quantification of centrally located nuclei in muscles of treated mice compared to untreated mice and wild-type controls (n=6 per group). Abbreviations: TA, tibialis anterior; GAS, gastrocnemius; QD, quadricep; GLUT, gluteus; PSO, psoas major; TRI, tricep; DIA, diaphragm; WT, wild-type.
Figure 3:
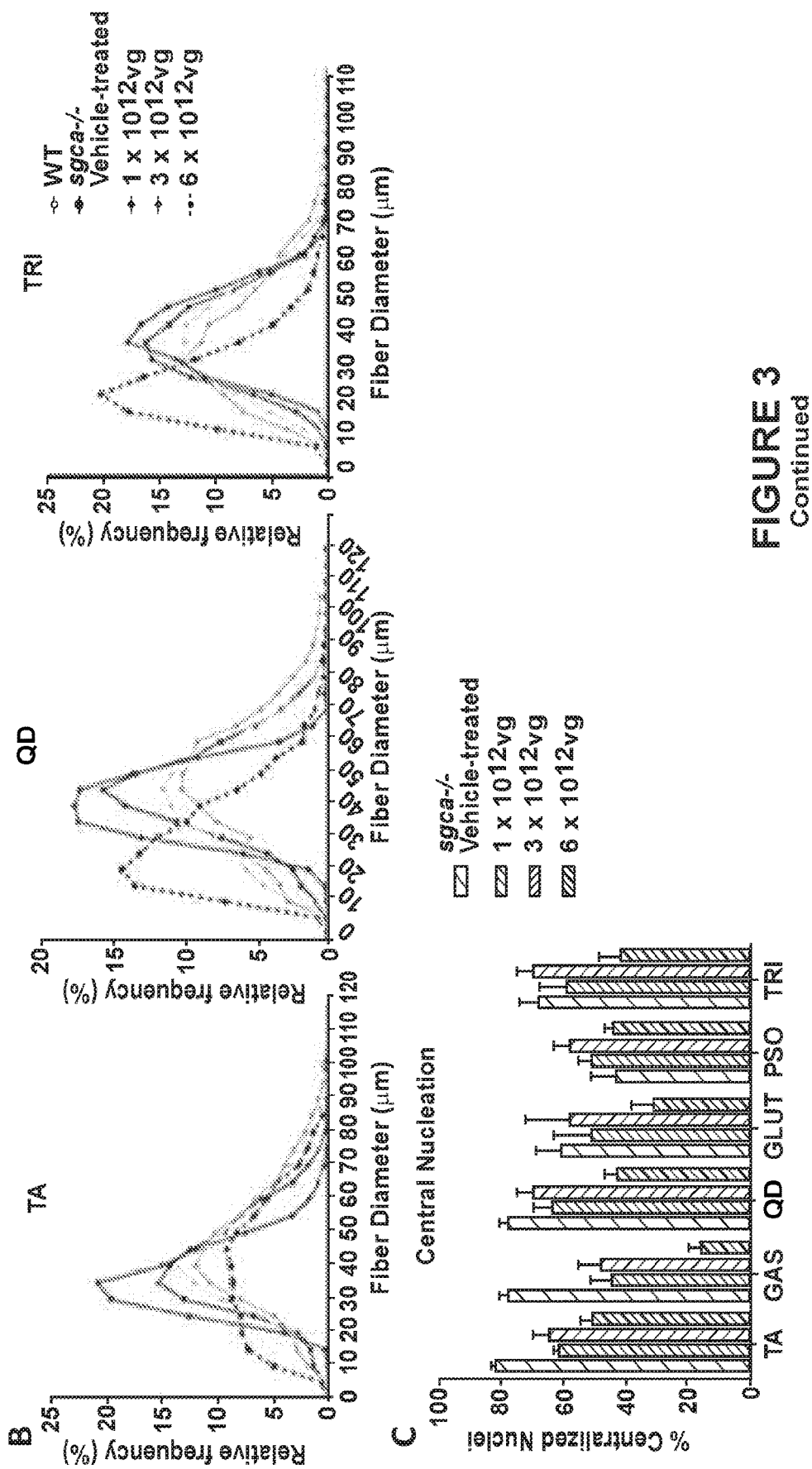

Histopathological characteristics of both humans and mice devoid of α-SG protein include central nucleation, irregularities in fiber size distribution, necrosis, and fibrosis. H&E staining was used to visualize muscle morphology, including fiber size and central nucleation (FIG. 3). As shown in FIGS. 3A and 3B, a normalization of fiber size distribution, similar to that observed in wild-type controls, was observed in the TA, QD, and TRI of scAAVrh74.tMCK.hSGCA-treated sgca$^{-/-}$ mice compared to vehicle-treated sgca$^{-/-}$ controls. The average diameter size of fibers was significantly increased at all doses in the TA, QD, and TRI muscles compared to vehicle-treated sgca−/− control mice (Table 1).

In sgca$^{-/-}$ mice treated with scAAVrh74.tMCK.hSGCA, reduction in central nucleation was also observed. Skeletal muscles of vehicle-treated sgca$^{-/-}$ mice had 68.72±3.01% fibers with centrally located nuclei. After treatment with scAAVrh74.tMCK.hSGCA, the overall value of central nucleation across all muscle tissues was reduced with the lowest dose of scAAVrh74.tMCK.hSGCA, resulting in 55.60±3.25% of skeletal muscle fibers showing centrally located nuclei (Table 2).

TABLE 2

| | Central nucleation (%) | | | |
|---|---|---|---|---|
| Tissue | Untreated | Lowest Dose | Intermediate Dose | Highest Dose |
| TA | 82.06 | 61.6**** | 64.61 | 51.29**** |
| GAS | 78.01 | 44.98*** | 48.43 | 16.19*** |
| QD | 78.28 | 63.82 | 70.35 | 42.79**** |
| GLUT | 60.61 | 51.73 | 58.28 | 31.18 |
| PSO | 43.42 | 50.99 | 58.78 | 44.42 |
| TRI | 68.34 | 59.57 | 70.37 | 41.72 |
| AVG | 68.72 ± 3.01 | 55.60 ± 3.25 | 61.85 ± 4.00 | 37.93 ± 12.46 |

****= $p < 0.0001$.
Abbreviation: TA, tibialis anterior; GAS, gastrocnemius; QD, quadricep; GLUT, gluteus; PSO, psoas majorl, AVG, average; and TRI, tricept Mice treated with the intermediate dose had 61.85±4.00% of muscle fibers with centralized nuclei, while the nucleation of muscle fibers treated with the highest dose was reduced to 37.93±12.46% (FIG. 3C).

Figure 4:
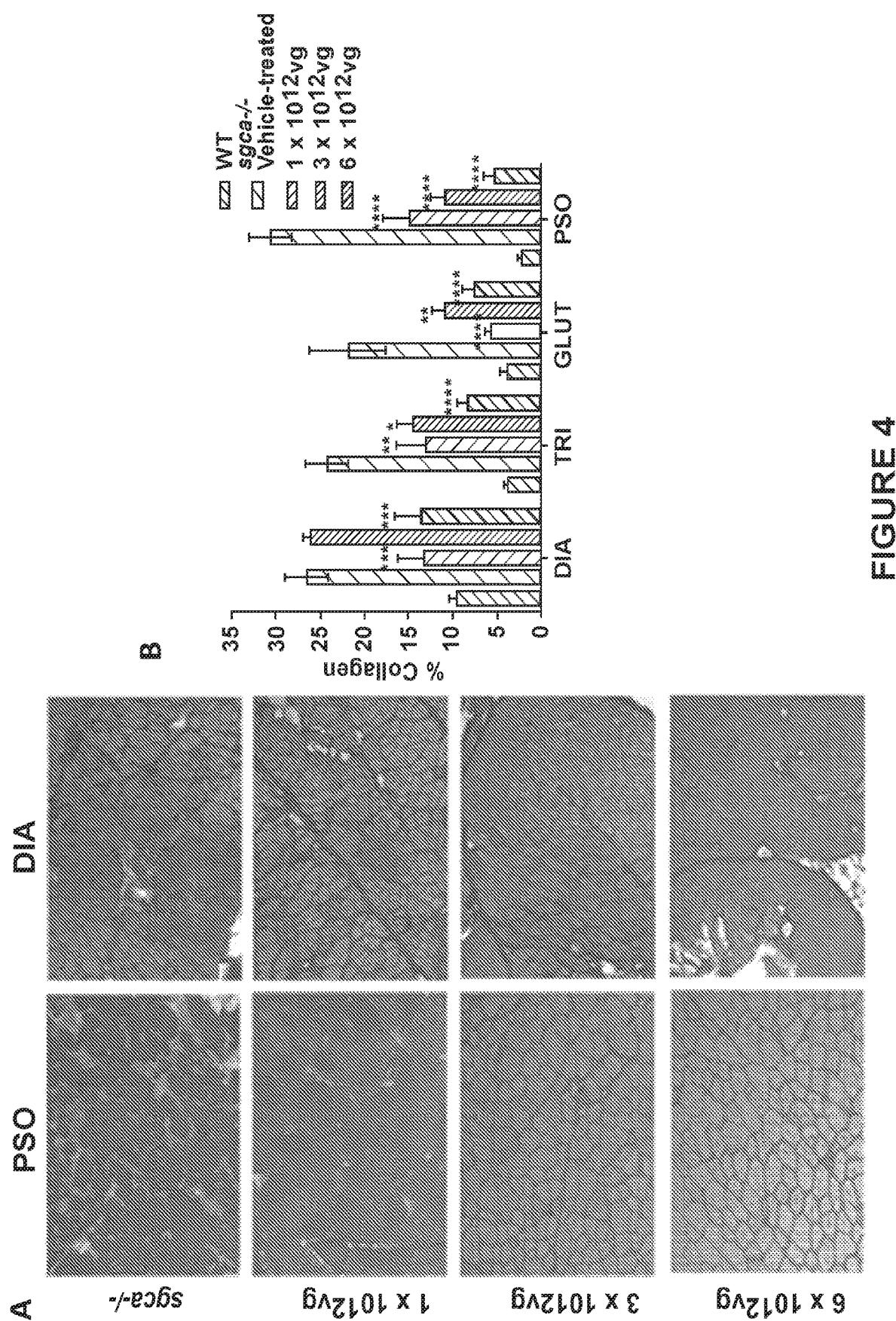
FIG. 4 shows reduction fibrosis in sgca$^{-/-}$ mice treated with scAAVrh74.tMCK.hSGCA. (A) Picrosirius red staining shows reduced fibrosis in scAAVrh74.tMCK.hSGCA treated mice indicated by a decrease in collagen deposition compared to vehicle-treated sgca$^{-/-}$ mice in various muscles Representative 20× images shown. (B) Quantification of collagen levels in various muscles confirms reduction in collagen levels in all three treated groups compared to untreated mice and wild-type controls (n=6 per group). Abbreviations: PSO, psoas major; DIA, diaphragm; TRI, triceps; GLUT, gluteus.

Fibrosis, where the tissue is overcome by collagen, often occurs in the muscles of LGMD patients, leading to the formation of scar tissue. Fibrosis was assessed using a picrosirius red stain to detect collagen I and III content, as a marker of fibrosis. As shown in FIG. 4, a robust reduction in red staining was observed in sgca−/− mice after treatment with scAAVrh74.tMCK.hSGCA. Quantification revealed a significant reduction in collagen content across all muscles in scAAVrh74.tMCK.hSGCA treated sgca−/− mice compared to vehicle-treated sgca$^{-/-}$ control mice (FIG. 4B). Together, these data demonstrate successful systemic delivery of the hSGCA transgene as indicated by robust expression in muscle tissues and improvement in histopathological hallmarks associated with the lack of α-SG protein in sgca$^{-/-}$ mice.

Figure 5:
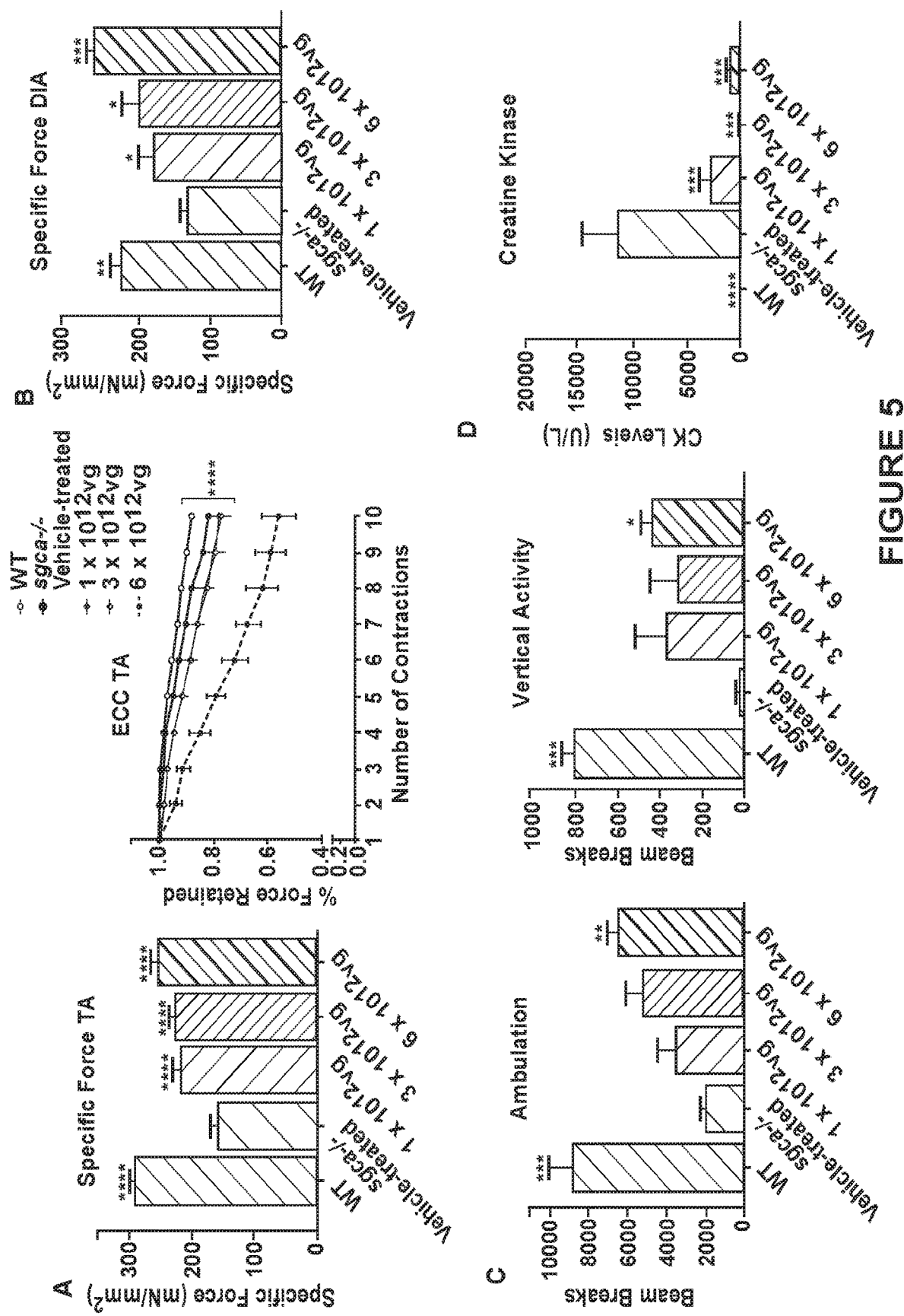
FIG. 5 shows functional benefits to skeletal muscle after treatment with scAAVrh74.tMCK.hSGCA. (A) Following 3 months of treatment, tibialis anterior (TA) muscles were harvested (both left and right) to measure specific force and resistance to contraction-induced damage (normalized to TA weight). The quantification of specific force and eccentric contraction was increased in all treated groups (with minimal difference between doses) compared to untreated controls (n=6 per group). (B) Diaphragm muscle strips were harvested to measure specific force. Following 12 weeks of treatment, the force was significantly increased in treated mice compared to untreated sgca$^{-/-}$ mice. (C) Following 12 weeks of treatment, improvement was seen in ambulation and vertical activity through open-field analysis in treated mice compared to untreated sgca$^{-/-}$ controls (n=6 per group). (D) Creatine kinase levels in serum decreased in all treatment groups compared to untreated sgca$^{-/-}$ controls. Data were analyzed by one-way ANOVA followed by Tukey's post hoc analysis for multiple comparisons. *=$p<0.05$, =$p<0.01$, *=$p<0.001$, ****=$p<0.0001$ compared to vehicle-treated sgca$^{-/-}$ mice, unless noted. Abbreviations: TA, tibialis anterior; DIA, diaphragm; WT, wild-type.

Example 3 scAAVrh74.tMCK.hSGCA rAAV Improved Diaphragm and Tibialis Anterior Muscle Function and Increases Locomotor Ability As weakness and loss of function of proximal muscles are major symptoms of LGMD2D and respiratory failure is the leading cause of death in LGMD2D, improving the functionality and strength of the TA and DIA is imperative to increasing the length and quality of life in subjects with LGMD2D. Strips of the DIA and whole TA muscles were used to confirm the correlation between hSGCA expression and muscle strength. As shown in FIGS. 5A and 5B, a deficit in specific force and resistance to contraction-induced injury

TABLE 1

| | Fiber Diameter (μm) | | | |
|---|---|---|---|---|
| Tissue | Untreated | Lowest Dose | Intermediate Dose | Highest Dose |
| TA | 40.23 ± 19.33 | 46.24 ± 18.08**** | 43.16 ± 15.88**** | 41.37 ± 13.54* |
| QD | 30.87 ± 15.56 | 48.10 ± 19.96**** | 43.00 ± 16.87**** | 45.65 ± 14.51**** |
| TRI | 25.05 ± 12.09 | 36.47 ± 16.50**** | 37.01 ± 14.14**** | 38.63 ± 11.58**** |

*= $p < 0.05$,
****= $p < 0.0$.
Abbreviation: TA, tibialis anterior, AD: quadricep; and TRI, tricep. Lowest dose: $1.0 \times 10^{12}$ vg; intermediate dose: $3.0 \times 10^{12}$ vg; highest dose: $6.0 \times 10^{12}$ vg.

was identified in the TA and specific force in the DIA muscles of sgca$^{-/-}$ untreated mice compared to wild-type mice.

TA muscles of sgca$^{-/-}$ mice exhibited a significant functional deficit of 44% in the reduction of specific force output compared to wild-type mice (161.6±8.20 mN/mm$^2$ vs. 291.7±6.17 mN/mm$^2$, respectively; p<0.0001), as well as a greater loss of force from that produced following a rigorous eccentric contraction protocol (44.0±6.0% loss in sgca$^{-/-}$ mice; 18.0±1.0% loss in wild-type mice; p<0.0001) (FIG. 5A). Twelve weeks following tail vein delivery, Applicant noted a dramatic improvement after treatment with low, intermediate, and high doses of scAAVrh74.tMCK.hSGCA in specific force output, which increased to 218±11.94 mN/mm$^2$, 227±11.7 mN/mm$^2$, and 255±11.7 mN/mm$^2$, respectively. Resistance to injury following an eccentric contraction protocol also improved compared to vehicle-treated sgca$^{-/-}$ mice, in which the low-, intermediate-, and high-dose treated mice only lost 22.0±4.0%, 22.0±3.0%, and 12.0±1.0%, respectively (p<0.0001 compared to vehicle-treated sgca$^{-/-}$ mice) (FIG. 5A).

In the DIA of vehicle-treated sgca$^{-/-}$ mice, the specific force generated showed a 41% reduction in strength compared to wild-type mice (131.5±12.07 mN/mm$^2$ vs. 223.8±15.85 mN/mm$^2$). An improvement in force was observed following treatment with scAAVrh74.tMCK.hSGCA at all three doses, where the specific force of the DIA in low-dosed mice increased to 179.2±21.03 mN/mm$^2$, in intermediate-dosed mice increased to 201.2±22.94 mN/mm$^2$ and in high-dosed mice increased to 261.46±9.73 mN/mm$^2$ (FIG. 65B). These data show that the TA and DIA muscles in sgca$^{-/--}$ mice have a deficit in force and are faster to exhaust than wild-type mice. However, after the delivery of scAAVrh74.tMCK.hSGCA, functional recovery was achieved.

Additional symptoms of LGMD2D include exercise intolerance and reduced activity and ambulation, possibly due to muscle damage, resulting in pain and muscle fatigue. To assess the level of physical activity, sgca$^{-/-}$ and wild-type C57BL/6 mice were subjected to an open-field activity protocol similar to that used in previous reports. The ambulation-related activities of mice were monitored to determine if the lack of α-SG in the sgca$^{-/-}$ mouse leads to a decrease in ambulation compared to wild-type mice. The graphs in FIG. 5C depict a reduction in ambulation and vertical rearing in the sgca$^{-/-}$ mouse model compared to wild-type controls. The mean horizontal ambulatory beam breaks recorded in the sgca$^{-/-}$ mice was 2000±159 beam breaks/hr, a 77.5% decrease in ambulation compared to 8911±1193 beam breaks/hr in wild-type controls. The mean vertical rearing beam breaks recorded in the sgca$^{-/-}$ mice was 24.75±11.47 beam breaks/hr, a 97% decrease in vertical rearing compared to 803.3±55.03 beam break/hr in wild-type mice. After treatment with scAAVrh74.tMCK.hSGCA, the ambulation and vertical rearing activities of mice increased 12 weeks post-gene delivery. The mean horizontal ambulation increased to 3595±55.03 beam breaks/hr in mice treated with 1×10$^{12}$ vg total dose, 5238±861.9 beam breaks/hr in mice treated with 3×10$^{12}$ vg total dose, and 6487±467.9 beam breaks/hr in mice treated with 6×10$^{12}$ vg total dose. The mean vertical rearing activity increased to 377±146.1 beam breaks/hr in mice treated with 1×10$^{12}$ vg total dose, 321±126.1 beam breaks/hr in mice treated with 3×10$^{12}$ vg total dose, and 448.8±53.43 beam breaks/hr in mice treated with 6×10$^{12}$ vg total dose (FIG. 5C). The physical activities of the treated mice showed improvement from 44%-69% in ambulation and 92%-94% in vertical rearing compared to vehicle-treated sgca$^{-/-}$ mice. Additionally, serum creatine kinase levels were significantly reduced in all treated groups compared to untreated mice (FIG. 5D). Together, these data show that the delivery of α-SG restores the physical activity and protects against the breakdown of muscle in sgca$^{-/-}$ mice.

Safety and Biodistribution Analysis of scAAVrh74.tMCK.hSGCA

Figure 6:
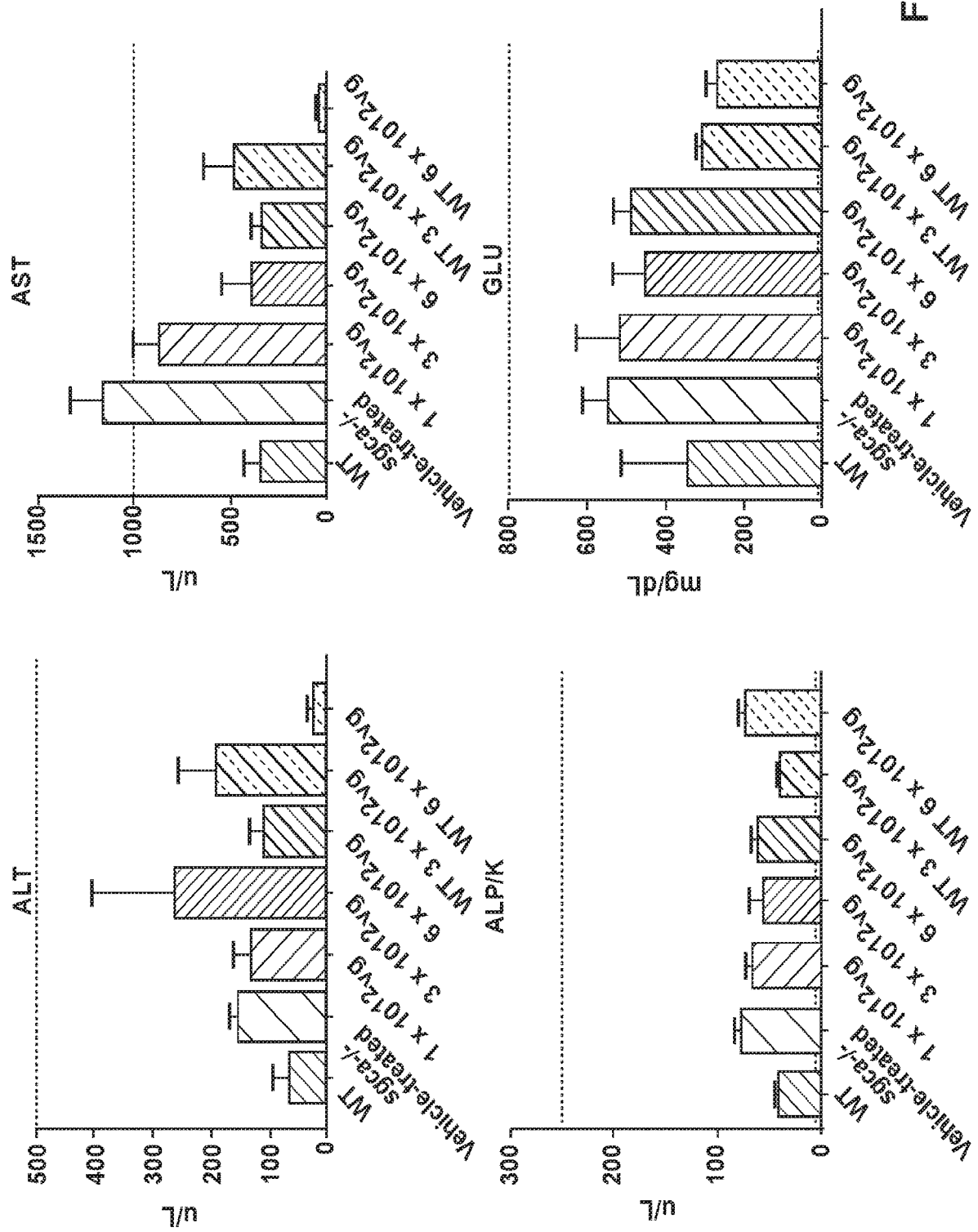
FIG. 6 shows no evidence of toxicity through blood chemistries after treatment with scAAVrh74.tMCK.hSGCA. Liver enzymes (ALT, AST and ALP/K) and blood glucose (GLU) levels were analyzed for toxicity (n=6 per group). All chemistry values of treated mice were within the normal/healthy limits of mice as indicated by the dotted lines.

As a safety provision, blood chemistries and hematology studies were performed on vector-dosed sgca$^{-/-}$ and wild-type mice. All values were within the normal reference ranges for mice (FIG. 6). Furthermore, tissue sections of all muscles and organs stained with H&E from scAAVrh74.tMCK.hSGCA-dosed sgca$^{-/-}$ and wild-type mice were sent to a veterinary pathologist for formal review. No adverse effects were noted in any sample from any of the scAAVrh74.tMCK.hSGCA-dosed sgca$^{-/-}$ and wild-type mice. In addition to efficacy, these data demonstrated that the systemic delivery of all three doses of scAAVrh74.tMCK.hSGCA was well-tolerated, safe, and non-toxic to sgca$^{-/-}$ and wild-type mice.

Figure 7A:
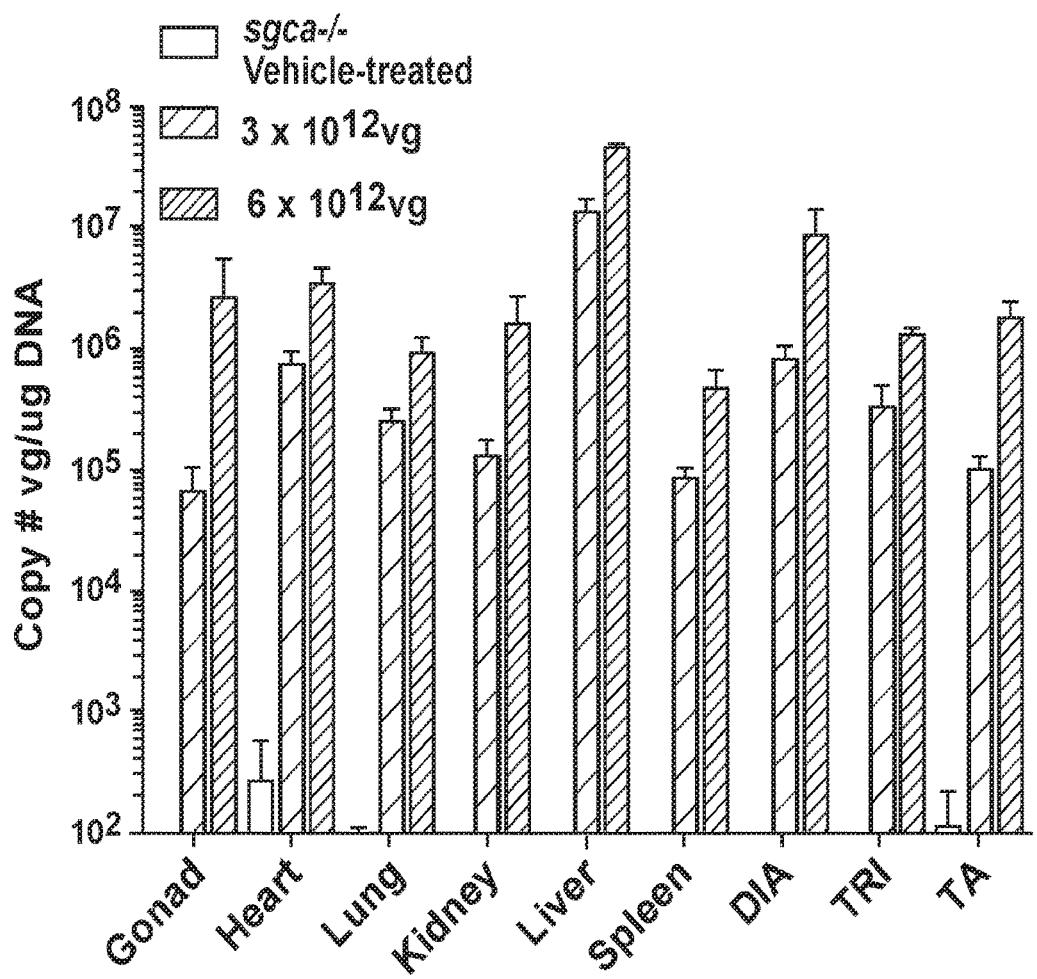
FIG. 7A shows biodistribution analysis of systemic scAAVrh74.tMCK.hSGCA delivery-distribution histogram of mean vg copies of transcript per microgram DNA added to quantitative polymerase chain reaction in various tissues from sgca$^{-/-}$ mice after intravenous delivery of scAAVrh74.tMCK.hSGCA at $3\times10^{12}$ vg and $6\times10^{12}$ vg (or $1\times10^{14}$ vg/kg, and $2\times10^{14}$ vg/kg, respectively, based on a 20-g mouse).
Figure 7B:
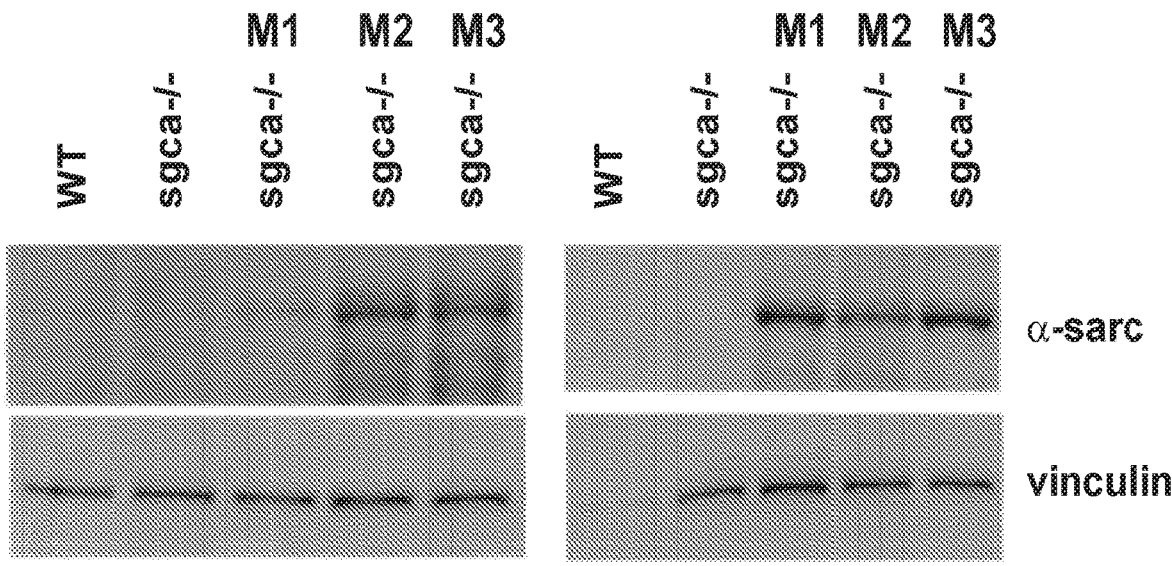
FIG. 7B shows Western blots of alpha-sarcoglycan protein expression in the liver of WT and sgca$^{-/-}$ mice treated with either vehicle (sgca$^{-/-}$ LR (lactate ringer)) or scAArh74.tMCK.hSGCA at $1.0\times10^{12}$ vg (Left Western blot) or $6\times10^{12}$ vg (Right Western blot). Each lane represents an independent mouse (M1: Mouse 1; M2: Mouse 2; M3: Mouse 3). Bottom panel represents vinculin that was used as loading control. Abbreviations: DIA, diaphragm; TA, tibialis anterior; TRI, triceps.

To test for potential toxicity or safety concerns from the delivery of scAAVrh74.tMCK.hSGCA, vector biodistribution quantitative PCR was performed to quantify vector genome presence (FIG. 7A). Vector-specific tMCK.hSGCA primer probe sets were used to detect vector genomes in all muscles and organs tested from the scAAVrh74.tMCK/hSGCA-dosed sgca$^{-/-}$ mice. As expected, vector genomes were present in the tissues tested, with the highest copy number in the liver, followed by muscles. Western blots of alpha-sarcoglycan protein in the liver of WT and sgca–/– mice treated with either vehicle (sgca$^{-/-}$ LR) or scAArh74.tMCK.hSGCA are shown in FIG. 7B.

To improve efficiency of α-SG expression, in one embodiment, the hSGCA cDNA sequence is packaged into a self-complementary vector. Self-complementary AAV vectors contain an inverted repeat genome that promotes the formation of dsDNA, thus allowing replication and transcription to occur without the need for multiple vector genomes to promote these processes. As such, use of self-complementary vectors eliminates the rate-limiting step to allow more rapid expression of the transgene. Applicant has shown that intravascular delivery of scAAVrh74.tMCK.hSGCA in patients with LGMD2D was associated with increased α-SG expression 180 days post-gene transfer at doses of 1×10$^{12}$ and 3×10$^{12}$.

Intravenous delivery of scAAVrh74.tMCK.hSGCA provides muscles with increased strength and resistance against contraction-induced damage in the tibialis anterior and diaphragm muscles in all three vector-treated cohorts compared to vehicle-treated controls. In addition, treatment with scAAVrh74.tMCK.hSGCA resulted in a significant reduction in CK. Moreover, after treatment with scAAVrh74.tMCK.hSGCA, mice were able to ambulate and rear onto hind limbs more frequently than vehicle-treated mice.

Prominent histopathology, which includes centrally located nuclei, wide variability in fiber size, inflammation, necrosis, and fibrosis, is typically observed through muscle biopsies of patients with LGMD2D After hSGCA delivery, mice had a reduction in CN, a more even distribution of myofiber size, and a reduction in collagen content, with muscles having an overall healthier appearance compared to vehicle-treated mice. The total reduction in histopathology and scar tissue was concomitantly associated with improvement in the overall normal function and physiology of the muscles in vector-treated mice.

Finally, safety studies conducted through quantitative PCR, serum chemistry analysis, and histopathology did not review signs of toxicity. The tMCK promoter was detected only in targeted tissues (all muscles) and was absent in other (non-muscle) organs, except for the liver. tMCK detection in the liver is not uncommon or concerning as it is a clearance organ. Histopathology review of all tissues (including liver) by a certified veterinarian pathologist concluded that the systemic delivery of scAAVrh74.tMCK.hSGCA was not only safe in all tissues but also that gene delivery dramatically reduced the amount of dystrophic pathology found in skeletal muscles of vehicle-treated sgca$^{-/-}$ mice. Chemistries performed on blood samples of vector-treated mice also support the lack of toxicity.

The dose-escalation study, as in this disclosure, provides preclinical data to support that the lowest dose systemically tested here, i.e $1\times10^{12}$ vg total ($5\times10^{13}$ vg/kg), is ample to reduce the signs and symptoms associated with loss of α-SG protein. At the lowest dose tested functional improvement in all muscles, as demonstrated by increase in strength and locomotor behavior (ambulation and rearing) was observed in vector-treated mice. Safety studies show no signs of toxicity, even at the highest delivered dose of $6\times10^{12}$ vg total ($2\times10^{14}$ vg/kg).

Example 4

Elder Patients and Durability

The rAAVrh74.tMCK.hSGCA-mediated gene replacement has shown positive results in treating LGMD-2D and other associated diseases. This study was designed to test the ability of rAAVrh74.tMCK.hSGCA to treat older, more severely affected muscle, and to determine the long-term durability of the AAV viral vector.

All procedures were conducted in accordance with approval by the Research Institute at the Nationwide Children's Hospital Institutional Animal Care and Use Committee. Mice were maintained under standardized conditions on a 12:12-hour light:dark cycle, with food and water provided ad libitum. First, rAAVrh74.tMCK.SGCA was systemically administered by tail vein injection to 12-month-old sgca$^{-/-}$ mice (n=5) presenting with severe muscle histopathology at three doses ($1.0\times10^{12}$, $3.0\times10^{12}$, and $6.0\times10^{12}$ vg. The controls included lactated ringers solution (LRS) injected sgca$^{-/-}$ mice (n=5) and LRS injected BL6 wild type mice (n=4). At the 6-month endpoint post treatment, muscle from the treated mice were evaluated for SGCA protein expression, histological rescue, and functional improvement. All three doses showed robust protein expression of α-SG at the sarcolemma, improved histopathology, increased locomotor activity and specific-force generation, protection against eccentric force loss, and reduced serum CK compared with controls. No vector toxicity was detected. In aged mice, treatment resulted in widespread, high-level protein expression in muscles analyzed, reduced fibrosis, and increased resistance to contraction-induced injury in tibialis anterior muscle.

Figure 8:
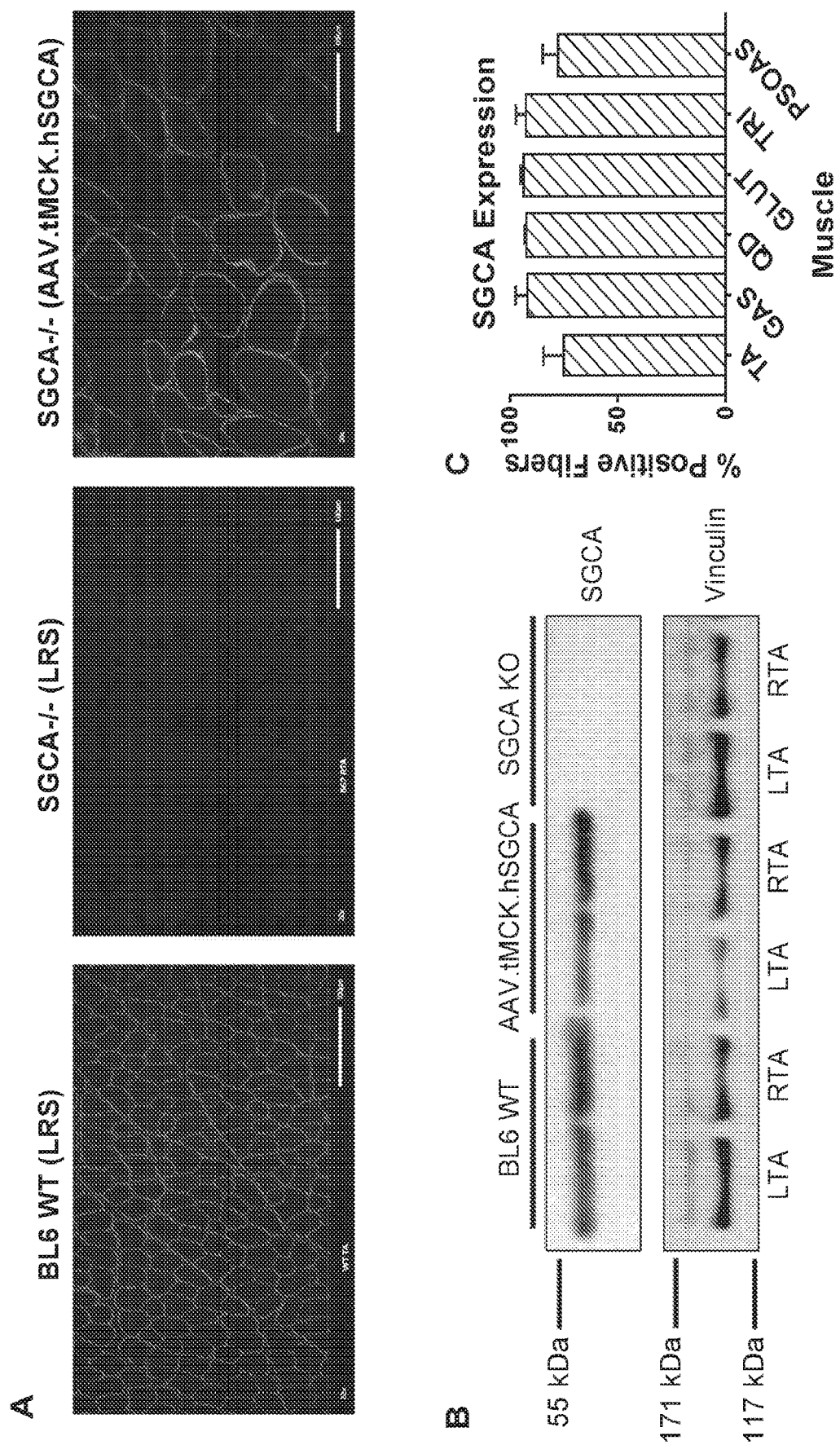
FIG. 8 shows expression of scAAVrh74.tMCK.hSGCA in skeletal muscle of 12-month-old sgca$^{-/-}$ mice by immunofluorescence staining (FIG. 8A) and western blot (FIG. 8B). The graph in FIG. 8C provides the percent positive muscle fibers in the scAAVrh74.tMCK.hSGCA sgca$^{-/-}$ mice. Abbreviations: TA, tibialis anterior; GAS, gastrocnemius; QD, quadricep; GLUT, gluteus; TRI, tricep; PSOAS, psoas major, diaphragm; WT, wild-type, LRS, lactated ringers solution

Particularly, IV administration of rAAVrh74.tMCK.hSGCA to 12-month-old sgca$^{-/-}$ mice resulted in widespread high-level protein expression in muscles throughout the lower limb, upper limb, and proximal torso muscles, including the diaphragm and heart (FIG. 8).

Overall improvement in muscle pathology (FIG. 9a) and reduction in central nucleation was observed after administration of scAAVrh74.tMCK.hSGCA. In addition, average fiber size increased to levels similar to levels in WT fibers in gastrocnemius (GAS) and triceps (TRI) muscles (FIG. 9b) after administration.

Figure 9:
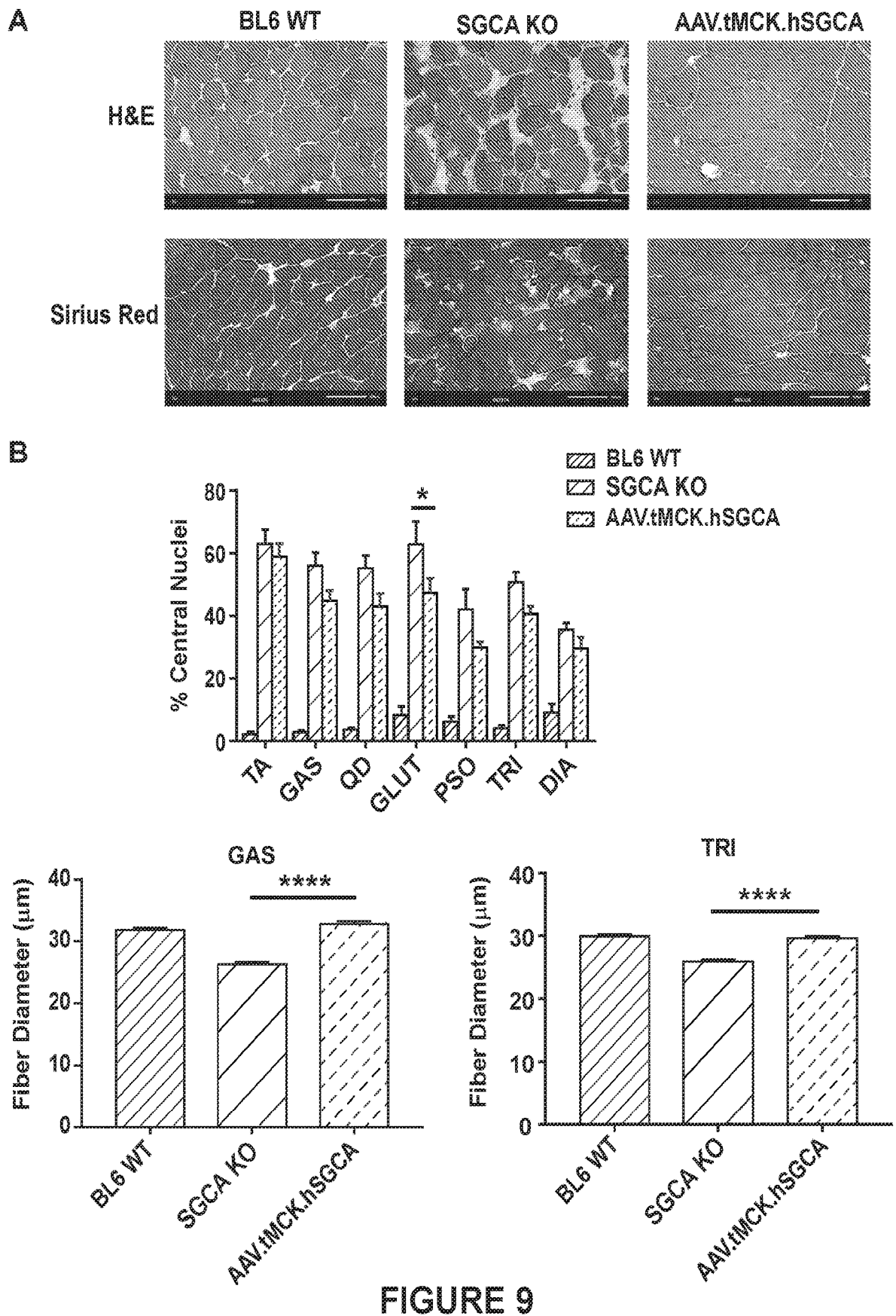
FIG. 9 shows histological results of administering scAAVrh74.tMCK.hSGCA in 12-month-old SGCA$^{-/-}$ mice.
Figure 9:
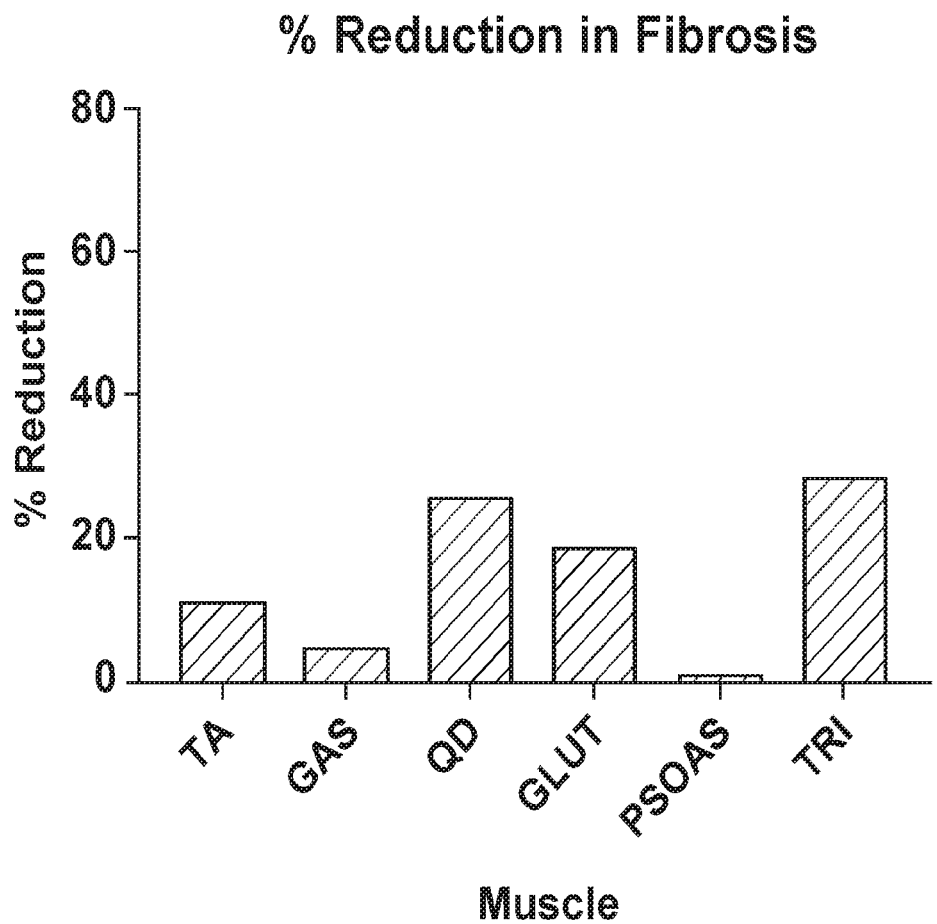
Figure 10:
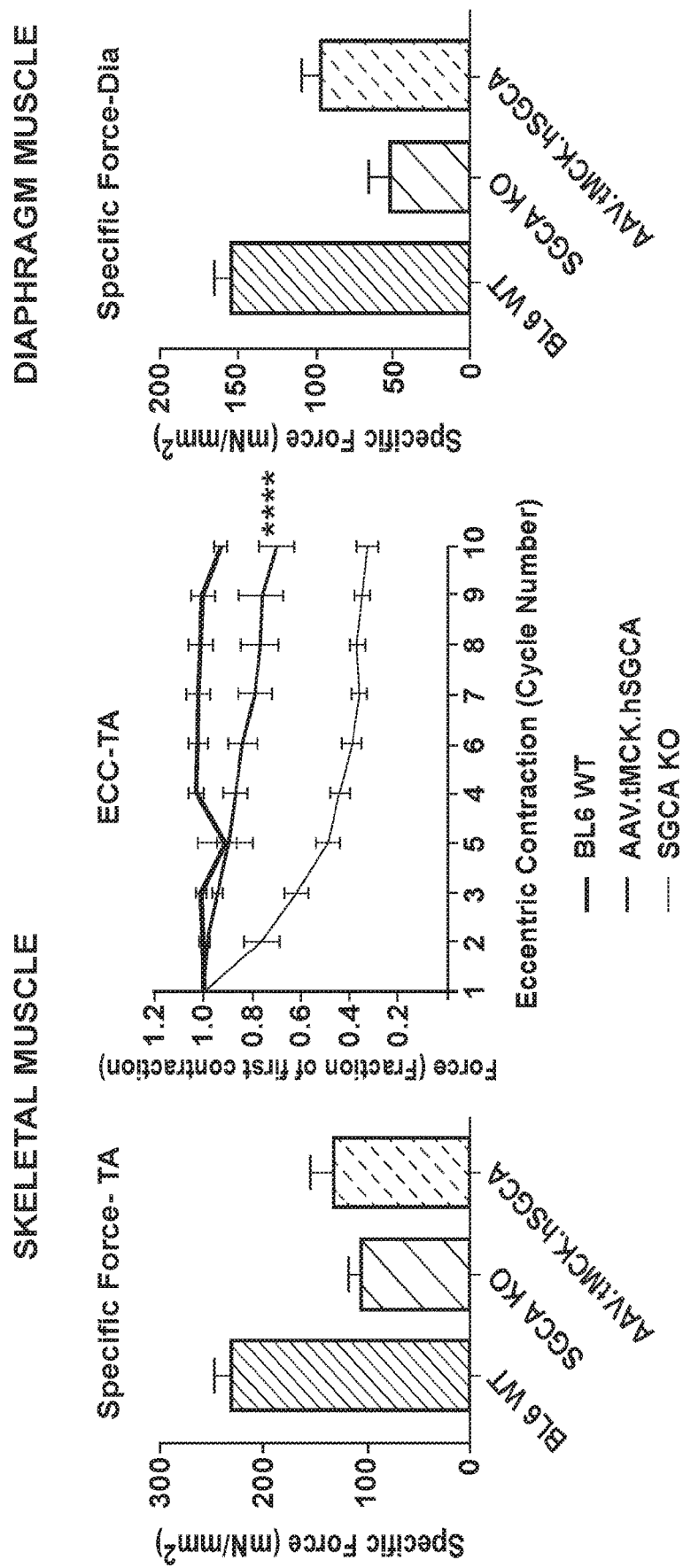
FIG. 10 shows functional improvement in aged mouse after administering scAAVrh74.tMCK.hSGCA.

The level of collagen deposition was quantitated as a measure of fibrosis. Administration of scAAVrh74.tMCK.hSGCA resulted in a reduction in the level of fibrosis compared to untreated controls (FIG. 9c). Functional improvement after administration of scAAVrh74.tMCK.hSGCA was evidenced by improved force output (specific force) in the tibialis anterior (TA) and diaphragm (DIA) muscle and increased resistance to contraction-induced injury in the TA muscle (FIG. 10).

To further investigate the long-term durability of the gene therapy, sgca$^{-/-}$ mice at 4 weeks of age are systemically administered rAAVrh74.tMCK.hSGCA. More than 24 months post-treatment, the vector genome copy numbers are detected with qPCR across all transduced muscles tested (TA, TRI, DIA, GLUT, PSOAS, GAS and QUAD). Protein expression and localization is studied by immunofluorescence staining of treated muscle.

While the present disclosure has been described in terms of specific embodiments, it is understood that variations and modifications will occur to those skilled in the art. Accordingly, only such limitations as appear in the claims should be placed on the disclosure.

All documents referred to in this application are hereby incorporated by reference in their entirety.

```
SGCA cDNA Codon Optimized sequence:
                                                              SEQ ID NO: 1
ATGGCCGAGACACTGTTCTGGACTCCTCTGCTGGTGGTGCTGCTGGCTGGACTGGGAGATACCGAGGCTC

AGCAGACCACACTGCACCCACTGGTGGGCCGGGTGTTCGTGCACACCCTGGACCATGAGACATTTCTGAGT

CTGCCAGAACACGTGGCTGTGCCACCTGCTGTGCATATCACTTACCACGCCCATCTGCAGGGCCATCCTGA

TCTGCCACGGTGGCTGAGATACACCCAGAGATCACCCCACCATCCTGGATTCCTGTATGGAAGCGCTACCC

CAGAGGACAGGGGACTGCAGGTGATCGAAGTGACAGCTTACAACCGCGACAGTTTTGATACTACCAGGCAG

CGCCTGGTGCTGGAGATTGGGGATCCAGAAGGACCCCTGCTGCCTTATCAGGCCGAGTTCCTGGTGCGGT

CACACGACGCTGAGGAAGTGCTGCCATCAACACCCGCCAGCAGATTTCTGTCCGCTCTGGGAGGACTGTG

GGAGCCAGGAGAACTGCAGCTGCTGAATGTGACTAGCGCTCTGGATAGGGGAGGAAGGGTGCCACTGCCA

ATCGAGGGAAGGAAGGAAGGGGTGTACATTAAAGTGGGAAGCGCTTCCCCATTCTCCACCTGCCTGAAGAT

GGTGGCTTCTCCTGATAGTCACGCTAGGTGCGCTCAGGGACAGCCACCACTGCTGTCCTGTTATGACACAC
```

-continued

```
TGGCCCCCCATTTTCGCGTGGACTGGTGCAACGTGACTCTGGTGGATAAATCTGTGCCTGAGCCAGCTGAC

GAAGTGCCAACCCCTGGAGACGGAATCCTGGAGCACGATCCTTTCTTTTGTCCTCCAACAGAAGCCCCAGA

CAGGGATTTCCTGGTGGACGCTCTGGTGACTCTGCTGGTGCCTCTGCTGGTGGCTCTGCTGCTGACCCTGC

TGCTGGCTTATGTGATGTGCTGTCGGAGAGAGGGACGGCTGAAGAGAGACCTGGCCACATCTGATATCCAG

ATGGTGCACCATTGTACTATTCACGGCAACACCGAGGAACTGCGCCAGATGGCTGCTTCTAGGGAGGTGCC

AAGGCCACTGAGTACACTGCCTATGTTTAATGTGCACACTGGCGAACGGCTGCCCCCTAGAGTGGATAGCG

CCCAGGTGCCACTGATTCTGGACCAGCATTGA
```

Human SGCA Protein Sequence:

SEQ ID NO: 2

```
MAETLFWTPLLVVLLAGLGDTEAQQTTLHPLVGRVFVHTLDHETFLSLPEHVAVPPAVHITYHAHLQGHPDLPRW

LRYTQRSPHHPGFLYGSATPEDRGLQVIEVTAYNRDSFDTTRQRLVLEIGDPEGPLLPYQAEFLVRSHDAEEVLP

STPASRFLSALGGLWEPGELQLLNVTSALDRGGRVPLPIEGRKEGVYIKVGSASPFSTCLKMVASPDSHARCAQ

GQPPLLSCYDTLAPHFRVDWCNVTLVDKSVPEPADEVPTPGDiLEHDPFFCPPTEAPDRDFLVDALVTLLLVPLL

VALLLTLLLAYVMCCRREGRLKRDLATSDIQMVHHCTIHGNTEELRQMAASREVPRPLSTLPMFNVHTGERLPPR

VDSAQVPLILDQH*
``` tMCK Promoter Sequence:

SEQ ID NO: 3

```
CCACTACGGGTCTAGGCTGCCCATGTAAGGAGGCAAGGCCTGGGGACACCCGAGATGCCTGGTTATAATTA

ACCCCAACACCTGCTGCCCCCCCCCCCCAACACCTGCTGCCTGAGCCTGAGCGGTTACCCCACCCCGGT

GCCTGGGTCTTAGGCTCTGTACACCATGGAGGAGAAGCTCGCTCTAAAAATAACCCTGTCCCTGGTGGATC

CACTACGGGTCTATGCTGCCCATGTAAGGAGGCAAGGCCTGGGGACACCCGAGATGCCTGGTTATAATTAA

CCCCAACACCTGCTGCCCCCCCCCCCCAACACCTGCTGCCTGAGCCTGAGCGGTTACCCCACCCCGGTG

CCTGGGTCTTAGGCTCTGTACACCATGGAGGAGAAGCTCGCTCTAAAAATAACCCTGTCCCTGGTGGACCA

CTACGGGTCTAGGCTGCCCATGTAAGGAGGCAAGGCCTGGGGACACCCGAGATGCCTGGTTATAATTAACC

CCAACACCTGCTGCCCCCCCCCCCCAACACCTGCTGCCTGAGCCTGAGCGGTTACCCCACCCCGGTGCCT

GGGTCTTAGGCTCTGTACACCATGGAGGAGAAGCTCGCTCTAAAAATAACCCTGTCCCTGGTCCTCCCTGG

GGACAGCCCCTCCTGGCTAGTCACACCCTGTAGGCTCCTCTATATAACCCAGGGGCACAGGGGCTGCCCC

CGGGTCAC
```

AAVrh74-tMCK-SGCA:

SEQ ID NO: 4

```
CTGCGCGCTC GCTCGCTCAC TGAGGCCGCC CGGGCAAAGC CCGGGCGTCG

GGCGACCTTT GGTCGCCCGG CCTCAGTGAG CGAGCGAGCG CGCAGAGAGG

GAGTGGGGTT AACCAATTGG CGGCCGCAAA CTTGCATGCC CCACTACGGG

TCTAGGCTGC CCATGTAAGG AGGCAAGGCC TGGGACACC CGAGATGCCT

GGTTATAATT AACCCCAACA CCTGCTGCCC CCCCCCCCC AACACCTGCT

GCCTGAGCCT GAGCGGTTAC CCCACCCCGG TGCCTGGGTC TTAGGCTCTG

TACACCATGG AGGAGAAGCT CGCTCTAAAA ATAACCCTGT CCCTGGTGGA

TCCACTACGG GTCTATGCTG CCCATGTAAG GAGGCAAGGC CTGGGACAC

CCGAGATGCC TGGTTATAAT TAACCCCAAC ACCTGCTGCC CCCCCCCCC

CAACACCTGC TGCCTGAGCC TGAGCGGTTA CCCCACCCCG GTGCCTGGGT

CTTAGGCTCT GTACACCATG GAGGAGAAGC TCGCTCTAAA ATAACCCTG

TCCCTGGTGG ACCACTACGG GTCTAGGCTG CCCATGTAAG GAGGCAAGGC

CTGGGACAC CCGAGATGCC TGGTTATAAT TAACCCCAAC ACCTGCTGCC
```

-continued

CCCCCCCCCC AACACCTGCT GCCTGAGCCT GAGCGGTTAC CCCACCCCGG

TGCCTGGGTC TTAGGCTCTG TACACCATGG AGGAGAAGCT CGCTCTAAAA

ATAACCCTGT CCCTGGTCCT CCCTGGGGAC AGCCCCTCCT GGCTAGTCAC

ACCCTGTAGG CTCCTCTATA TAACCCAGGG GCACAGGGGC TGCCCCCGGG

TCACCTGCAG AAGTTGGTCG TGAGGCACTG GGCAGGTAAG TATCAAGGTT

ACAAGACAGG TTTAAGGAGA CCAATAGAAA CTGGGCTTGT CGAGACAGAG

AAGACTCTTG CGTTTCTGAT AGGCACCTAT TGGTCTTACT GACATCCACT

TTGCCTTTCT CTCCACAGGT GTCCACTCCC AGTTCAATTA CAGCGCGTGG

TACCACCATG GCCGAGACAC TGTTCTGGAC TCCTCTGCTG GTGGTGCTGC

TGGCTGGACT GGGAGATACC GAGGCTCAGC AGACCACACT GCACCCACTG

GTGGGCCGGG TGTTCGTGCA CACCCTGGAC CATGAGACAT TTCTGAGTCT

GCCAGAACAC GTGGCTGTGC CACCTGCTGT GCATATCACT TACCACGCCC

ATCTGCAGGG CCATCCTGAT CTGCCACGGT GGCTGAGATA CACCCAGAGA

TCACCCCACC ATCCTGGATT CCTGTATGGA AGCGCTACCC CAGAGGACAG

GGGACTGCAG GTGATCGAAG TGACAGCTTA CAACCGCGAC AGTTTTGATA

CTACCAGGCA GCGCCTGGTG CTGGAGATTG GGATCCAGA AGGACCCCTG

CTGCCTTATC AGGCCGAGTT CCTGGTGCGG TCACACGACG CTGAGGAAGT

GCTGCCATCA ACACCCGCCA GCAGATTTCT GTCCGCTCTG GGAGGACTGT

GGGAGCCAGG AGAACTGCAG CTGCTGAATG TGACTAGCGC TCTGGATAGG

GGAGGAAGGG TGCCACTGCC AATCGAGGGA AGGAAGGAAG GGGTGTACAT

TAAAGTGGGA AGCGCTTCCC CATTCTCCAC CTGCCTGAAG ATGGTGGCTT

CTCCTGATAG TCACGCTAGG TGCGCTCAGG GACAGCCACC ACTGCTGTCC

TGTTATGACA CACTGGCCCC CCATTTTCGC GTGGACTGGT GCAACGTGAC

TCTGGTGGAT AAATCTGTGC CTGAGCCAGC TGACGAAGTG CCAACCCCTG

GAGACGGAAT CCTGGAGCAC GATCCTTTCT TTTGTCCTCC AACAGAAGCC

CCAGACAGGG ATTTCCTGGT GGACGCTCTG GTGACTCTGC TGGTGCCTCT

GCTGGTGGCT CTGCTGCTGA CCCTGCTGCT GGCTTATGTG ATGTGCTGTC

GGAGAGAGGG ACGGCTGAAG AGAGACCTGG CCACATCTGA TATCCAGATG

GTGCACCATT GTACTATTCA CGGCAACACC GAGGAACTGC GCCAGATGGC

TGCTTCTAGG GAGGTGCCAA GGCCACTGAG TACACTGCCT ATGTTTAATG

TGCACACTGG CGAACGGCTG CCCCCTAGAG TGGATAGCGC CCAGGTGCCA

CTGATTCTGG ACCAGCATTG AGGCCGCAAT AAAAGATCTT TATTTTCATT

AGATGTGTGT GTTGGTTTTT TGTGTGTCCT GCAGGGCGC GCCTCTAGAG

CATGGCTACG TAGATAAGTA GCATGGCGGG TTAATCATTA ACTACAAGGA

ACCCCTAGTG ATGGAGTTGG CCACTCCCTC TCTGCGCGCT CGCTCGCTCA

CTGAGGCCGG GCGACCAAAG GTCGCCCGAC GCCCGGGCTT TGCCCGGGCG

GCCTCAGTGA GCGAGCGAGC GCGCAG

5'ITR

SEQ ID NO: 5

CTGCGCGCTC GCTCGCTCAC TGAGGCCGCC CGGGCAAAGC CCGGGCGTCG GGCGACCTTT

GGTCGCCCGG CCTCAGTGAG CGAGCGAGCG CGCAGAGAGG GAGTGGGGTT

3'ITR

SEQ ID NO: 6

CCACTCCCTC TCTGCGCGCT CGCTCGCTCA CTGAGGCCGG GCGACCAAAG GTCGCCCGAC

GCCCGGGCTT TGCCCGGGCG GCCTCAGTGA GCGAGCGAGC GCGC

PolyA

SEQ ID NO: 7

GGCCGCAAT AAAAGATCTT TATTTTCATT AGATCTGTGT GTTGGTTTTT TGTG

SEQ ID NO: 8

```
ATGCAGCTGC GCGCTCGCTC GCTCACTGAG GCCGCCCGGG CAAAGCCCGG GCGTCGGGCG   60
ACCTTTGGTC GCCCGGCCTC AGTGAGCGAG CGAGCGCGCA GAGAGGGAGT GGGGTTAACC  120
AATTGGCGGC CGCAAACTTG CATGCCCCAC TACGGGTCTA GGCTGCCCAT GTAAGGAGGC  180
AAGGCCTGGG GACACCCGAG ATGCCTGGTT ATAATTAACC CCAACACCTG CTGCCCCCCC  240
CCCCCCAACA CCTGCTGCCT GAGCCTGAGC GGTTACCCCA CCCCGGTGCC TGGGTCTTAG  300
GCTCTGTACA CCATGGAGGA GAAGCTCGCT CTAAAAATAA CCCTGTCCCT GGTGGATCCA  360
CTACGGGTCT ATGCTGCCCA TGTAAGGAGG CAAGGCCTGG GGACACCCGA GATGCCTGGT  420
TATAATTAAC CCCAACACCT GCTGCCCCCC CCCCCCCAAC ACCTGCTGCC TGAGCCTGAG  480
CGGTTACCCC ACCCCGGTGC CTGGGTCTTA GGCTCTGTAC ACCATGGAGG AGAAGCTCGC  540
TCTAAAAATA ACCCTGTCCC TGGTGGACCA CTACGGGTCT AGGCTGCCCA TGTAAGGAGG  600
CAAGGCCTGG GGACACCCGA GATGCCTGGT TATAATTAAC CCCAACACCT GCTGCCCCCC  660
CCCCCCAACA CCTGCTGCCT GAGCCTGAGC GGTTACCCCA CCCCGGTGCC TGGGTCTTAG  720
GCTCTGTACA CCATGGAGGA GAAGCTCGCT CTAAAAATAA CCCTGTCCCT GGTCCTCCCT  780
GGGGACAGCC CCTCCTGGCT AGTCACACCC TGTAGGCTCC TCTATATAAC CCAGGGGCAC  840
AGGGGCTGCC CCCGGGTCAC CTGCAGAAGT TGGTCGTGAG GCACTGGGCA GGTAAGTATC  900
AAGGTTACAA GACAGGTTTA AGGAGACCAA TAGAAACTGG GCTTGTCGAG ACAGAGAAGA  960
CTCTTGCGTT TCTGATAGGC ACCTATTGGT CTTACTGACA TCCACTTTGC CTTTCTCTCC 1020
ACAGGTGTCC ACTCCCAGTT CAATTACAGC GCGTGGTACC ACCATGGCCG AGACACTGTT 1080
CTGGACTCCT CTGCTGGTGG TGCTGCTGGC TGGACTGGGA GATACCGAGG CTCAGCAGAC 1140
CACACTGCAC CCACTGGTGG GCCGGGTGTT CGTGCACACC CTGGACCATG AGACATTTCT 1200
GAGTCTGCCA GAACACGTGG CTGTGCCACC TGCTGTGCAT ATCACTTACC ACGCCCATCT 1260
GCAGGGCCAT CCTGATCTGC CACGGTGGCT GAGATACACC CAGAGATCAC CCCAGCATCC 1320
TGGATTCCTG TATGGAAGCG CTACCCCAGA GGACAGGGGA CTGCAGGTGA TCGAAGTGAC 1380
AGCTTACAAC CGCGACAGTT TTGATACTAC CAGGCAGCGC CTGGTGCTGG AGATTGGGGA 1440
TCCAGAAGGA CCCCTGCTGC CTTATCAGGC CGAGTTCCTG GTGCGGTCAC ACGACGCTGA 1500
GGAAGTGCTG CCATCAACAC CCGCCAGCAG ATTTCTGTCC GCTCTGGGAG GACTGTGGGA 1560
GCCAGGAGAA CTGCAGCTGC TGAATGTGAC TAGCGCTCTG GATAGGGGAG GAAGGGTGCC 1620
ACTGCCAATC GAGGGAAGGA AGGAAGGGGT GTACATTAAA GTGGGAAGCG CTTCCCCATT 1680
CTCCACCTGC CTGAAGATGG TGGCTTCTCC TGATAGTCAC GCTAGGTGCG CTCAGGGACA 1740
GCCACCACTG CTGTCCTGTT ATGACACACT GGCCCCCCAT TTTCGCGTGG ACTGGTGCAA 1800
CGTGACTCTG GTGGATAAAT CTGTGCCTGA GCCAGCTGAC GAAGTGCCAA CCCCTGGAGA 1860
CGGAATCCTG GAGCACGATC CTTTCTTTTG TCCTCCAACA GAAGCCCCAG ACAGGGATTT 1920
CCTGGTGGAC GCTCTGGTGA CTCTGCTGGT GCCTCTGCTG GTGGCTCTGC TGCTGACCCT 1980
GCTGCTGGCT TATGTGATGT GCTGTCGGAG AGAGGGACGG CTGAAGAGAG ACCTGGCCAC 2040
ATCTGATATC CAGATGGTGC ACCATTGTAC TATTCACGGC AACACCGAGG AACTGCGCCA 2100
```

-continued

```
GATGGCTGCT TCTAGGGAGG TGCCAAGGCC ACTGAGTACA CTGCCTATGT TTAATGTGCA 2160

CACTGGCGAA CGGCTGCCCC CTAGAGTGGA TAGCGCCCAG GTGCCACTGA TTCTGGACCA 2220

GCATTGAGGC CGCAATAAAA GATCTTTATT TTCATTAGAT CTGTGTGTTG GTTTTTTGTG 2280

TGTCCTGCAG GGGCGCGCCT CTAGAGCATG GCTACGTAGA TAAGTAGCAT GGCGGGTTAA 2340

TCATTAACTA CAAGGAACCC CTAGTGATGG AGTTGGCCAC TCCCTCTCTG CGCGCTCGCT 2400

CGCTCACTGA GGCCGGGCGA CCAAAGGTCG CCCGACGCCC GGGCTTTGCC CGGGCGGCCT 2460

CAGTGAGCGA GCGAGCGCGC AGCTGGCGTA ATAGCGAAGA GGCCCGCACC GATCGCCCTT 2520

CCCAACAGTT GCGCAGCCTG AATGGCGAAT GGCGATTCCG TTGCAATGGC TGGCGGTAAT 2580

ATTGTTCTGG ATATTACCAG CAAGGCCGAT AGTTTGAGTT CTTCTACTCA GGCAAGTGAT 2640

GTTATTACTA ATCAAAGAAG TATTGCGACA ACGGTTAATT TGCGTGATGG ACAGACTCTT 2700

TTACTCGGTG GCCTCACTGA TTATAAAAAC ACTTCTCAGG ATTCTGGCGT ACCGTTCCTG 2760

TCTAAAATCC CTTTAATCGG CCTCCTGTTT AGCTCCCGCT CTGATTCTAA CGAGGAAAGC 2820

ACGTTATACG TGCTCGTCAA AGCAACCATA GTACGCGCCC TGTAGCGGCG CATTAAGCGC 2880

GGCGGGTGTG GTGGTTACGC GCAGCGTGAC CGCTACACTT GCCAGCGCCC TAGCGCCCGC 2940

TCCTTTCGCT TTCTTCCCTT CCTTTCTCGC CACGTTCGCC ATCTTCAAAT ATGTATCCGC 3000

TCATGAGACA ATAACCCTGA TAAATGCTTC AATAATATTG AAAAGGAAG AGTCCTGAGG 3060

CGGAAAGAAC CAGCTGTGGA ATGTGTGTCA GTTAGGGTGT GGAAAGTCCC CAGGCTCCCC 3120

AGCAGGCAGA AGTATGCAAA GCATGCATCT CAATTAGTCA GCAACCAGGT GTGGAAAGTC 3180

CCCAGGCTCC CCAGCAGGCA GAAGTATGCA AAGCATGCAT CTCAATTAGT CAGCAACCAT 3240

AGTCCCGCCC CTAACTCCGC CCATGGCTG ACTAATTTTT TTTATTTATG CAGAGGCCGA 3300

GGCCGCCTCG GCCTCTGAGC TATTCCAGAA GTAGTGAGGA GGCTTTTTTG GAGGCCTAGG 3360

CTTTTGCAAA GATCGATCAA GAGACAGGAT GAGGATCGTT TCGCATGATT GAACAAGATG 3420

GATTGCACGC AGGTTCTCCG GCCGCTTGGG TGGAGAGGCT ATTCGGCTAT GACTGGGCAC 3430

AACAGACAAT CGGCTGCTCT GATGCCGCCG TGTTCCGGCT GTCAGCGCAG GGCGCCCGG 3540

TTCTTTTTGT CAAGACCGAC CTGTCCGGTG CCCTGAATGA ACTGCAAGAC GAGGCAGCGC 3600

GGCTATCGTG GCTGGCCACG ACGGGCGTTC CTTGCGCAGC TGTGCTCGAC GTTGTCACTG 3660

AAGCGGGAAG GGACTGGCTG CTATTGGGCG AAGTGCCGGG GCAGGATCTC CTGTCATCTC 3720

ACCTTGCTCC TGCCGAGAAA GTATCCATCA TGGCTGATGC AATGCGGCGG CTGCATACGC 3780

TTGATCCGGC TACCTGCCCA TTCGACCACC AAGCGAAACA TCGCATCGAG CGAGCACGTA 3840

CTCGGATGGA AGCCGGTCTT GTCGATCAGG ATGATCTGGA CGAAGAGCAT CAGGGGCTCG 3900

CGCCAGCCGA ACTGTTCGCC AGGCTCAAGG CGAGCATGCC CGACGGCGAG GATCTCGTCG 3960

TGACCCATGG CGATGCCTGC TTGCCGAATA TCATGGTGGA AAATGGCCGC TTTTCTGGAT 4020

TCATCGACTG TGGCCGGCTG GGTGTGGCGG ACCGCTATCA GGACATAGCG TTGGCTACCC 4080

GTGATATTGC TGAAGAGCTT GGCGGCGAAT GGGCTGACCG CTTCCTCGTG CTTTACGGTA 4140

TCGCCGCTCC CGATTCGCAG CGCATCGCCT TCTATCGCCT TCTTGACGAG TTCTTCTGAG 4200

CGGGACTCTG GGGTTCGAAA TGACCGACCA AGCGACGCCC AACCTGCCAT CACGAGATTT 4260

CGATTCCACC GCCGCCTTCT ATGAAAGGTT GGGCTTCGGA ATCGTTTTCC GGGACGCCGG 4320

CTGGATGATC CTCCAGCGCG GGATCTCAT GCTGGAGTTC TTCGCCCACC CTAGGGGGAG 4380

GCTAACTGAA ACACGGAAGG AGACAATACC GGAAGGAACC CGCGCTATGA CGGCAATAAA 4440

AAGACAGAAT AAAACGTTG CGCAAACTAT TAACTGGCGA ACTACTTACT CTAGCTTCCC 4500

GGCAACAATT AATAGACTGG ATGGAGGCGG ATAAAGTTGC AGGACCACTT CTGCGCTCGG 4560
```

-continued

```
CCCTTCCGGC TGGCTGGTTT ATTGCTGATA AATCTGGAGC CGGTGAGCGT GGGTCTCGCG   4620
GTATCATTGC AGCACTGGGG CCAGATGGTA AGCCCTCCCG TATCGTAGTT ATCTACACGA   4680
CGGGGAGTCA GGCAACTATG GATGAACGAA ATAGACAGAT CGCTGAGATA GGTGCCTCAC   4740
TGATTAAGCA TTGGTAACTG TCAGACCAAG TTTACTCATA TATACTTTAG ATTGATTTAA   4800
AACTTCATTT TTAATTTAAA AGGATCTAGG TGAAGATCCT TTTTGATAAT CTCATGACCA   4860
AAATCCCTTA ACGTGAGTTT TCGTTCCACT GAGCGTCAGA CCCCGTAGAA AAGATCAAAG   4920
GATCTTCTTG AGATCCTTTT TTTCTGCGCG TAATCTGCTG CTTGCAAACA AAAAAACCAC   4980
CGCTACCAGC GGTGGTTTGT TTGCCGGATC AAGAGCTACC AACTCTTTTT CCGAAGGTAA   5040
CTGGCTTCAG CAGAGCGCAG ATACCAAATA CTGTTCTTCT AGTGTAGCCG TAGTTAGGCC   5100
ACCAGTTCAA GAACTCTGTA GCACCGCCTA CATACCTCGC TCTGCTAATC CTGTTACCAG   5160
TGGCTGCTGC CAGTGGCGAT AAGTCGTGTC TTACCGGGTT GGACTCAAGA CGATAGTTAC   5220
CGGATAAGGC GCAGCGGTCG GGCTGAACGG GGGGTTCGTG CACACAGCCC AGCTTGGAGC   5280
GAACGACCTA CACCGAACTG AGATACCTAC AGCGTGAGCT ATGAGAAAGC GCCACGCTTC   5340
CCGAAGGGAG AAAGGCGGAC AGGTATCCGG TAAGCGGCAG GGTCGGAACA GGAGAGCGCA   5400
CGAGGGAGCT TCCAGGGGGA AACGCCTGGT ATCTTTATAG TCCTGTCGGG TTTCGCCACC   5460
TCTGACTTGA GCGTCGATTT TTGTGATGCT CGTCAGGGGG GCGGAGCCTA TGGAAAAACG   5520
CCAGCAACGC GGCCTTTTTA CGGTTCCTGG CCTTTTGCTG GCCTTTTGCT CACATGTTCT   5580
TTCCTGCGTT ATCCCCTGAT TCTGTGGATA ACCGTATTAC CGCCTTTGAG TGAGCTGATA   5640
CCGCTCGCCG CAGCCGAACG ACCGAGCGCA GCGAGTCAGT GAGCGAGGAA GCGGAAGAGC   5700
GCCCAATACG CAAACCGCCT CTCCCCGCGC GTTGGCCGAT TCATTAATG              5749
```

What is claimed is:

1. A method of treating limb-girdle muscular dystrophy type 2D (LGMD2D) in a subject in need thereof comprising the step of intravenously administering a recombinant adeno-associated virus (rAAV), wherein the rAAV is administered using a systemic route of administration at a dose of about $5\times10^{13}$ vg/kg to about $2\times10^{14}$ vg/kg based on a supercoiled DNA or plasmid as the quantitation standard, and wherein the rAAV comprises a nucleotide sequence with at least 90%, 91%, 92%, 93%, 94%, 95%, 96%, 97%, 98%, or 99% identity to SEQ ID NO: 4 and said nucleotide sequence encodes a protein that retains alpha-sarcoglycan activity, wherein the percentage identity is determined by aligning the sequence information with BLAST as the alignment tool.

2. The method of claim 1, wherein the rAAV is administered at a dose of about $5\times10^{13}$ vg/kg, about $1\times10^{14}$ vg/kg, or about $2\times10^{14}$ vg/kg based on a supercoiled DNA or plasmid as the quantitation standard.

3. A method of treating limb-girdle muscular dystrophy type 2D (LGMD2D) in a subject in need thereof comprising the step of intravenously administering a recombinant adeno-associated virus (rAAV), wherein the rAAV is administered using a systemic route of administration at a dose of about $1.0\times10^{13}$ vg/kg to about $8.0\times10^{13}$ vg/kg based on a linearized DNA or plasmid as the quantitation standard, and wherein the rAAV comprises a nucleotide sequence with at least 90%, 91%, 92%, 93%, 94%, 95%, 96%, 97%, 98%, or 99% identity to SEQ ID NO: 4 and said nucleotide sequence encodes a protein that retains alpha-sarcoglycan activity, wherein the percentage identity is determined by aligning the sequence information with BLAST as the alignment tool.

4. The method of claim 3, wherein level of alpha-sarcoglycan gene expression in a skeletal muscle cell of the subject is increased after administration of the rAAV as compared to the level of alpha-sarcoglycan gene expression before administration of the rAAV; wherein serum CK level in the subject is decreased after administration of the rAAV as compared to serum CK level before administration of the rAAV; wherein locomotor activity and specific-force generation are increased; wherein fibrosis is reduced; wherein resistance to contraction-induced injury in tibialis anterior muscle is increased; and/or wherein number of alpha-sarcoglycan positive fibers in the muscle tissue of the subject is increased after administration of the rAAV as compared to the number of alpha-sarcoglycan positive fibers before administration of the rAAV.

5. The method of claim 3, wherein level of alpha-sarcoglycan gene expression in a skeletal muscle cell of the subject is increased after administration of the rAAV as compared to the level of alpha-sarcoglycan gene expression before administration of the rAAV.

6. The method of claim 5, wherein the alpha-sarcoglycan gene expression is detected by measuring the alpha-sarcoglycan protein level by Western blot, and/or immunohistochemistry.

7. The method of claim 3, wherein fibrosis of the skeletal muscle is reduced in the subject after administration of the rAAV as compared to before administration of the rAAV.

8. The method of claim 7, wherein the fibrosis, central nucleation, creatine kinase (CK) level, and/or collagen deposition in the skeletal muscle in the subject is reduced after administration of the rAAV as compared to before administration of the rAAV.

9. The method of claim 3, wherein specific force, fiber diameter size, and/or eccentric contraction in the muscle of the subject are increased after administration of the rAAV as compared to before administration of the rAAV.

10. The method of claim 3, wherein the subject is a human subject is 4 to 15 years of age, 25 to 55 years of age, or over 50 years of age.

11. The method of claim 3, wherein the subject is a human subject that is 4-15 years of age, has a confirmed alpha-sarcoglycan (SGCA) mutation in both alleles, and/or was negative for AAVrh74 antibodies.

12. The method of claim 3, wherein the dose is $1.85\times10^{13}$ vg/kg based on a linearized DNA or plasmid as the quantification method.

13. The method of claim 3, wherein the dose is $7.41\times10^{13}$ vg/kg based on a linearized DNA or plasmid as the quantification method.

* * * * *

SEQUENCE LISTING

<160> NUMBER OF SEQ ID NOS: 14

<210> SEQ ID NO 1
<211> LENGTH: 1164
<212> TYPE: DNA
<213> ORGANISM: Homo Sapiens

<400> SEQUENCE: 1

```
atggccgaga cactgttctg gactcctctg ctggtggtgc tgctggctgg actgggagat     60
accgaggctc agcagaccac actgcaccca ctggtgggcc gggtgttcgt gcacaccctg    120
gaccatgaga catttctgag tctgccagaa cacgtggctg tgccacctgc tgtgcatatc    180
acttaccacg cccatctgca gggccatcct gatctgccac ggtggctgag atacacccag    240
agatcacccc accatcctgg attcctgtat ggaagcgcta ccccagagga caggggactg    300
caggtgatcg aagtgacagc ttacaaccgc gacagttttg atactaccag gcagcgcctg    360
gtgctggaga ttggggatcc agaaggaccc ctgctgcctt atcaggccga gttcctggtg    420
cggtcacacg acgctgagga agtgctgcca tcaacacccg ccagcagatt tctgtccgct    480
ctgggaggac tgtgggagcc aggagaactg cagctgctga atgtgactag cgctctggat    540
aggggaggaa gggtgccact gccaatcgag ggaaggaagg aagggtgta cattaaagtg    600
ggaagcgctt ccccattctc cacctgcctg aagatggtgg cttctcctga tagtcacgct    660
aggtgcgctc agggacagcc accactgctg tcctgttatg acacactggc ccccatttt    720
cgcgtggact ggtgcaacgt gactctggtg gataaatctg tgcctgagcc agctgacgaa    780
```

```
gtgccaaccc ctggagacgg aatcctggag cacgatcctt tcttttgtcc tccaacagaa    840
gccccagaca gggatttcct ggtggacgct ctggtgactc tgctggtgcc ctgctggtg     900 gctctgctgc tgaccctgct gctggcttat gtgatgtgct gtcggagaga gggacggctg    960
aagagagacc tggccacatc tgatatccag atggtgcacc attgtactat tcacggcaac   1020
accgaggaac tgcgccagat ggctgcttct agggaggtgc caaggccact gagtacactg   1080
cctatgttta atgtgcacac tggcgaacgg ctgcccccta gagtggatag cgcccaggtg   1140
ccactgattc tggaccagca ttga                                          1164
```

<210> SEQ ID NO 2
<211> LENGTH: 387
<212> TYPE: PRT
<213> ORGANISM: Homo Sapiens

<400> SEQUENCE: 2

```
Met Ala Glu Thr Leu Phe Trp Thr Pro Leu Val Val Leu Leu Ala
1               5                   10                  15

Gly Leu Gly Asp Thr Glu Ala Gln Gln Thr Thr Leu His Pro Leu Val
            20                  25                  30

Gly Arg Val Phe Val His Thr Leu Asp His Glu Thr Phe Leu Ser Leu
        35                  40                  45

Pro Glu His Val Ala Val Pro Pro Ala Val His Ile Thr Tyr His Ala
    50                  55                  60

His Leu Gln Gly His Pro Asp Leu Pro Arg Trp Leu Arg Tyr Thr Gln
65                  70                  75                  80

Arg Ser Pro His His Pro Gly Phe Leu Tyr Gly Ser Ala Thr Pro Glu
                85                  90                  95

Asp Arg Gly Leu Gln Val Ile Glu Val Thr Ala Tyr Asn Arg Asp Ser
            100                 105                 110

Phe Asp Thr Thr Arg Gln Arg Leu Val Leu Glu Ile Gly Asp Pro Glu
        115                 120                 125

Gly Pro Leu Leu Pro Tyr Gln Ala Glu Phe Leu Val Arg Ser His Asp
    130                 135                 140

Ala Glu Glu Val Leu Pro Ser Thr Pro Ala Ser Arg Phe Leu Ser Ala
145                 150                 155                 160

Leu Gly Gly Leu Trp Glu Pro Gly Glu Leu Gln Leu Leu Asn Val Thr
                165                 170                 175

Ser Ala Leu Asp Arg Gly Gly Arg Val Pro Leu Pro Ile Glu Gly Arg
            180                 185                 190

Lys Glu Gly Val Tyr Ile Lys Val Gly Ser Ala Ser Pro Phe Ser Thr
        195                 200                 205

Cys Leu Lys Met Val Ala Ser Pro Asp Ser His Ala Arg Cys Ala Gln
    210                 215                 220

Gly Gln Pro Pro Leu Leu Ser Cys Tyr Asp Thr Leu Ala Pro His Phe
225                 230                 235                 240

Arg Val Asp Trp Cys Asn Val Thr Leu Val Asp Lys Ser Val Pro Glu
                245                 250                 255

Pro Ala Asp Glu Val Pro Thr Pro Gly Asp Gly Ile Leu Glu His Asp
            260                 265                 270

Pro Phe Phe Cys Pro Pro Thr Glu Ala Pro Asp Arg Asp Phe Leu Val
        275                 280                 285

Asp Ala Leu Val Thr Leu Leu Val Pro Leu Leu Val Ala Leu Leu Leu
    290                 295                 300
```

```
Thr Leu Leu Leu Ala Tyr Val Met Cys Cys Arg Arg Glu Gly Arg Leu
305                 310                 315                 320

Lys Arg Asp Leu Ala Thr Ser Asp Ile Gln Met Val His His Cys Thr
                325                 330                 335

Ile His Gly Asn Thr Glu Glu Leu Arg Gln Met Ala Ala Ser Arg Glu
            340                 345                 350

Val Pro Arg Pro Leu Ser Thr Leu Pro Met Phe Asn Val His Thr Gly
        355                 360                 365

Glu Arg Leu Pro Pro Arg Val Asp Ser Ala Gln Val Pro Leu Ile Leu
    370                 375                 380

Asp Gln His
385

<210> SEQ ID NO 3
<211> LENGTH: 714
<212> TYPE: DNA
<213> ORGANISM: Artificial Sequence
<220> FEATURE:
<223> OTHER INFORMATION: Synthetic Polypeptide

<400> SEQUENCE: 3
ccactacggg tctaggctgc ccatgtaagg aggcaaggcc tggggacacc cgagatgcct      60
ggttataatt aaccccaaca cctgctgccc ccccccccc aacacctgct gcctgagcct     120
gagcggttac cccaccccgg tgcctgggtc ttaggctctg tacaccatgg aggagaagct     180
cgctctaaaa ataaccctgt ccctggtgga tccactacgg gtctatgctg cccatgtaag     240
gaggcaaggc ctggggacac ccgagatgcc tggttataat taaccccaac acctgctgcc     300
cccccccccc caacacctgc tgcctgagcc tgagcggtta ccccaccccg gtgcctgggt     360
cttaggctct gtacaccatg gaggagaagc tcgctctaaa ataaccctg tccctggtgg     420 accactacgg gtctaggctg cccatgtaag gaggcaaggc ctggggacac ccgagatgcc     480
tggttataat taaccccaac acctgctgcc cccccccccc aacacctgct gcctgagcct     540
gagcggttac cccaccccgg tgcctgggtc ttaggctctg tacaccatgg aggagaagct     600
cgctctaaaa ataaccctgt ccctggtcct ccctggggac agcccctcct ggctagtcac     660
accctgtagg ctcctctata aacccaggg gcacaggggc tgccccggg tcac              714

<210> SEQ ID NO 4
<211> LENGTH: 2476
<212> TYPE: DNA
<213> ORGANISM: Artificial Sequence
<220> FEATURE:
<223> OTHER INFORMATION: Synthetic Polypeptide

<400> SEQUENCE: 4
ctgcgcgctc gctcgctcac tgaggccgcc cgggcaaagc ccgggcgtcg ggcgaccttt      60
ggtcgcccgg cctcagtgag cgagcgagcg cgcagagagg gagtgggtt aaccaattgg     120 cggccgcaaa cttgcatgcc ccactacggg tctaggctgc ccatgtaagg aggcaaggcc     180
tggggacacc cgagatgcct ggttataatt aaccccaaca cctgctgccc ccccccccc     240 aacacctgct gcctgagcct gagcggttac cccaccccgg tgcctgggtc ttaggctctg     300
tacaccatgg aggagaagct cgctctaaaa ataaccctgt ccctggtgga tccactacgg     360
gtctatgctg cccatgtaag gaggcaaggc ctggggacac ccgagatgcc tggttataat     420
taaccccaac acctgctgcc cccccccccc aacacctgc tgcctgagcc tgagcggtta     480
```

```
cccccacccccg gtgcctgggt cttaggctct gtacaccatg gaggagaagc tcgctctaaa    540
aataaccctg tccctggtgg accactacgg gtctaggctg cccatgtaag gaggcaaggc      600
ctggggacac ccgagatgcc tggttataat taaccccaac acctgctgcc cccccccccc     660
aacacctgct gcctgagcct gagcggttac cccaccccgg tgcctgggtc ttaggctctg      720
tacaccatgg aggagaagct cgctctaaaa ataaccctgt ccctggtcct ccctggggac     780
agccctcct ggctagtcac accctgtagg ctcctctata taacccaggg gcacaggggc      840
tgcccccggg tcacctgcag aagttggtcg tgaggcactg ggcaggtaag tatcaaggtt     900
acaagacagg tttaaggaga ccaatagaaa ctgggcttgt cgagacagag aagactcttg     960
cgtttctgat aggcacctat tggtcttact gacatccact ttgcctttct ctccacaggt   1020
gtccactccc agttcaatta cagcgcgtgg taccaccatg gccgagacac tgttctggac   1080
tcctctgctg gtggtgctgc tggctggact gggagatacc gaggctcagc agaccacact   1140
gcacccactg gtgggccggg tgttcgtgca caccctggac catgagacat ttctgagtct   1200
gccagaacac gtggctgtgc cacctgctgt gcatatcact taccacgccc atctgcaggg   1260
ccatcctgat ctgccacggt ggctgagata cacccagaga tcaccccacc atcctggatt   1320
cctgtatgga agcgctaccc cagaggacag gggactgcag gtgatcgaag tgacagctta   1380
caaccgcgac agttttgata ctaccaggca gcgcctggtg ctggagattg gggatccaga   1440
aggacccctg ctgccttatc aggccgagtt cctggtgcgg tcacgacg ctgaggaagt    1500
gctgccatca acacccgcca gcagatttct gtccgctctg ggaggactgt gggagccagg   1560
agaactgcag ctgctgaatg tgactagcgc tctggatagg ggaggaaggg tgccactgcc   1620
aatcgaggga aggaaggaag gggtgtacat taaagtggga agcgcttccc cattctccac   1680
ctgcctgaag atggtggctt ctcctgatag tcacgctagg tgcgctcagg acagccacc    1740
actgctgtcc tgttatgaca cactggcccc ccatttcgc gtggactggt gcaacgtgac    1800
tctggtggat aaatcgtgc ctgagccagc tgacgaagtg ccaacccctg agacggaat     1860
cctggagcac gatcctttct tttgtcctcc aacagaagcc ccagacaggg atttcctggt   1920
ggacgctctg gtgactctgc tggtgcctct gctggtggct ctgctgctga ccctgctgct   1980
ggcttatgtg atgtgctgtc ggagagaggg acggctgaag agagacctgg ccacatctga   2040
tatccagatg gtgcaccatt gtactattca cggcaacacc gaggaactgc gccagatggc   2100
tgcttctagg gaggtgccaa ggccactgag tacactgcct atgtttaatg tgcacactgg   2160
cgaacggctg ccccctagag tggatagcgc ccaggtgcca ctgattctgg accagcattg   2220
aggccgcaat aaaagatctt tatttttcatt agatctgtgt gttggttttt tgtgtgtcct   2280
gcaggggcgc gcctctagag catggctacg tagataagta gcatggcggg ttaatcatta   2340
actacaagga acccctagtg atggagttgg ccactccctc tctgcgcgct cgctcgctca   2400
ctgaggccgg gcgaccaaag gtcgcccgac gcccgggctt gcccgggcg gcctcagtga   2460
gcgagcgagc gcgcag                                                    2476
```

<210> SEQ ID NO 5
<211> LENGTH: 110
<212> TYPE: DNA
<213> ORGANISM: Artificial Sequence
<220> FEATURE:
<223> OTHER INFORMATION: Synthetic Polypeptide

<400> SEQUENCE: 5

```
ctgcgcgctc gctcgctcac tgaggccgcc cgggcaaagc ccgggcgtcg ggcgaccttt     60
```

```
ggtcgcccgg cctcagtgag cgagcgagcg cgcagagagg gagtgggtt          110
```

<210> SEQ ID NO 6
<211> LENGTH: 104
<212> TYPE: DNA
<213> ORGANISM: Artificial Sequence
<220> FEATURE:
<223> OTHER INFORMATION: Synthetic Polypeptide

<400> SEQUENCE: 6

```
ccactccctc tctgcgcgct cgctcgctca ctgaggccgg gcgaccaaag gtcgcccgac   60
gcccgggctt tgcccgggcg gcctcagtga gcgagcgagc gcgc                   104
```

<210> SEQ ID NO 7
<211> LENGTH: 53
<212> TYPE: DNA
<213> ORGANISM: Artificial Sequence
<220> FEATURE:
<223> OTHER INFORMATION: Synthetic Polypeptide

<400> SEQUENCE: 7

```
ggccgcaata aagatctttt attttcatta gatctgtgtg ttggtttttt gtg         53
```

<210> SEQ ID NO 8
<211> LENGTH: 5749
<212> TYPE: DNA
<213> ORGANISM: Artificial Sequence
<220> FEATURE:
<223> OTHER INFORMATION: Synthetic Polypeptide

<400> SEQUENCE: 8

```
atgcagctgc gcgctcgctc gctcactgag gccgccgggc aaagcccgg gcgtcgggcg    60 acctttggtc gccggcctc agtgagcgag cgagcgcgca gagggagt ggggttaacc    120 aattggcggc cgcaaacttg catgcccac tacgggtcta ggctgccat gtaaggaggc    180 aaggcctggg gacacccgag atgcctggtt ataattaacc ccaacacctg ctgcccccccc    240 cccccccaaca cctgctgcct gagcctgagc ggttaccccca ccccggtgcc tgggtcttag    300
gctctgtaca ccatggagga gaagctcgct ctaaaaataa ccctgtccct ggtggatcca    360
ctacgggtct atgctgccca tgtaaggagg caaggcctgg ggacacccga gatgcctggt    420
tataattaac cccaacacct gctgcccccc cccccccaac cctgctgcc tgagcctgag    480 cggttacccc accccggtgc ctgggtctta ggctctgtac accatggagg agaagctcgc    540
tctaaaaata accctgtccc tggtggacca ctacgggtct aggctgccca tgtaaggagg    600
caaggcctgg ggacacccga gatgcctggt tataattaac cccaacacct gctgccccccc    660 cccccccaaca cctgctgcct gagcctgagc ggttaccccca ccccggtgcc tgggtcttag    720
gctctgtaca ccatggagga gaagctcgct ctaaaaataa ccctgtccct ggtcctccct    780
ggggacagcc cctcctggct agtcacaccc tgtaggctcc tctatataac caggggcac    840 aggggctgcc cccgggtcac ctgcagaagt tggtcgtgag gcactgggca ggtaagtatc    900
aaggttacaa gacaggttta aggagaccaa tagaaactgg gcttgtcgag acagagaaga    960
ctcttgcgtt tctgataggc accttattggt cttactgaca tccactttgc ctttctctcc    1020
acaggtgtcc actcccagtt caattacagc gcgtggtacc accatggccg agacactgtt    1080
ctggactcct ctgctggtgg tgctgctggc tggactggga gataccgagg ctcagcagac    1140
cacactgcac ccactggtgg gccgggtgtt cgtgcacacc ctggaccatg agacatttct    1200
```

```
gagtctgcca gaacacgtgg ctgtgccacc tgctgtgcat atcacttacc acgcccatct    1260
gcagggccat cctgatctgc cacggtggct gagatacacc cagagatcac cccaccatcc    1320
tggattcctg tatggaagcg ctaccccaga ggacagggga ctgcaggtga tcgaagtgac    1380
agcttacaac cgcgacagtt ttgatactac caggcagcgc ctggtgctgg agattgggga    1440
tccagaagga cccctgctgc cttatcaggc cgagttcctg gtgcggtcac acgacgctga    1500
ggaagtgctg ccatcaacac ccgccagcag atttctgtcc gctctgggag gactgtggga    1560
gccaggagaa ctgcagctgc tgaatgtgac tagcgctctg atagggagg aagggtgcc    1620 actgccaatc gagggaagga aggaagggt gtacattaaa gtgggaagcg cttccccatt    1680
ctccacctgc ctgaagatgg tggcttctcc tgatagtcac gctaggtgcg ctcagggaca    1740
gccaccactg ctgtcctgtt atgacacact ggccccccat tttcgcgtgg actggtgcaa    1800
cgtgactctg gtggataaat ctgtgcctga gccagctgac gaagtgccaa ccctggaga    1860 cggaatcctg gagcacgatc ctttcttttg tcctccaaca gaagcccag acagggattt    1920 cctggtggac gctctggtga ctctgctggt gcctctgctg gtggctctgc tgctgaccct    1980
gctgctggct tatgtgatgt gctgtcggag agagggacgg ctgaagagag acctggccac    2040
atctgatatc cagatggtgc accattgtac tattcacggc aacaccgagg aactgcgcca    2100
gatggctgct tctagggagg tgccaaggcc actgagtaca ctgcctatgt ttaatgtgca    2160
cactggcgaa cggctgcccc ctagagtgga tagcgcccag gtgccactga ttctggacca    2220
gcattgaggc cgcaataaaa gatctttatt ttcattagat ctgtgtgttg gttttttgtg    2280
tgtcctgcag gggcgcgcct ctagagcatg gctacgtaga taagtagcat ggcgggttaa    2340
tcattaacta caaggaaccc ctagtgatgg agttggccac tccctctctg cgcgctcgct    2400
cgctcactga ggccgggcga ccaaaggtcg cccgacgccc gggctttgcc cggcggcct    2460 cagtgagcga gcgagcgcgc agctggcgta atagcgaaga ggcccgcacc gatcgccctt    2520
cccaacagtt gcgcagcctg aatggcgaat ggcgattccg ttgcaatggc tggcggtaat    2580
attgttctgg atattaccag caaggccgat agtttgagtt cttctactca ggcaagtgat    2640
gttattacta atcaaagaag tattgcgaca acggttaatt tgcgtgatgg acagactctt    2700
ttactcggtg gcctcactga ttataaaaac acttctcagg attctggcgt accgttcctg    2760
tctaaaatcc ctttaatcgg cctcctgttt agctcccgct ctgattctaa cgaggaaagc    2820
acgttatacg tgctcgtcaa agcaaccata gtacgcgccc tgtagcggcg cattaagcgc    2880
ggcgggtgtg gtggttacgc gcagcgtgac cgctacactt gccagcgccc tagcgcccgc    2940
tcctttcgct ttcttccctt cctttctcgc cacgttcgcc atcttcaaat atgtatccgc    3000
tcatgagaca ataaccctga taaatgcttc aataatattg aaaaaggaag agtcctgagg    3060
cggaaagaac cagctgtgga atgtgtgtca gttagggtgt ggaaagtccc caggctcccc    3120
agcaggcaga agtatgcaaa gcatgcatct caattagtca gcaaccaggt gtggaaagtc    3180
cccaggctcc ccagcaggca gaagtatgca aagcatgcat ctcaattagt cagcaaccat    3240
agtcccgccc ctaactccgc ccatggctg actaattttt tttatttatg cagaggccga    3300 ggcgcctcg gcctctgagc tattccagaa gtagtgagga ggcttttttg gaggcctagg    3360
cttttgcaaa gatcgatcaa gagacaggat gaggatcgtt tcgcatgatt gaacaagatg    3420
gattgcacgc aggttctccg gccgcttggg tggagaggct attcggctat gactgggcac    3480
aacagacaat cggctgctct gatgccgccg tgttccggct gtcagcgcag ggcgcccgg    3540 ttcttttgt caagaccgac ctgtccggtg ccctgaatga actgcaagac gaggcagcgc    3600
```

```
ggctatcgtg gctggccacg acgggcgttc cttgcgcagc tgtgctcgac gttgtcactg    3660
aagcgggaag ggactggctg ctattgggcg aagtgccggg gcaggatctc ctgtcatctc    3720
accttgctcc tgccgagaaa gtatccatca tggctgatgc aatgcggcgg ctgcatacgc    3780
ttgatccggc tacctgccca ttcgaccacc aagcgaaaca tcgcatcgag cgagcacgta    3840
ctcggatgga agccggtctt gtcgatcagg atgatctgga cgaagagcat caggggctcg    3900
cgccagccga actgttcgcc aggctcaagg cgagcatgcc cgacggcgag gatctcgtcg    3960
tgacccatgg cgatgcctgc ttgccgaata tcatggtgga aaatggccgc ttttctggat    4020
tcatcgactg tggccggctg gtgtggcgg accgctatca ggacatagcg ttggctaccc    4080
gtgatattgc tgaagagctt ggcggcgaat gggctgaccg cttcctcgtg ctttacggta    4140
tcgccgctcc cgattcgcag cgcatcgcct tctatcgcct tcttgacgag ttcttctgag    4200
cgggactctg gggttcgaaa tgaccgacca agcgacgccc aacctgccat cacgagattt    4260
cgattccacc gccgccttct atgaaaggtt gggcttcgga atcgttttcc gggacgccgg    4320
ctggatgatc ctccagcgcg gggatctcat gctggagttc ttcgcccacc ctaggggggag    4380 gctaactgaa acacggaagg agacaatacc ggaaggaacc cgcgctatga cggcaataaa    4440
aagacagaat aaaaacgttg cgcaaactat taactggcga actacttact ctagcttccc    4500
ggcaacaatt aatagactgg atggaggcgg ataaagttgc aggaccactt ctgcgctcgg    4560
cccttccggc tggctggttt attgctgata atctggagc cggtgagcgt gggtctcgcg    4620
gtatcattgc agcactgggg ccagatggta agccctcccg tatcgtagtt atctacacga    4680
cggggagtca ggcaactatg gatgaacgaa atagacagat cgctgagata ggtgcctcac    4740
tgattaagca ttggtaactg tcagaccaag tttactcata tatactttag attgatttaa    4800
aacttcattt ttaatttaaa aggatctagg tgaagatcct ttttgataat ctcatgacca    4860
aaatccctta acgtgagttt tcgttccact gagcgtcaga ccccgtagaa aagatcaaag    4920
gatcttcttg agatcctttt tttctgcgcg taatctgctg cttgcaaaca aaaaaaccac    4980
cgctaccagc ggtggtttgt ttgccggatc aagagctacc aactcttttt ccgaaggtaa    5040
ctggcttcag cagagcgcag ataccaaata ctgttcttct agtgtagccg tagttaggcc    5100
accacttcaa gaactctgta gcaccgccta catacctcgc tctgctaatc ctgttaccag    5160
tggctgctgc cagtggcgat aagtcgtgtc ttaccgggtt ggactcaaga cgatagttac    5220
cggataaggc gcagcggtcg ggctgaacgg ggggttcgtg cacacagccc agcttggagc    5280
gaacgaccta caccgaactg agatacctac agcgtgagct atgagaaagc gccacgcttc    5340
ccgaagggag aaaggcggac aggtatccgg taagcggcag ggtcggaaca ggagagcgca    5400
cgagggagct tccaggggga aacgcctggt atctttatag tcctgtcggg tttcgccacc    5460
tctgacttga gcgtcgattt ttgtgatgct cgtcaggggg gcggagccta tggaaaaacg    5520
ccagcaacgc ggcctttttta cggttcctgg ccttttgctg ccttttgct cacatgttct    5580 ttcctgcgtt atcccctgat tctgtggata accgtattac cgcctttgag tgagctgata    5640
ccgctcgccg cagccgaacg accgagcgca gcgagtcagt gagcgaggaa gcggaagagc    5700
gcccaatacg caaaccgcct ctccccgcgc gttggccgat tcattaatg              5749
```

<210> SEQ ID NO 9
<211> LENGTH: 22
<212> TYPE: DNA
<213> ORGANISM: Artificial Sequence
<220> FEATURE:

```
<223> OTHER INFORMATION: Synthetic Primer

<400> SEQUENCE: 9
cagggctggg agctgggttc tg                                            22

<210> SEQ ID NO 10
<211> LENGTH: 18
<212> TYPE: DNA
<213> ORGANISM: Artificial Sequence
<220> FEATURE:
<223> OTHER INFORMATION: Synthetic Primer

<400> SEQUENCE: 10
cccagggcct tgatgcct                                                 18

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
gctatcagga catagcgttg gcta                                          24

<210> SEQ ID NO 12
<211> LENGTH: 23
<212> TYPE: DNA
<213> ORGANISM: Artificial Sequence
<220> FEATURE:
<223> OTHER INFORMATION: Synthetic Primer

<400> SEQUENCE: 12
acccgagatg cctggttata att                                           23

<210> SEQ ID NO 13
<211> LENGTH: 24
<212> TYPE: DNA
<213> ORGANISM: Artificial Sequence
<220> FEATURE:
<223> OTHER INFORMATION: Synthetic Primer

<400> SEQUENCE: 13
tccatggtgt acagagccta agac                                          24

<210> SEQ ID NO 14
<211> LENGTH: 25
<212> TYPE: DNA
<213> ORGANISM: Artificial Seuqence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (25)..(25)
<223> OTHER INFORMATION: IABkFQ

<400> SEQUENCE: 14
ctgctgcctg agcctgagcg gttac                                         25
```